(12) United States Patent
Kron et al.

(10) Patent No.: US 11,747,252 B2
(45) Date of Patent: Sep. 5, 2023

(54) RAPID PROFILE VISCOMETER DEVICES AND METHODS

(71) Applicant: BioFluid Technology, Inc., Bryn Mawr, PA (US)

(72) Inventors: Reuben E Kron, Bryn Mawr, PA (US); Stephen J Kron, Oak Park, IL (US)

(73) Assignee: BioFluid Technology, Inc., Bryn Mawr, PA (US)

( * ) Notice: Subject to any disclaimer, the term of this patent is extended or adjusted under 35 U.S.C. 154(b) by 0 days.

(21) Appl. No.: 17/497,292

(22) Filed: Oct. 8, 2021

(65) Prior Publication Data
US 2022/0196533 A1 Jun. 23, 2022

Related U.S. Application Data

(60) Provisional application No. 63/090,093, filed on Oct. 9, 2020.

(51) Int. Cl.
*G01N 11/04* (2006.01)

(52) U.S. Cl.
CPC .................... *G01N 11/04* (2013.01)

(58) Field of Classification Search
CPC ........ G01N 11/00; G01N 11/04; G01N 11/02; G01N 11/06; G01N 11/08; G01N 2011/006; G01N 2011/0006; G01N 2011/0026
See application file for complete search history.

(56) References Cited

U.S. PATENT DOCUMENTS

| 3,720,097 A | 3/1973 | Kron |
| 4,858,127 A * | 8/1989 | Kron ............... G01N 11/00 73/54.09 |
| 6,322,524 B1 * | 11/2001 | Kensey ............ A61B 5/15003 600/573 |

(Continued)

FOREIGN PATENT DOCUMENTS

| CA | 1294147 | 1/1992 | |
| CN | 109342271 A * | 2/2019 | ............ G01N 11/06 |

(Continued)

OTHER PUBLICATIONS

Nader, Elie, et al. "Blood rheology: key parameters, impact on blood flow, role in sickle cell disease and effects of exercise." Frontiers in physiology (2019), (Year: 2019).*

(Continued)

*Primary Examiner* — Daniel S Larkin
*Assistant Examiner* — Fatemeh Esfandiari Nia
(74) *Attorney, Agent, or Firm* — BakerHostetler

(57) ABSTRACT

Provided are apparatuses and methods for rapid viscometry of whole blood, plasma, and/or whole blood during coagulation. The disclosed technology measures the blood viscosity through the full range of flow rates found in the cardiovascular system. This in vitro test can be performed on fresh or anticoagulated whole blood to predict the flow properties (e.g., viscosity) anywhere in the body from the aorta to the deep veins of the leg. The result is a flow-rate dependent blood viscosity curve (viscosity profile) that helps the clinician predict and manage the patient's vulnerability to thrombosis and embolism, which is of particular relevance to COVID-19 patients and/or ICU patients.

27 Claims, 40 Drawing Sheets

(56) References Cited

U.S. PATENT DOCUMENTS

| | | | | |
|---|---|---|---|---|
| 2009/0293594 | A1* | 12/2009 | He | G01N 11/08 73/54.09 |
| 2012/0127466 | A1* | 5/2012 | Karnes | G01N 33/2811 356/319 |
| 2013/0220027 | A1* | 8/2013 | Calderin | G01F 1/34 73/863.02 |
| 2019/0317000 | A1* | 10/2019 | Johns | A61B 5/02035 |

FOREIGN PATENT DOCUMENTS

| | | | | |
|---|---|---|---|---|
| EP | | 0492664 A1 * | 12/1991 | |
| WO | WO-2020070359 A1 * | 4/2020 | | G01N 11/08 |

OTHER PUBLICATIONS

Arulkumaran N, et. al. Plasma exchange for COVID-19 thrombo-inflammatory disease. EJHaem. Nov. 30, 2020. doi: 10.1002/jha2.140. Online ahead of print.

Berkman S A, Tapson V F, COVID-19 and Its Implications for Thrombosis and Anticoagulation. Semin Respir Crit Care Med. Feb. 6, 2021. doi: 10.1055/s-0041-1722992. Online ahead of print.

Bime C, Casanova N G, Nikolich-Zugich J, Knox K S, Camp S M, Garcia J G N, Strategies to DAMPen COVID-19-mediated lung and systemic inflammation and vascular injury. Transl Res. Dec. 20, 2020;S1931-5244(20)30303-0. doi: 10.1016/j.trsl.2020.12.008. Online ahead of print.

Chang J. COVID-19 Sepsis: Pathogenesis and Endothelial Molecular Mechanisms Based on "Two-Path Unifying Theory" of Hemostasis and Endotheliopathy-Associated Vascular Microthrombotic Disease, and Proposed Therapeutic Approach with Antimicrothrombotic Therapy. Vasc Health Risk Manag. Jun. 1, 2021;17:273-298. doi: 10.2147/VHRM.S299357. eCollection 2021.

Chen B, et. al., High prevalence of occult thrombosis in mild/moderate COVID-19. Int J Infect Dis. Dec. 19, 2020; S1201-9712(20)32566-2. doi: 10.1016/j.ijid.2020.12.042. Online ahead of print.

Chen W, Jing YP, Anatomical and Pathological Observation and Analysis of SARS and COVID-19: Microthrombosis Is the Main Cause of Death. Biol Proced Online. Jan. 20, 2021;23(1):4. doi: 10.1186/s12575-021-00142-y.

Chidambaram V, et. al., Factors associated with disease severity and mortality among patients with COVID-19: A systematic review and meta-analysis. PLoS One. Nov. 18, 2020;15(11):e0241541. doi: 10.1371/journal.pone.0241541. eCollection 2020.

Faqihi, F et al., Therapeutic plasma exchange in patients with life-threatening COVID-19: a randomised controlled clinical trial. Int J Antimicrob Agents. May 2021;57(5):106334. doi: 10.1016/j.ijantimicag.2021.106334. Epub Apr. 7, 2021.

Iba T, Levy J H, Levi M, Thachil J, Coagulopathy in COVID-19. J Thromb Haemost. Sep. 2020;18(9):2103-2109. doi: 10.1111/jth.14975. Epub Jul. 21, 2020.

Ji P, et al. Association of elevated inflammatory markers and severe COVID-19: A meta-analysis Medicine ( Baltimore). Nov. 20, 2020;99(47):e23315. doi: 10.1097/MD.0000000000023315.

Kamran SM, et al.,Therapeutic plasma exchange for coronavirus disease-2019 triggered cytokine release syndrome; a retrospective propensity matched control study. PLOS One. Jan. 2021; https://doi.org/10.1371/journal.pone.0244853.

Kensey K, Rheology: an overlooked component of vascular disease. Clin Appl Thromb Hemost. Apr. 2003;9(2):93-9. doi: 10.1177/107602960300900201.

Klarhöfer M, et al., High-resolution blood flow velocity measurements in the human finger. Magn Reson Med. Apr. 2001;45(4):716-9. doi: 10.1002/mrm.1096. PMID: 11284002.

Lemos ABC, et. al., Therapeutic Anticoagulation in COVID-19 Patients. Thromb Res. May 3, 2021;203:72-73. doi: 10.1016/j.thromres.2021.04.027. Online ahead of print.

Truong et al. Therapeutic plasma exchange for COVID-19-associated hyperviscosity, Transfusion. Jul. 2020 19.1111/trf.16218. doi: 10.1111/trf.16218. Online ahead of print.

Maier C, et al., COVID-19-associated hyperviscosity: a link between inflammation and thrombophilia? Lancet. Jun. 6, 2020;395(10239):1758-1759. doi: 10.1016/30140-6736(20)31209-5. Epub May 25, 2020.

Mousavi-Roknabadi RS. et. al., Investigation of plasma exchange and hemoperfusion effects and complications for the treatment of patients with severe COVID-19 (SARS-CoV-2) disease: a systematic scoping review. J Med Virol. Jul. 6, 2021. doi: 10.1002/jmv.27182. Online ahead of print.

Mungmunpuntipantip R and Wiwanitkit V. Blood Viscosity at the First Clinical Presentation in Fatal and Non-Fatal COVID-19: An Observation. Clin Appl Thromb Hemost. Jan.-Dec. 2021; 27:10760296211006779. Published online Apr. 28, 2021.

Norton A, Could COVID-19 Someday Become Seasonal, Like Flu? Sep. 15, 2020; Jan. 6, 2021;https://www.webmd.com/lung/news/20200915/could-covd-19-someday-become-seasonal-like-flu#1.

Salisbury R, et. al., Incidence of symptomatic, image-confirmed venous thromboembolism following hospitalization for COVID-19 with 90-day follow-up. Blood Adv. Dec. 22, 2020;4(24):6230-6239. doi: 10.1182/bloodadvances.2020003349.

Temesgen Z, et. al., Lenzilumab Efficacy and Safety in Newly Hospitalized COVID-19 Subjects: Results From the Live-Air Phase 3 Randomized Double-Blind Placebo-Controlled Trial. medRxiv. May 5, 2021;2021.05.01.21256470. doi: 10.1101/2021.05.01.21256470. Preprint.

Ahmed S, Zimba O, Gasparyan AY. 2020 Thrombosis in Coronavirus disease 2019 (COVID-19) through the prism of Virchow's triad. Clin Rheumatol Sep;39(9):2529-2543.

Garcia, Luis F. 2020 Immune Response, Inflammation, and the Clinical Spectrum of COVID 19. Front Immunol Jun. 16;11:1441.

McFadyen JD, Stevens H, Peter K. 2020 The Emerging Threat of (Micro)Thrombosis in COVID-19 and Its Therapeutic Implications. Circ Res. Jul. 31;127(4):571-587.

Goshua G, et al. 2020 Endotheliopathy in COVID-19-associated coagulopathy: evidence from a single-centre, cross-sectional study. Lancet Haematol. Aug;7(8):e575-e582.

* cited by examiner

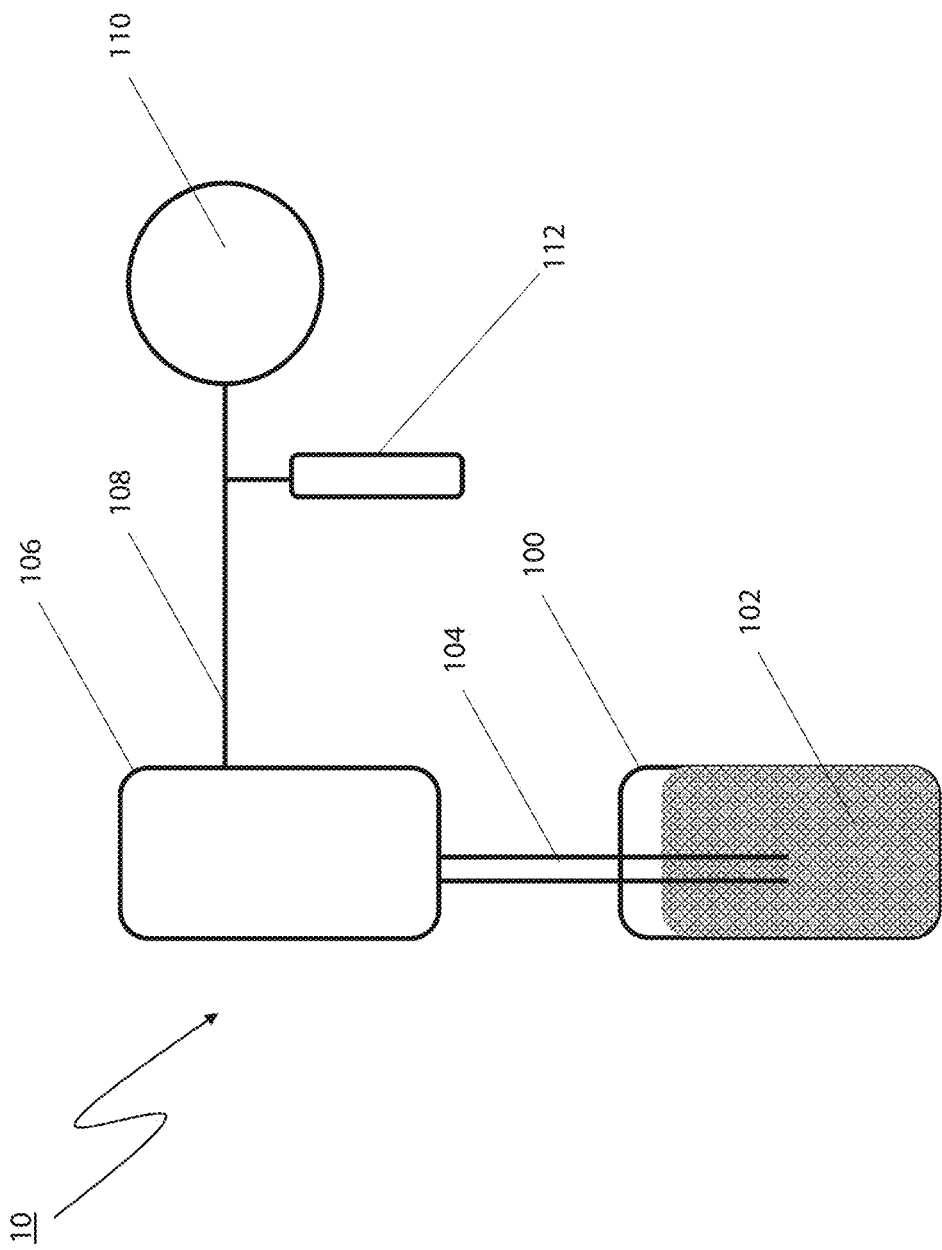

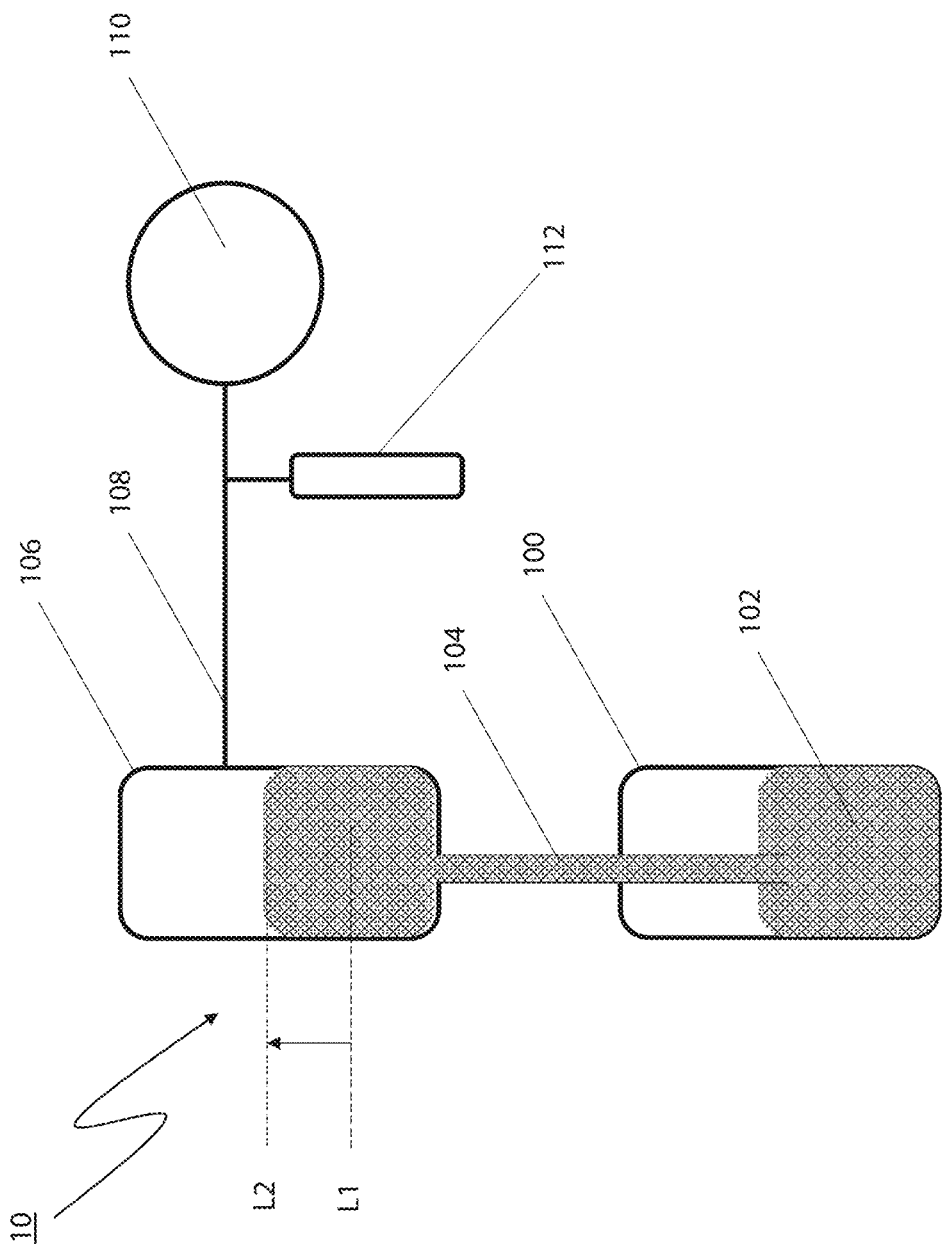

RAPID PROFILE VISCOMETER DEVICES AND METHODS

RELATED APPLICATIONS

The present application claims priority to and the benefit of U.S. patent application No. 63/090,093, "Rapid Profile Viscometer" (filed Oct. 9, 2020), the entirety of which application is incorporated herein by reference for any and all purposes.

TECHNICAL FIELD

The present disclosure relates to the field of clinical analysis devices.

BACKGROUND

COVID-19 has had a profound effect on global health, and there is clinical evidence that COVID-19 is a contagious inflammatory disorder that can affect any organ system. The pathophysiology of this novel viral disease is complex and not fully understood. Why some patients infected with the virus remain asymptomatic while others succumb to organ failure remains to be explained.

At this point there remains to be found a specific treatment for COVID-19, but a variety of existing treatments are being applied with varying levels of success. This is especially evident in the ICU where the sickest victims are empirically treated with a cocktail of therapies, including anti-inflammatory and anti-thrombotic agents.

This therapeutic approach is justified by the belief that the intensity of the inflammatory response to COVID-19 infection may be the major factor responsible for organ failure, thus use of corticosteroids. Also, the viral infection is accompanied by pervasive vascular complications—including myocardial infarction, stroke and renal failure. Without being bound by any particular theory, it has been proposed that the cardiovascular and cerebrovascular systems can be compromised by a pervasive vasculitis that disposes the blood to intravascular thrombosis, thus use of anticoagulants.

It is not usual in medicine to prescribe a treatment for a serious physiological disorder without objectively monitoring the physiological consequences of the treatment. If insulin is administered for management of diabetes, we carefully follow the blood glucose levels, and adjust treatment accordingly. This level of care for diabetes is not a problem because our diagnostic technology is easy to use and provides immediate results. The same level of care should apply to the use of powerful anti-inflammatory and anticoagulant medications, and especially when administered to our most vulnerable COVID-19 patients in the ICU.

Unfortunately, testing for and titrating the concentration of inflammatory (also termed "reactive") and coagulopathic proteins in the blood are expensive, inconvenient, and time-consuming clinical laboratory procedures. For this reason, standard laboratory practice may not be adequate to monitor the effects of powerful drugs on an unconscious patient whose life is being supported by a respirator. ICU clinicians need more timely information to guide their use of these potentially life-saving empirical treatments.

Thus, there is a need in the field for an ICU "bedside" or other point-of-care (POC) test, in particular one that can take a small sample of blood (e.g., from an existing IV port) to measure the effects of these empirical treatments. It is useful to know how the drugs modify reactive proteins and clotting factors that reflect the body's inflammatory reaction to the infection and response to treatment; it is also useful to analyze the effects of the infection on blood flow, blood clotting and vascular integrity.

SUMMARY

Rapid Profile Viscometer

C-Reactive Protein (CRP), erythrocyte sedimentation rate (ESR), and plasma viscosity (PV) tests generate similar findings in inflammatory disorders. But CRP and ESR are expensive and time consuming and are best performed in the clinical lab. Also, CRP is very sensitive and can remain elevated after clinical remission, while ESR is an indirect measure that depends on RBC clumping to disclose elevated reactive proteins. CRP and ESR are not conducive to on-the-spot testing.

The disclosed rapid profile viscometer (which can be termed an "RPV") can provide clinically important POC (bedside) data about the actual sources of hyperviscosity and reduced clotting time in a faster and more convenient test than either CRP or ESR. In less than a minute the RPV can provide a full profile of the whole blood viscosities that exist throughout the body, ranging from the aorta to the deep veins of the leg, from either a fresh or anticoagulated blood sample. The test gives a picture of blood flow conditions existing in various parts of the vasculature.

WBV and PV can be quickly performed bedside as many times as needed using fresh or anticoagulated blood samples. Equipment for such use can include, e.g., Vacutainer™ tubes, a small centrifuge (for PV), and the disclosed RPV and any other disposables. The test can use a 1-2 ml sample of plasma or whole blood and takes only seconds to perform. WBV can be measured to assess the flow state and likelihood of abnormal clotting in vital organs by determining viscosity and clotting time with the RPV Viscometer and Coagulometer functions.

The test can be repeated using the same disposable with the same (or additional) anticoagulated samples to confirm the findings. Also, the test can be repeated as frequently as needed to monitor the patient's response to treatment, and to immediately act on that data. Alternative methods for performing blood viscometry are costly and time-consuming, and require specially trained personnel in the clinical lab setting.

The disclosed RPV provides a quick and easy point of care (POC) or even bedside test that can help in titrating anti-inflammatory, anticoagulant, and intravascular plasma replacement therapies in the ICU hospitalized patient, and especially in those patients with COVID-19. Blood samples can be withdrawn, e.g., from a vein or an IV port using a syringe or Vacutainer system under applicable ICU protocol. Here is provided is a simple, safe technology that does not require expensive personnel to utilize.

In meeting the long-felt needs in the field, the present disclosure provides methods, comprising: encouraging one or more of (1) anticoagulated whole blood from a subject patient, (2) a plasma from the subject, and/or (3) fresh whole blood undergoing coagulation through a conduit into and/or out of an enclosed volume; monitoring one or more pressures related to the encouraging as a function of time so as to generate one or more sets of pressure vs. time data; and based on the one or more sets of pressure vs. time data, determining a viscosity (or other measure of resistance to flow) of the anticoagulated whole blood, the plasma, and/or the fresh whole blood during coagulation.

In one exemplary embodiment, the method can include first collecting blood or plasma sample in a Vacutainer or equivalent receptacle; drawing sample into an enclosed (sealed) space; and discharging sample back into the Vacutainer. A time-pressure curve is recorded for both the drawing up and discharging, and the data can be averaged so as to cancel out hydrostatic, cohesive/adhesive and diabatic errors (as well as creating a replication of the experiment to improve and assure accuracy/precision).

Also provided are apparatuses, comprising: a first conduit configured to communicate a fluid therein; a first enclosed volume, the first enclosed volume being in fluid communication with the first conduit; a transducer, the transducer configured to measure a pressure within the first enclosed volume related to fluid entry and/or fluid egress from the first enclosed volume; and a source of positive and/or negative pressure, the source being capable of fluid communication with the first enclosed volume, the source configured to encourage fluid from the first conduit into the first enclosed volume and/or to encourage fluid out of the first enclosed volume.

Also provided are methods, comprising: encouraging a fluid sample through a conduit into and/or out of a reservoir, the fluid sample optionally comprising one or more of (1) whole blood, (2) a blood plasma, or (3) whole blood during coagulation; monitoring a pressure within the reservoir related to the encouraging as a function of time so as to generate at least a first set of pressure vs. time data; and based at least in part on the first set of pressure vs. time data, determining one or more of a viscosity, a viscosity as a function of shear rate, or a flow resistance of the fluid sample.

Further provided is an apparatus, comprising: a conduit configured to communicate a fluid therein; a reservoir, the reservoir being in fluid communication with the conduit, the reservoir optionally being expandable; a transducer, the transducer configured to measure a pressure within the first reservoir related to fluid entry and/or fluid egress from the expandable reservoir; and a memory in communication with the transducer, the memory configured to record at least a first set of pressure vs. time data related to fluid entry and/or fluid egress from the expandable reservoir.

Also disclosed are methods, comprising effecting operation of an apparatus according to the present disclosure, e.g., according to any one of Aspects 14-20.

BRIEF DESCRIPTION OF THE DRAWINGS

The file of this patent or application contains at least one drawing/photograph executed in color. Copies of this patent or patent application publication with color drawing(s)/photograph(s) will be provided by the Office upon request and payment of the necessary fee.

In the drawings, which are not necessarily drawn to scale, like numerals can describe similar components in different views. Like numerals having different letter suffixes can represent different instances of similar components. The drawings illustrate generally, by way of example, but not by way of limitation, various aspects discussed in the present document. In the drawings:

FIGS. 21A-21D provide a depiction of the operation of a system according to the present disclosure.

DETAILED DESCRIPTION OF ILLUSTRATIVE EMBODIMENTS

Figure 1:
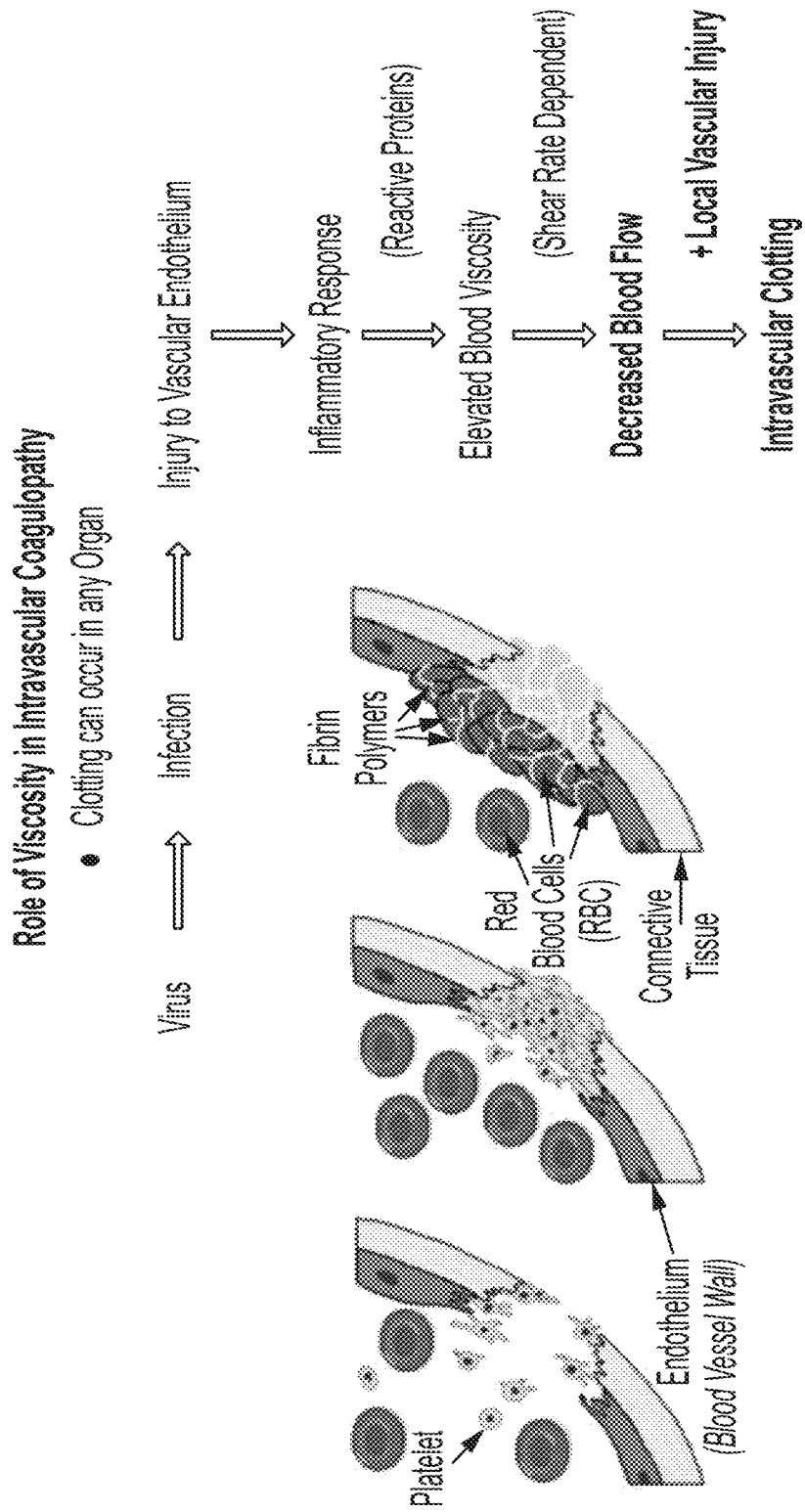
FIG. 1 provides a depiction of the role of viscosity in intravascular coagulopathy.

The present disclosure may be understood more readily by reference to the following detailed description of desired embodiments and the examples included therein.

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing. All publications, patent applications, patents and other references mentioned herein are incorporated by reference in their entirety. The materials, methods, and examples disclosed herein are illustrative only and not intended to be limiting.

The singular forms "a," "an," and "the" include plural referents unless the context clearly dictates otherwise.

As used in the specification and in the claims, the term "comprising" can include the embodiments "consisting of" and "consisting essentially of." The terms "comprise(s)," "include(s)," "having," "has," "can," "contain(s)," and variants thereof, as used herein, are intended to be open-ended transitional phrases, terms, or words that require the presence of the named ingredients/steps and permit the presence of other ingredients/steps. However, such description should be construed as also describing compositions or processes as "consisting of" and "consisting essentially of" the enumerated ingredients/steps, which allows the presence of only the named ingredients/steps, along with any impurities that might result therefrom, and excludes other ingredients/steps.

As used herein, the terms "about" and "at or about" mean that the amount or value in question can be the value designated by some other value approximately or about the same. It is generally understood, as used herein, that it is the nominal value indicated ±10% variation unless otherwise indicated or inferred. The term is intended to convey that similar values promote equivalent results or effects recited in the claims. That is, it is understood that amounts, sizes, formulations, parameters, and other quantities and characteristics are not and need not be exact, but can be approximate and/or larger or smaller, as desired, reflecting tolerances, conversion factors, rounding off, measurement error and the like, and other factors known to those of skill in the art. In general, an amount, size, formulation, parameter or other quantity or characteristic is "about" or "approximate" whether or not expressly stated to be such. It is understood that where "about" is used before a quantitative value, the parameter also includes the specific quantitative value itself, unless specifically stated otherwise.

Unless indicated to the contrary, the numerical values should be understood to include numerical values which are the same when reduced to the same number of significant figures and numerical values which differ from the stated value by less than the experimental error of conventional measurement technique of the type described in the present application to determine the value.

All ranges disclosed herein are inclusive of the recited endpoint and independently of the endpoints (e.g., "between 2 grams and 10 grams, and all the intermediate values includes 2 grams, 10 grams, and all intermediate values"). The endpoints of the ranges and any values disclosed herein are not limited to the precise range or value; they are sufficiently imprecise to include values approximating these ranges and/or values. All ranges are combinable.

As used herein, approximating language can be applied to modify any quantitative representation that can vary without resulting in a change in the basic function to which it is related. Accordingly, a value modified by a term or terms, such as "about" and "substantially," may not be limited to the precise value specified, in some cases. In at least some instances, the approximating language can correspond to the precision of an instrument for measuring the value. The modifier "about" should also be considered as disclosing the range defined by the absolute values of the two endpoints. For example, the expression "from about 2 to about 4" also discloses the range "from 2 to 4." The term "about" can refer to plus or minus 10% of the indicated number. For example, "about 10%" can indicate a range of 9% to 11%, and "about 1" can mean from 0.9-1.1. Other meanings of "about" can be apparent from the context, such as rounding off, so, for example "about 1" can also mean from 0.5 to 1.4. Further, the term "comprising" should be understood as having its open-ended meaning of "including," but the term also includes the closed meaning of the term "consisting." For example, a composition that comprises components A and B can be a composition that includes A, B, and other components, but can also be a composition made of A and B only. Any documents cited herein are incorporated by reference in their entireties for any and all purposes.

Provided here is, inter alia, a Rapid Profile Viscometer (RPV) that can measure the viscosity of whole blood and/or blood plasma at the bedside in a matter of seconds. The disclosed technology also generates a viscosity profile of non-Newtonian fluids such as whole blood. The viscosity of whole blood increases as flow rate decreases. Elevated blood viscosity predisposes the slow flow vessels (such as the deep veins of the leg) to intravascular clotting and embolism. This is the bane of the COVID-19 ICU patient.

The disclosed technology measures the blood viscosity through a range of flow rates found in the cardiovascular system and can do so over the full range of physiological flow rates and/or pressures. The disclosed technology can be performed on fresh or anticoagulated whole blood to predict the flow properties (e.g., viscosity) anywhere in the body from the aorta to the deep veins of the leg. The disclosed technology can provide a flow-rate dependent blood viscosity curve (viscosity profile) that helps the clinician predict and manage the patient's vulnerability to thrombosis and embolism.

First Order Decay is the physical principle that can be used to measure and/or estimate (1) Whole Blood Viscosity (WBV), (2) Plasma Viscosity (PV) and (3) blood coagulation with a Rapid Profile Viscometer (RPV). First Order Decay describes the relationship between pressure and time in the RPV, and as a consequence of First Order Decay, the slope of pressure plotted on a log scale vs. time plotted on a linear scale gives the relative viscosity of Newtonian fluids such as blood plasma (PV), while the instantaneous plot of the log of pressure vs. time provides the shear rate dependent viscosity of non-Newtonian fluids such as blood. Each point on the log pressure curve reflects the relative viscosity of the sample (e.g., whole blood vs the control) at that shear rate. One can measure the volumetric flow within the conduit; one can know the total air volume in a system (which is enclosed), which can include the volume of the reservoir, tubing, and other components. By measuring the change in pressure when the volume of the system is changed (e.g., via pulling up on a syringe of air, by adding 1 mL of air, etc.).

Figure 3:
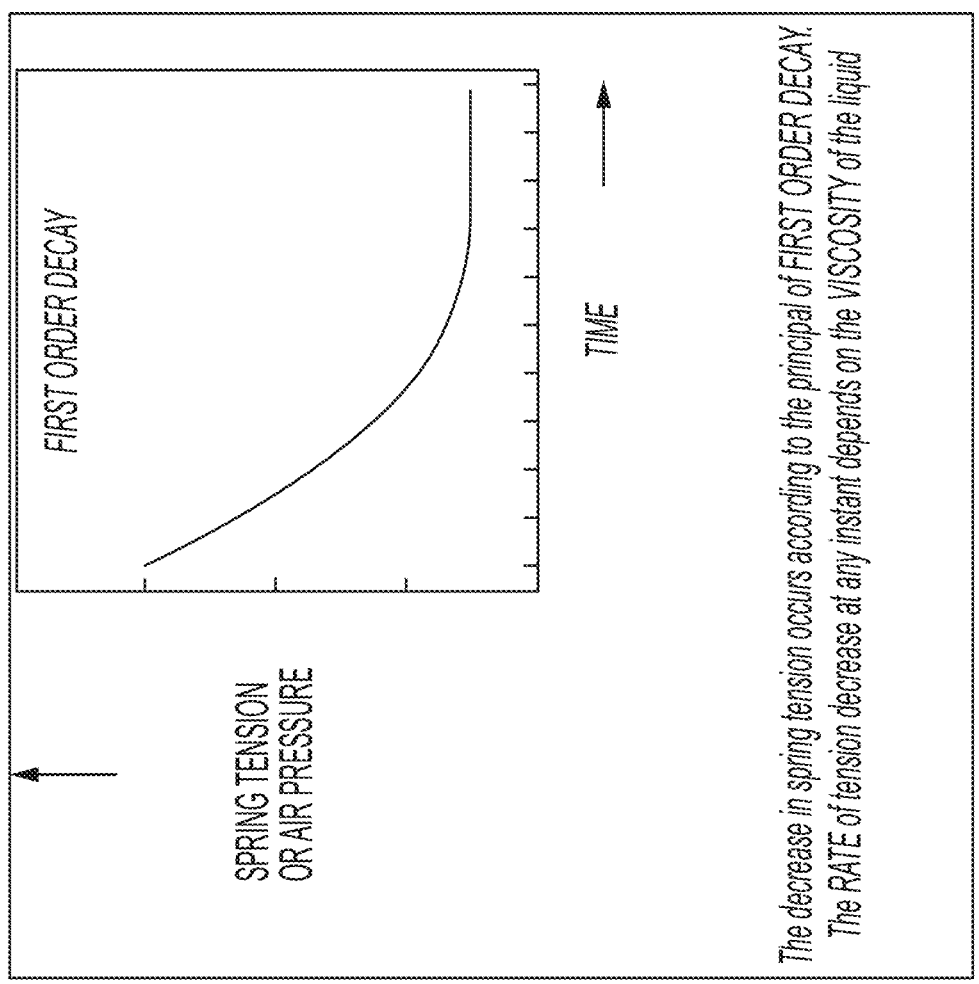
FIG. 3 provides an illustration of first order decay.

An example relationship between pressure and time in an RPV is shown in FIG. 3. With all other factors held constant, the relationship between air pressure and time in the RPV is determined by viscosity of the fluid.

Figure 4:
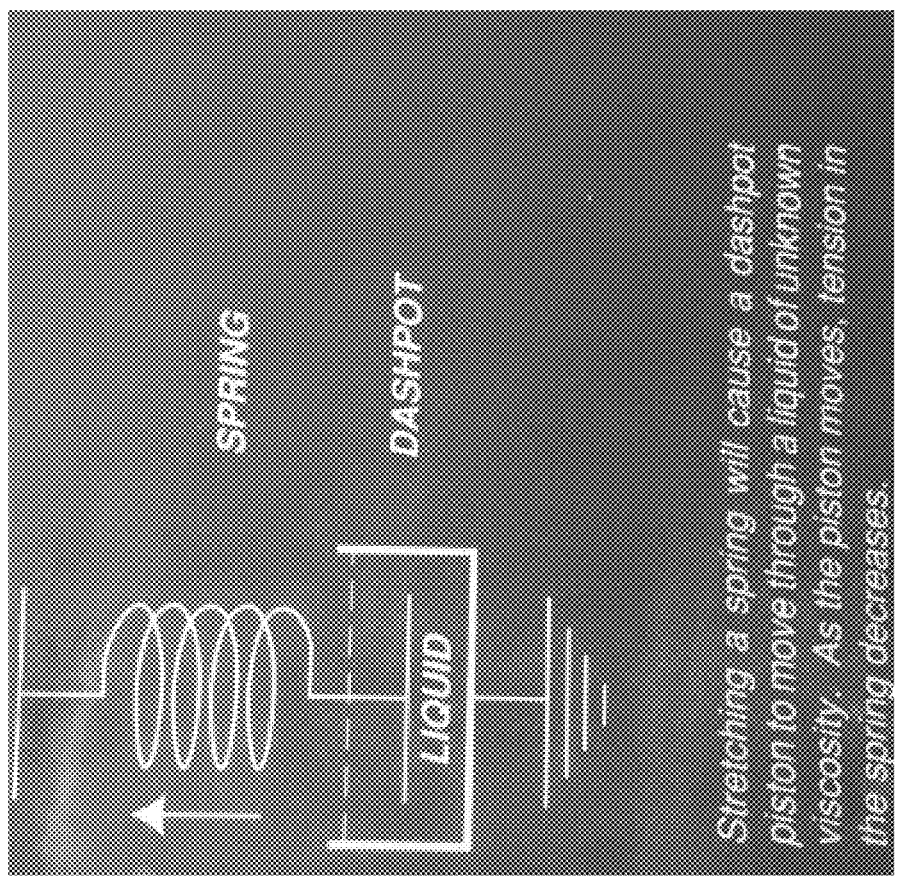
FIG. 4 provides an illustration of a spring engaged with a dashpot piston.

An example of first order decay is provided by FIG. 4, which depicts a spring and a dashpot. As shown, the piston moves through the fluid at a gradually decreasing rate. The rate of movement is related to the resistance to flow created by the viscosity of the liquid.

Figure 5:
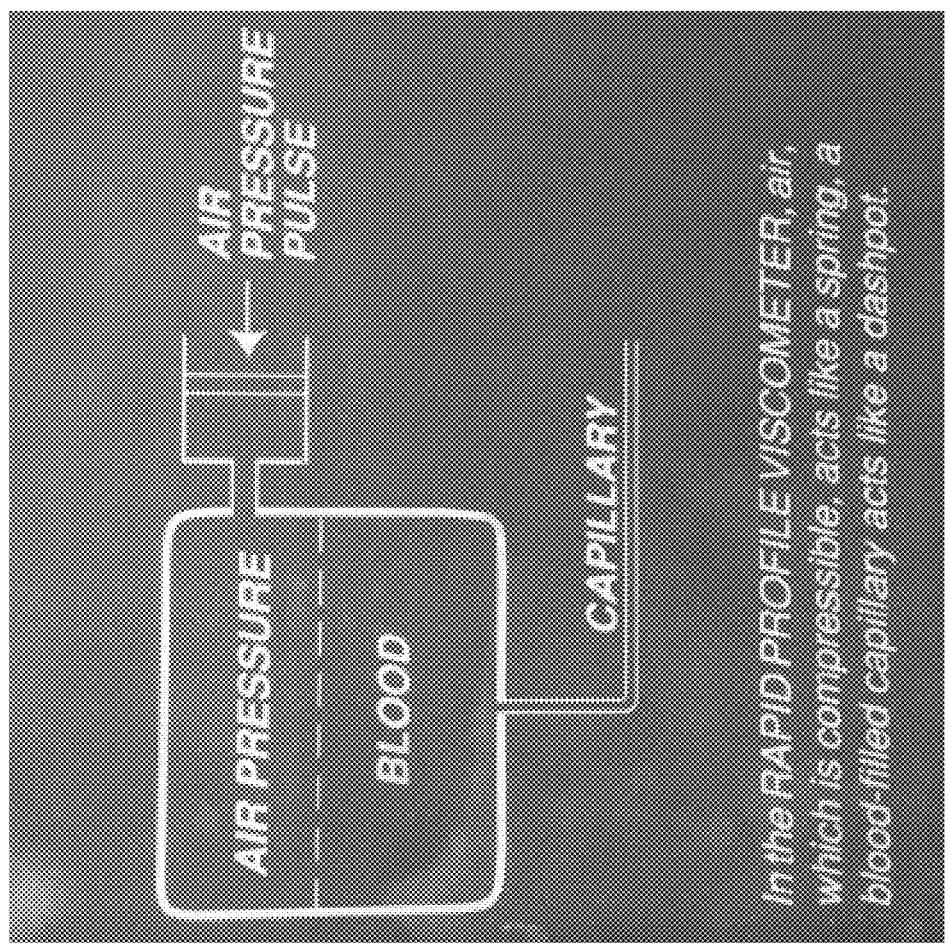
FIG. 5 provides an illustration of the principle of operation of the disclosed devices.

FIG. 5 provides a non-limiting illustration of a principle underlying the disclosed devices. As shown, compressed air acts like a spring, and the capillary acts like a dashpot in the RPV.

Figure 6:
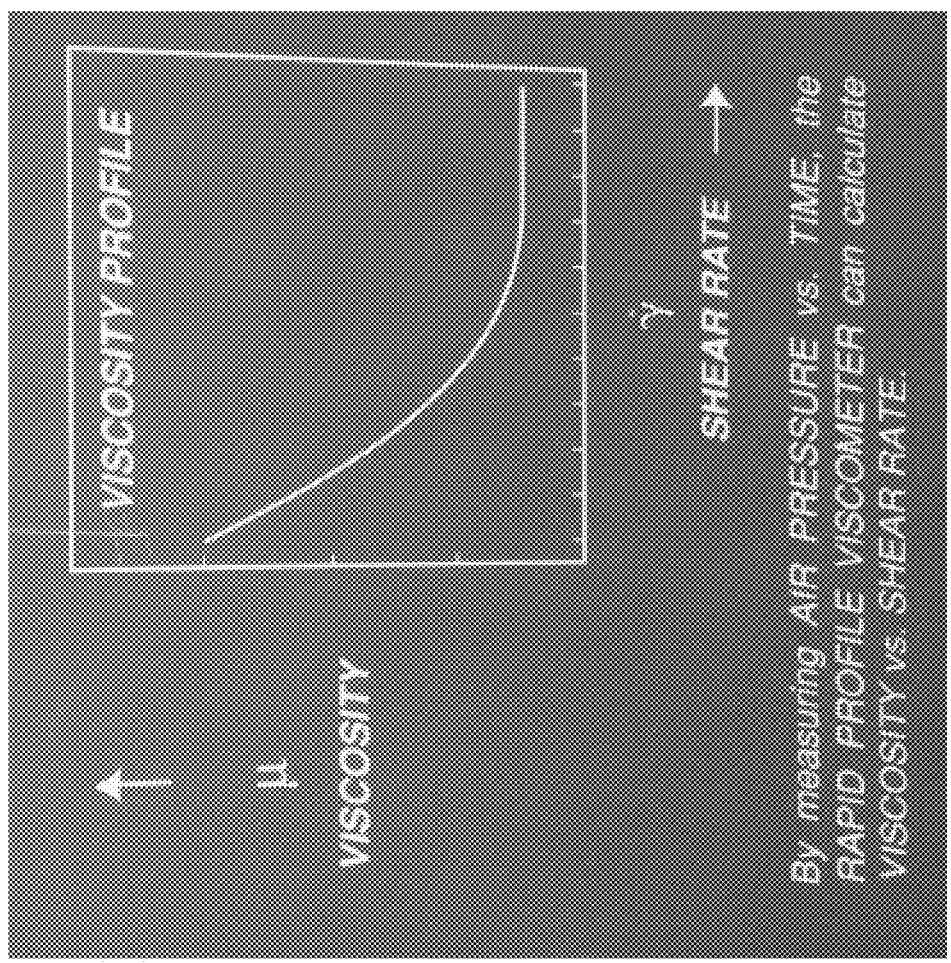
FIG. 6 provides an illustration of a viscosity vs. shear rate profile for an exemplary fluid.

FIG. 6 provides an example viscosity profile, showing that the Rapid Profile Viscometer can be packaged to fulfill the demand characteristics of the particular clinical or laboratory setting, and can be used as, e.g., a compact point of care device for bedside use, or a lab device for commercial application.

Plasma Viscosity

The disclosed technology can be applied to plasma obtained from spinning down a whole blood sample in a centrifuge. Plasma viscosity reflects the amount of reactive proteins in the blood. Thus, plasma viscosity is a measure of the inflammatory response, helpful in detecting and managing the excessive immune response that underlies much COVID-19 pathology. Plasma viscometry can reveal the presence of acute phase reactants; whole blood viscometry can reveal the effects of the acute phase reactants on intravascular flow, especially in slow flow vessels such as the deep veins of the leg.

Coagulometer

In addition, the disclosed technology can be used to objectively measure the physical manifestations of the blood clotting cascade and determine the clotting time by continually measuring the viscosity of a fresh blood sample during coagulation.

The test is performed by repeatedly measuring the viscosity of the same blood sample until coagulation prevents the passage of fluid between the sample container and reservoir. A blood plasma viscosity can use ~1 mL of blood plasma supernatant created by spinning down a small sample of anticoagulated whole blood. The plasma viscosity test can take only 30 seconds to perform, and all components that contact the sample are disposable. Each coagulation test involves a series of viscosity measures (e.g., every 30 seconds) performed on a sample of fresh whole blood to record changes in viscosity during coagulation. The resulting viscosity curve plots the physical cascade of coagulation. In this way, a clinician can determine the coagulation condition of a patient and administer and/or adjust the patient's treatment accordingly.

The Rapid Profile Viscometer has been used to study efficacy of hemodilution for treatment of experimental stroke in dogs, and to study blood viscosity reducing medications for managing human peripheral arterial occlusive disorders such as intermittent claudication. A Point-Of-Care (bedside) version of the Rapid Profile Viscometer is a companion test in the critical care management of anti-inflammatory and anticoagulant treatments for hospitalized COVID-19 patients.

Additional Disclosure—COVID-19 Application

As explained elsewhere herein, infection with COVID-19 (or other pathogens, including other viruses) can result in severe inflammation and intravascular clotting (coagulopathy). In the case of inflammation, the virus can induce extreme reactivity of the immune system leading to production of large quantities of acute reactive proteins including fibrinogen (an important clotting factor), which enter the bloodstream and cause a highly elevated blood viscosity. Unlike blood plasma, whole blood viscosity is shear rate dependent (i.e., the slower the flow, the higher the viscosity) so the highest blood viscosity is usually in the deep veins of the legs where the blood flow is slow. Increased blood viscosity associated with diminished blood flow sets up ideal conditions for intravascular clotting.

As to the viral infection itself, the blood vessel wall has specific receptors for the corona virus that permit the virus to enter and injure the vessel lining (endotheliopathy). These injuries permit intravascular blood clots to form, especially in the slow flow blood vessels. The end result of these interacting inflammatory and coagulopathic pathways can be Venous Thromboembolism (VTE) and/or Disseminated Intravascular Coagulation (DIC), which can lead to widespread embolism. Thus, an elevated shear rate-dependent blood viscosity can generate a vicious cycle, in which the viscosity continually increases as the flow rate decreases, culminating in stasis and intravascular clotting. For these (and other reasons), it is clinically important to monitor blood viscosity, as a tendency toward a thickening of blood (i.e., increased viscosity with decreased flow rate) can result in thrombosis and/or embolism. VTE and DIC are the bane of the COVID-19 patient in the ICU. As a consequence, elevated blood viscosity must be detected before VTE and DIC take place, and appropriate preventive treatments/measures administered to mitigate the risk of embolization and irreversible injury to vital organs.

Pathophysiology

Existing tests for the markers of inflammation (e.g., C-reactive protein, CRP, and the erythrocyte sedimentation rate, ESR) are complex and time-consuming, and are also best performed by trained technicians in a laboratory setting. The disclosed technology provides the novel, non-obvious insight that blood viscosity can measure (or act as a proxy for) the amount of these reactive proteins, and blood viscosity is easily and quickly measured at the bedside using the RPV.

A major cause of Morbidity and Mortality in the ICU is the increase in DIC, venous thromboembolism (VTE) and microvascular thrombi from uncontrolled intravascular clotting and hyperviscosity of blood. At present, neither Whole Blood Viscosity (WBV) nor Plasma Viscosity (PV) are generally utilized in the diagnosis and treatment of COVID-19. For this reason, the disclosed point-of-care ("bedside") WBV and PV test can help mitigate mortality from intravascular blood clotting by enabling timely detection and early management of coagulopathy in ICU patients before damage to vital organs.

It is thought that the morbidity and mortality resulting from COVID-19 is as much a consequence of the body's over-response to the virus as it is due to the tissue injury directly caused by the virus. The immune over-response to SARS-CoV-2 can cause acute respiratory distress syndrome (ARDS), Disseminated Intravascular Coagulation (DIC), "cytokine storm", immuno-thrombosis, multiple organ failure, and death. Therefore, current empirical treatment for COVID-19 is directed to diminishing this excessive immune response. A convenient companion test is needed to monitor the efficacy of these therapeutic interventions on blood viscosity. The disclosed RPV devices and methods provide an objective measure.

Increased thrombogenicity also plays an important role in the pathophysiology of severe COVID-19 disease. Empirical treatment for COVID-19 depends on anticoagulants to decrease susceptibility to intravascular clotting. This approach may not be effective. In any event, the thrombogenicity is accentuated by elevated blood viscosity (due to excessive acute phase reactants produced as part of the immune over-response to the virus) and further compounded by direct viral injury to the vascular intima. A convenient companion test is needed to monitor the efficacy of the therapeutic interventions for coagulopathy. The RPV can also serve as a bedside Coagulometer.

COVID-19 Treatment

At present, venous thromboembolism (VTE) prevention and treatment with unfractionated heparin (UH) and low molecular weight heparin (LMWH) provides mixed results in treating thrombotic complications of COVID-19. Multiple trials are currently underway to determine the effectiveness of UH and LMWH in COVID-19 treatment. Alternative novel anticoagulants are also being studied.

Measures of whole blood viscosity (WBV) and plasma viscosity (PV) reflect elevation in acute phase reactants produced during COVID-19 disease. However, C-reactive protein (CRP) and fibrinogen levels are not significantly improved by the use of heparin. Also, elevated whole blood viscosity (WBV) predisposes the patient to VTE and microthrombosis despite heparin use. Further, elevated plasma viscosity (PV) and measures of disease severity, such as Sequential Organ Failure Assessment (SOFA) scores, are highly correlated. A number of studies have demonstrated that the amount of acute phase reactants in the blood correlates highly with morbidity and mortality in COVID-19.

SARS-CoV-2 infection of vascular endothelial cells leads to their destruction. This endotheliopathy leads, in turn, to excessive platelet activation predisposing the patient to the coagulative DIC—a serious complication of COVID-19 disease. Heparins do not address this excessive platelet activation.

Role of Viscometry in COVID-19

A study of 15 critically ill COVID-19 patients found that all had blood plasma viscosity (PV) levels 95% or more above the normal range (1.4-1.8 centipoise), and of the 4 patients with a PV of 3.5 centipoise or greater, all had venous thromboembolism (VTE). D-dimer levels are used to monitor the severity of the activation of the coagulation cascade, and elevated D-dimer levels in COVID-19 are associated with poor prognosis. The Rapid Profile Viscometer (RPV) can measure both PV and WBV. It can record the viscosity profile of a fresh or anticoagulated whole blood sample at bedside in less than 60 seconds and also serve as a bedside test to measure coagulation. Whole blood viscosity is superior to PV in that the viscosity profile better reflects the actual shear rate dependent blood flow conditions existing in vivo, especially the increased resistance to flow in the low flow vasculature (such as deep veins of the leg) where VTE is most prevalent.

Heparin may not be adequate to prevent the VTE and micro thrombotic complications of COVID-19. "Timing is everything": the elevated D-dimer is from clot lysis ("clot breaking up") which occurs later in the disease process than the increase in whole blood viscosity (WBV) and plasma viscosity (PV) which take place early on in the disease. Increased viscosity is caused by the elevated fibrinogen and other acute phase reactants prior to clot formation. If the elevated viscosity is detected early enough, it will be possible to employ preventive interventions.

Early and repeated measures of WBV and PV will be helpful in guiding treatment needed to suppress the coagulation cascade—use of alternative anticoagulants —apixaban, fondaparinux and GP IIb/IIIa inhibitors, or the use of plasma exchange (a classic modality for the treatment of hyperviscosity). These promising treatments are under investigation in ongoing clinical trials.

Point-of-care (POC) fresh whole blood viscometry (WBV) provides real-time information regarding the state of blood flow and the potential for in vivo intravascular clotting. These situations will benefit from immediate timely information to guide preventive measures and medical management of abnormal blood clotting.

POC blood plasma viscometry (PV) provides real time information regarding the level of acute phase reactants. These situations will also benefit from immediate timely information to guide medical management of severe inflammatory disorders.

POC measures of coagulation provide real-time information about the physical manifestation of the coagulation cascade in situations that benefit from immediate timely information to guide medical management of abnormal blood clotting.

Summary of Recent Findings

There is growing evidence that the flow properties of blood in the macrocirculation play a key role in the pathogenesis of COVID-19. In particular, the high volume of acute phase reactants (such as fibrinogen) entering the bloodstream because of the intense viral inflammation significantly increases blood viscosity, especially in the slow flow vasculature. Elevated low shear rate viscosity plus viral vasculitis can lead to hemostasis and intravascular clotting in the deep veins of the leg. Decreased blood flow combined with widespread viral injury to the vascular intima create conditions conducive to vascular microthrombosis, the bane of the COVID-19 ICU patient. A blood viscosity test can be the key to early detection of impending viral coagulopathy and create opportunity for preventive intervention and convenient monitoring of response to treatment.

While COVID-19, caused by the SARS-CoV-2 virus, usually presents with symptoms of viral upper respiratory infection such as fever, headache, dry cough, and muscle aches, much of the morbidity and mortality resulting from the illness is the consequence of a severe generalized inflammation and coagulopathy. There are many biological markers that are found in severe COVID-19 disease including leukocytosis, lymphopenia, and elevated C-reactive protein (CRP), ferritin, IL-6 (suggestive of severe inflammation) D-dimer (suggestive of clot lysis) and LDH.

One study found that the incidence of symptomatic venous thromboembolism is approximately 6% in hospitalized COVID-19 patients but is approximately 24% in those requiring higher levels of care. Another study of patients with mild-to-moderate COVID-19 (using CT pulmonary angiography and CT venography) found asymptomatic venous thromboembolism in approximately 83% of those screened for clots. A study of over 300 post-mortem COVID-19 patients conducted by pathologists observed a 91% incidence of micro-thrombosis at autopsy.

Based on studies reported to date, it can be helpful to remove the excess volume of acute phase reactants and the excess coagulopathic proteins that contribute to increased blood viscosity and intravascular clotting. Therapeutic plasma exchange (TPE) is an accepted treatment for hyperviscosity syndromes. TPE is currently being studied as a method of treatment for hyperviscosity associated with severe COVID-19. As yet, they have not collected enough data from clinical trials to determine whether TPE can have outcome related benefits in severe COVID-19. However, early results show TPE reduces plasma viscosity and decreases IL-6, CRP, fibrinogen, D-dimer, and ferritin levels (biochemical factors associated with more severe COVID-19) and normalizes PaO2 and FiO2 levels (demonstrating an improvement in lung function). These results suggest that replacing COVID-19 affected plasma with healthy fresh frozen plasma can cause reductions in the markers of inflammation and coagulopathy that are associated with the morbidity and mortality seen in severe COVID-19. It is also possible that earlier intervention with TPE may prevent the severe manifestations. While CRP and D-dimer are biochemical markers that can show presence of severe COVID-19 disease, an elevation in whole blood or plasma viscosity is an early biophysical marker that can help to predict the severity of COVID-19 as well as be an early manifestation of the intense immune response (cytokine storm) and the coagulopathy (disseminated thromboembolism) that foretell a poor outcome in severe COVID-19.

As explained elsewhere herein, the disclosed RPV can help to identify patients at risk and measure treatment response of those patients who are likely to develop severe COVID-19. The RPV can distinguish patients who may benefit most from treatments such as early therapeutic anticoagulation, a variety of anti-inflammatory treatments, and/or therapeutic plasma exchange. Because much remains unanswered regarding if and at what point to implement these treatments, applying blood viscometry in COVID-19 can also play a role in developing the guidelines for these therapies. Possibly, the most important contribution of viscometry in COVID-19 will be the ability to predict the likely severity of inflammation and coagulopathy prior to irreversible organ damage. In contrast, usual markers such as elevated D-dimer levels inform the intensivist that the irreversible damage caused by coagulopathy (DIC) may already be present.

Recent studies suggest that intervention (such as prophylactic therapeutic anticoagulation or the monoclonal antibody drug directed at GM-CSF, lenzilumab) during moderate early disease, before cytokine storm, ARDS, and coagulopathy have set in, has been more effective at producing improved outcomes such as decreased overall mortality and survivability without ventilation suggesting the possibility that earlier preventive interventions may be of greater value as opposed to waiting to intervene once the disease has become severe. The latest research also indicates that (1) Whole blood viscosity on admission in COVID-19 is higher in fatal disease than in non-fatal disease; (2) microthrombosis and venous thromboembolism (VTE) are different types of clots and clinically distinct phenomena explaining the difference in the incidence of microthrombosis and VTE in other studies, and (3) a scoping review has found a high probability that therapeutic plasma exchange would be beneficial in treating the cytokine storm in severe disease. In a study investigating the effect of TPE on outcomes in severe COVID-19, the results of 43 ICU patients randomized to TPE plus standard treatment vs. 44 ICU patients with standard treatment only found that duration of mechanical ventilation, duration of ICU stay, and SOFA scores were significantly reduced in the TPE group. While the difference in 35 day mortality was deemed non-significant, the results of 20.9% for TPE vs. 34.1% for no TPE were noteworthy and suggest the need for further investigation. Finally, another retrospective propensity-score matched study of 90 patients assigned to two equal groups found that 28 day survival was significantly higher in the TPE group (91.1%) vs. controls (61.5%), p<0.001 and that in the TPE group where TPE was performed before day 12 of hospitalization there was a 0% mortality. Thus, a POC test that can detect elevated volumes of acute phase reactants and indicators of coagulopathy earlier in the disease (such as whole blood viscosity) can help guide therapy (possibly TPE) that would decrease morbidity and improve survivability in COVID-19 disease.

In the management of COVID-19, time is of the essence. Early detection of coagulopathy with timely intervention can save lives and avoid post COVID invalidism. Current biochemical markers of inflammation and coagulopathy have not proven as helpful as required to defeat this agile and deceptive virus, and a test is needed that can serve as a "leading indicator" that can predict the likelihood of organ damage. For example, the D-dimer usually reveals the presence of coagulopathic injury after the fact, when disseminated clots and emboli are already undergoing lysis. The intensivist needs markers that predict the future, early indicators that provide time for preventive interventions that protect vital organs from injury.

In meeting these needs, the disclosed RPV is a practical tool for the intensivist to track the rheological and clotting characteristics of blood in the macro-vasculature, and to monitor the biophysical response to treatments for the hyperviscosity of blood associated with severe inflammation, and the intravascular clotting of blood associated with hypercoagulability. The RPV is a convenient lab or bedside whole blood viscometer, plasma viscometer, and/or coagulometer that can detect and track the biophysical changes that serve as a proxy for the early biochemical changes associated with severe inflammation and coagulopathy caused by COVID-19, among other pathogens.

Summary

RPV quickly measures the magnitude of the immune response—any increase in acute phase reactants increases both whole blood and plasma viscosity, but blood viscosity (unlike plasma viscosity) is flow rate dependent. Therefore, the Rapid Profile Viscometer provides information about the varying degrees of resistance to flow that blood experiences in various parts of the vasculature, as for example, highly elevated viscosity in slow flow vessels such as the deep veins of the leg where a combination of injury to the vascular endothelium from the virus plus near stasis flow due to elevated acute phase reactants can result in VTE and DIC. Other blood tests for inflammation are complex and time consuming. Therefore, C-Reactive Protein (CRP) and Erythrocyte Sedimentation Rate (ESR) are not convenient or adequately informative as POC tests. Whole Blood viscosity (WBV) and Plasma viscosity (PV) are POC tests that can measure the physical effects of reactive proteins on blood flow—and whole blood viscosity is especially easy to perform at the bedside (i.e., no centrifuge is required) to quickly (i.e., takes less than a minute) determine the viscosity profile to detect elevated low shear rate viscosity and monitor response to treatment. The disclosed technology can serve as, inter alia, a whole blood viscometer, a blood plasma viscometer, and a blood coagulometer.

As shown and explained herein, the disclosed technology can comprise a device that uses disposables that contain a blood sample which is loaded into a reservoir area within a reservoir. A reservoir can be a syringe that also serves as the pump (air pulse generator) that draws up a sample to generate a negative pressure curve and then expels the sample to generate a positive pressure curve. The positive and negative curves can be averaged to cancel out the hydrostatic, diabatic, cohesive/adhesive and atmospheric pressure errors that afflict most conventional capillary viscometers. It should be understood, however, that averaging is not a requirement, as a single pressure vs. time curve can suffice. Serial curves performed (e.g., every 30 seconds) with fresh whole blood samples can be used to measure coagulopathy (coagulometer function), and/or anticoagulated blood samples can be spun down and plasma viscosity measured. Thus, the disclosed technology provides multi-function devices.

The circulatory system is a vital component of good health. It serves as the means of transport for blood which allows for the absorption of nutrients and removal of waste. For this reason, the flow of blood has been a focus of research for centuries and its malfunction has been determined to be the root cause of many medical conditions. The properties of this bodily fluid are distinct due to its constituents and therefore one must fully understand the elements of blood in order to predict its rheological behavior.

The basis of our experiment revolves around the fundamentals of fluid dynamics. A fundamental concept that is used to characterize liquids in rheology is the resistance of a fluid to flow, which is known as viscosity. A French scientist in the early 19th century by the name of Jean Léonard Marie Poiseuille derived an equation which incorporated viscosity to describe the flow of a fluid in his attempt to understand blood flow. Poiseuille's law states:

$$\Delta p = \frac{8\mu L Q}{\pi R^4}$$

Where $\Delta p$ is the pressure difference between the ends of the conduit, $\mu$ is the dynamic viscosity, L is the length of the conduit, Q is the volumetric flow rate, and R is the conduit radius.

Therefore, by knowing the pressure difference along a given tube with known dimensions one can determine the viscosity of any given fluid flowing through that tube. When comparing viscosity versus shear rate, which is the rate at which fluid layers move past each other, one can notice that viscosity is not constant during blood flow.

The disclosed technology thus presents significant value to a number of stakeholders. To the medical community, the disclosed technology presents a device to diagnose elevated inflammation and clotting in the blood vessels of severely ill COVID-19 patients, as well as an opportunity for early detection and more effective management to save lives. To patients, the technology provides a non-painful test to aid doctors in diagnosis and treatment of what can be a life-or-death condition, which can in turn improve chances of survival in the ICU.

Figures

Method for eliminating hydrostatic, diabatic, atmospheric, adhesive, and cohesive errors. Generate a negative pulse. Generate a positive pulse. Take both time-pressure curves, slice equivalent T-P segments, flip one T-P segment, average resulting T-P segments to eliminate errors related to direction of flow. Permits development of a quick, simple, safe, portable, low cost and disposable precision viscometer suitable for bedside use (POC) as well as in the clinical laboratory.

FIG. 1 provides a depiction of the role of blood viscosity in intravascular coagulopathy. As shown, any general injury (e.g., trauma, infection) to the vascular endothelium can provoke an inflammatory response (vasculitis), causing production of acute phase reactive proteins which in turn gives rise to an elevated blood viscosity, especially in the low flow vasculature. The elevated viscosity in turn causes a decreased blood flow, (and can even create a vicious cycle leading to stasis.) The decreased blood flow combined with local vascular injury can create the conditions that ultimately give rise to intravascular clotting, which can lead to VTE and DIC with serious or even fatal consequences.

Figure 2:
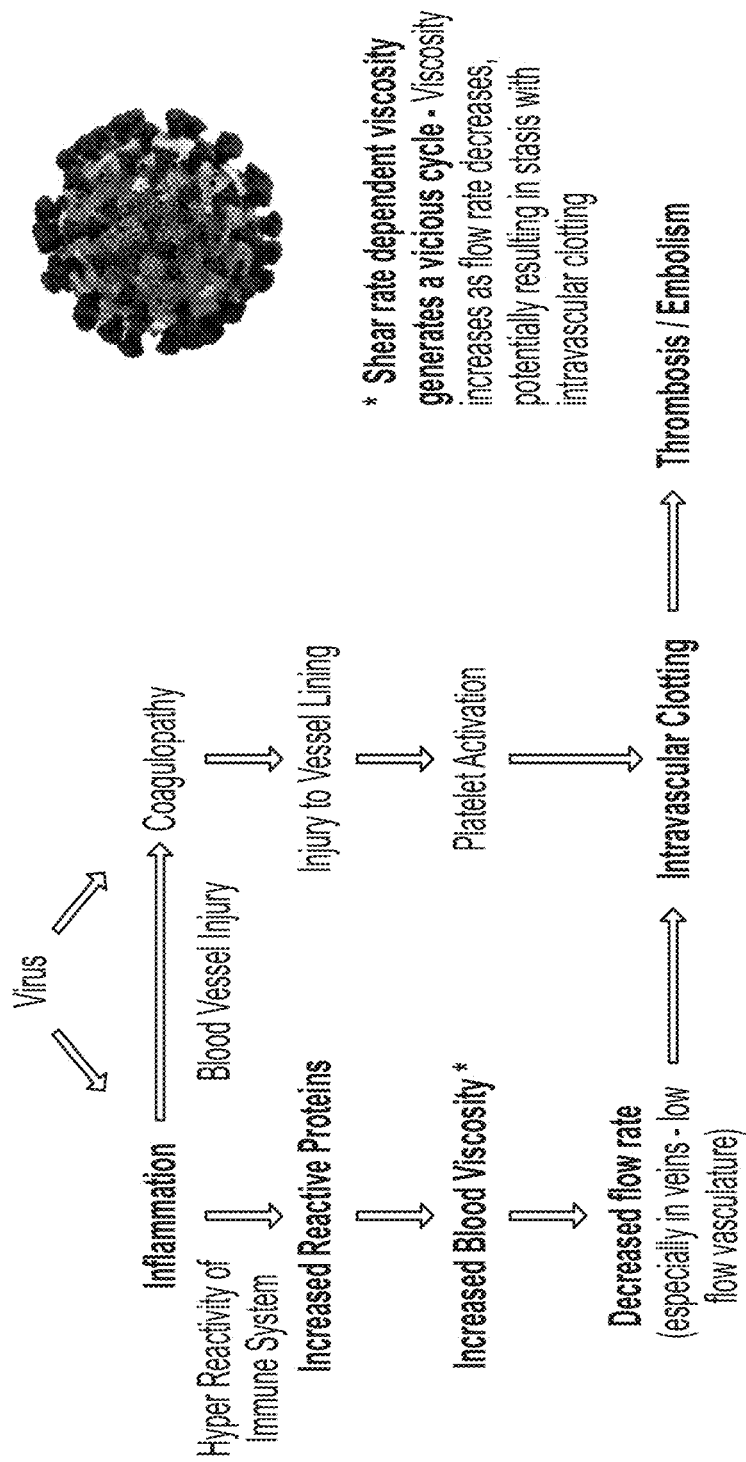
FIG. 2 provides a proposed mechanism for the effect of inflammation (e.g., inflammation caused by the COVID-19 virus) on blood viscosity and clot formation.

FIG. 2 provides a proposed mechanism for the effect of inflammation (e.g., as caused by the COVID-19 virus) on blood viscosity and clot formation. Similar to FIG. 1, FIG. 2 illustrates pathways by which intravascular clotting can occur, and ultimately cause venous thromboembolism (VTE) and disseminated intravascular coagulation (DIC) leading to disseminated embolism with failure of vital organs.

FIG. 3 provides an illustration of the process of first order decay in a dashpot system according to FIG. 4. As explained, the decrease in spring tension can take place according to first order decay, and the rate of tension at any instant can depend on the viscosity of the fluid under study.

FIG. 4 provides an illustration of a spring engaged with a dashpot piston.

FIG. 5 provides an illustration of the principle of operation of the disclosed devices. As shown, an air pressure pulse (or an air withdrawal) can move blood within the reservoir (shown containing blood below a headspace of air) and also within a capillary in fluid communication with the reservoir. The air in the headspace of the reservoir acts like the spring in the system shown in FIG. 4, and the blood-filled capillary acts as a dashpot.

FIG. 6 provides an illustration of a viscosity vs. shear rate profile for an exemplary fluid. As shown, viscosity can vary as a function of shear rate.

Figure 7:
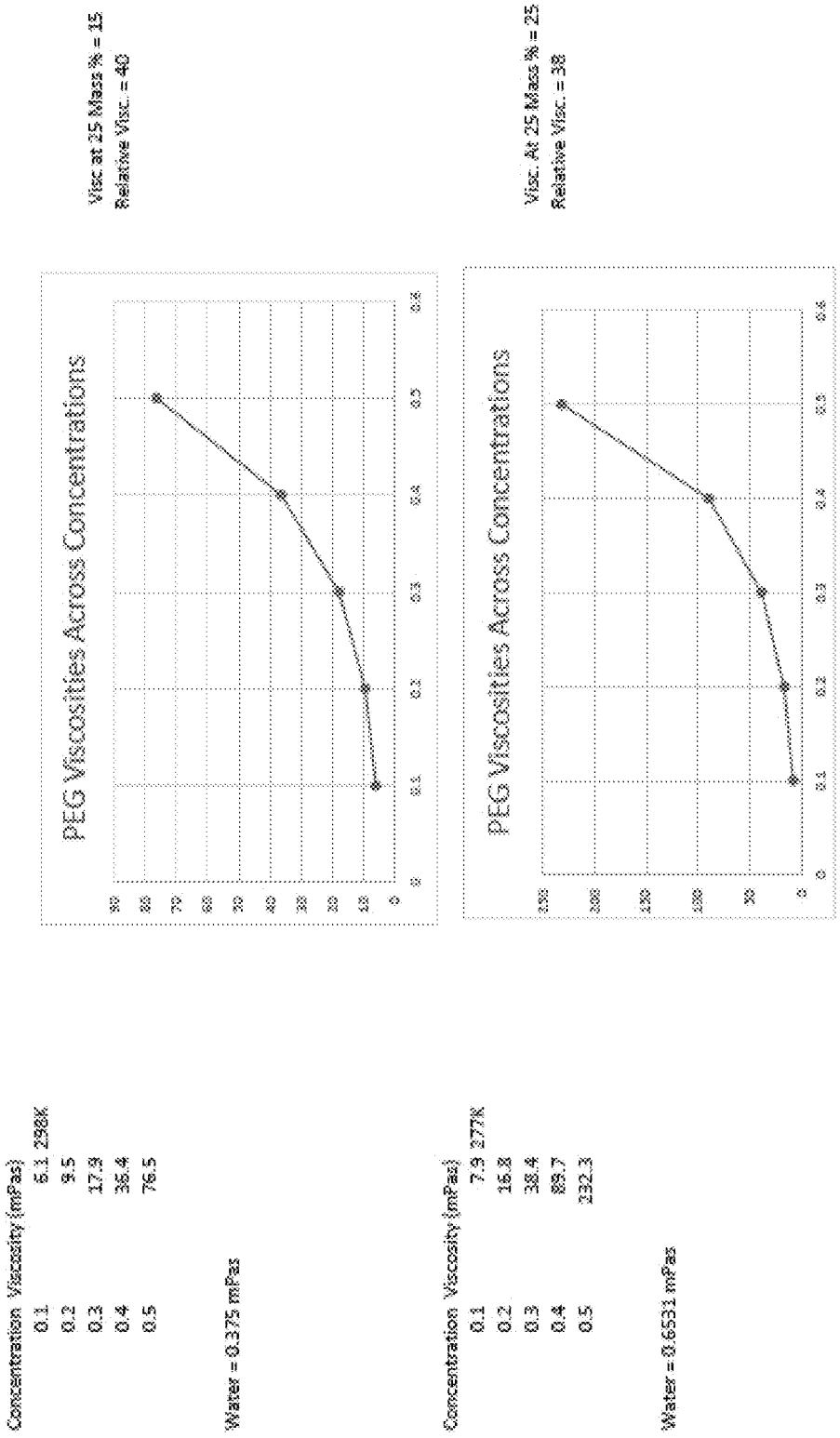
FIG. 7 provides exemplary viscosity vs. concentration data for illustrative PEG samples.

FIG. 7 provides exemplary viscosity vs. concentration data (gathered according to the present disclosure) for illustrative PEG (polyethylene glycol) samples. As shown, the viscosity increased with increasing PEG concentration. The study in FIG. 7 was designed to test the value of "relative viscosity" (comparison of viscosity of a solution or fluid mixture to the viscosity of the solvent) versus the calculated viscosity per Hagen-Poiseuille Law which depends upon the dimensions of the conduit (e.g., capillary length and diameter). Two different sized hypodermic needles were used in this experiment, and calculation came up with very different viscosities, However, the relative viscosities (PEG relative to water) were essentially the same (i.e., 38 vs. 40). Thus, relative viscosity was used in calculations of resistance to flow.

Figure 8:
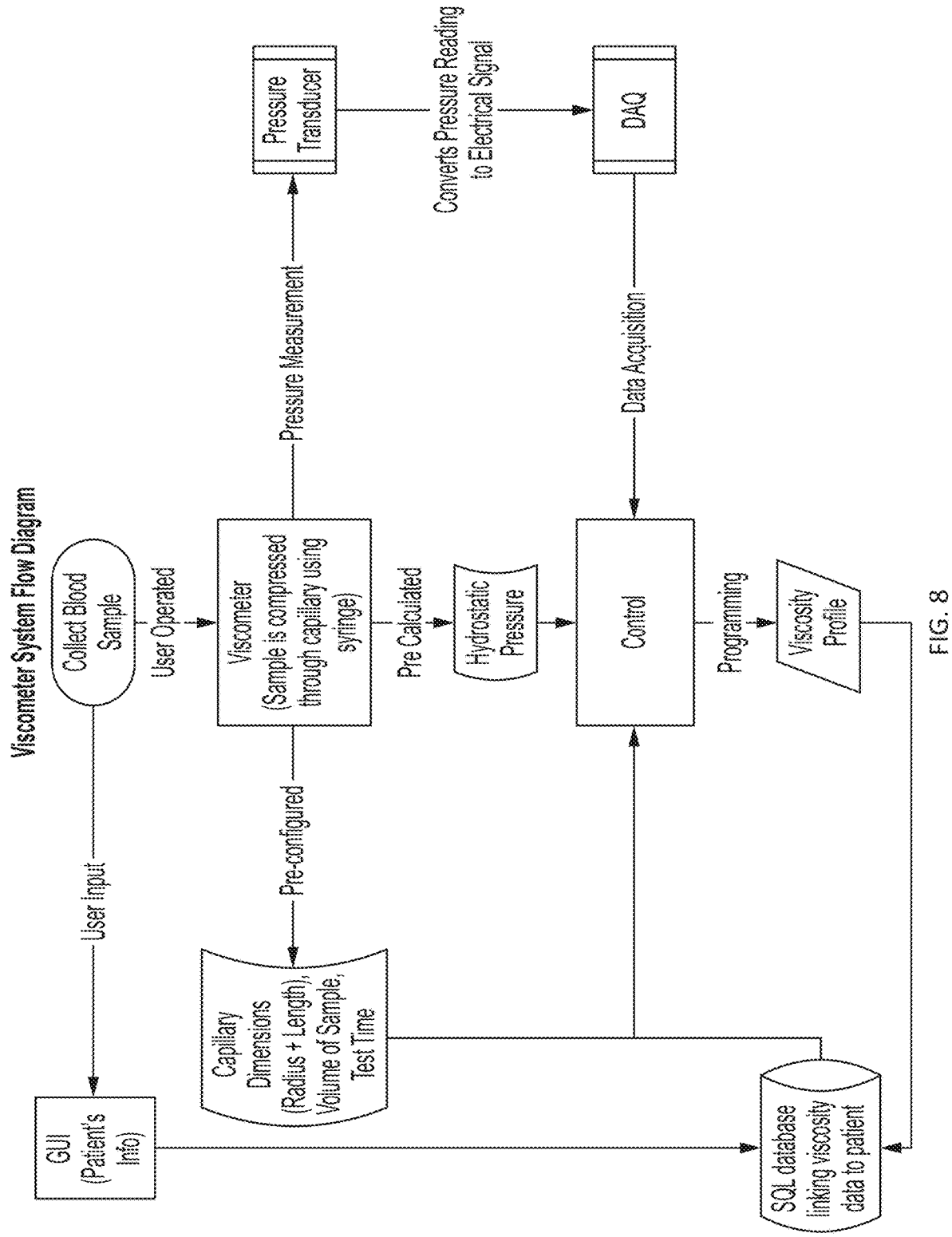
FIG. 8 provides an exemplary control flow for a viscometer system according to the present disclosure.

FIG. 8 provides an exemplary control flow for a viscometer system according to the present disclosure. As shown, a blood (or other) sample is collected and is processed by a viscometer. The viscometer can be manually operated, but this is not a requirement, as the viscometer can be operated in an automated fashion. The sample can be communicated into (or out of) a reservoir, and the pressure within the reservoir during the communication is monitored as a function of time, e.g., via a pressure transducer that converts a pressure reading into an electrical signal that is provided to a DAQ module. The system can then determine a viscosity profile (e.g., viscosity as a function of shear rate) for the fluid under study, e.g., based on the fluid's flow through the capillary. The system can accomplish this by, e.g., application of the Hagen-Poiseuille equation, to obtain a viscosity value when other system parameters (pressure, capillary radius, capillary length, and the like) are known. Laminar flow within the capillary is considered suitable but is not an absolute requirement.

Figure 9:
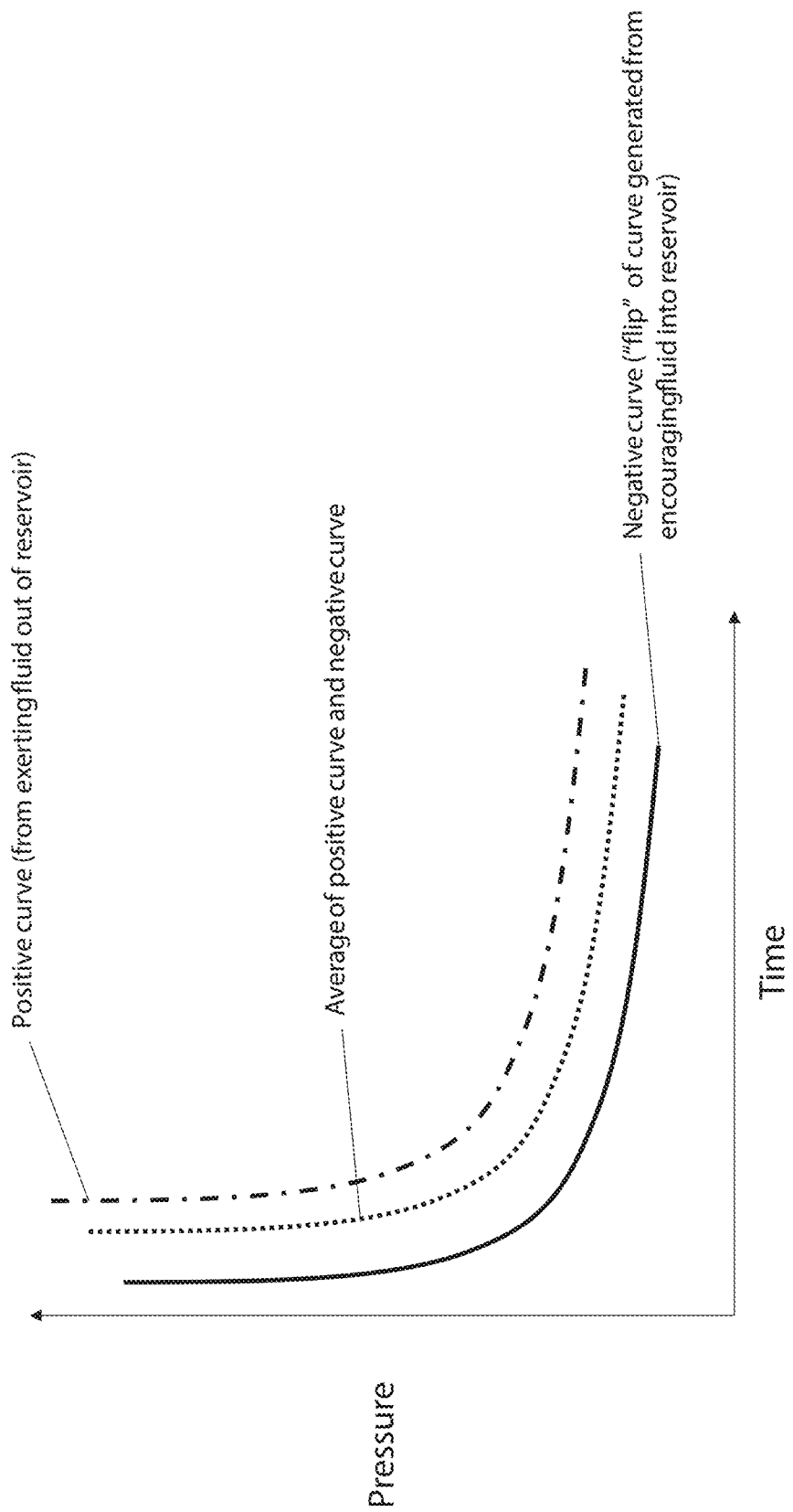
FIG. 9 provides an exemplary pressure vs. time curves. For processing (e.g., averaging), the curves can have the same starting pressure and the same time duration, thereby allowing a user to compare the curves' values at a given time (e.g., at 1.5 seconds following the application of a pulse that encourages fluid into or out of a reservoir). As explained elsewhere herein, the "positive" curve can be the data resulting from exerting a fluid out of a reservoir, and the "negative" curve can be the data resulting from encouraging the fluid into the reservoir, e.g., by giving rise to a reduced pressure within the reservoir that draws the fluid into the reservoir. A user (or a system or method according to the present disclosure) can flip one of the curves (axis-wise) so that the two curves are in the same quadrant of the pressure vs. time axes, thereby allowing for simplified averaging of the two curves.

FIG. 9 provides exemplary pressure vs. time curves. For processing (e.g., averaging), the curves can have the same starting pressure and the same time duration, thereby allowing a user to compare the curves' values at a given time (e.g., at 1.5 seconds following the application of a pulse that encourages fluid into or out of a reservoir). As explained elsewhere herein, the "positive" curve can be the data resulting from exerting a fluid out of a reservoir, and the "negative" curve can be the data resulting from encouraging the fluid into the reservoir, e.g., by giving rise to a reduced pressure within the reservoir that draws the fluid into the reservoir. A user (or a system or method according to the present disclosure) can flip one of the curves (axis-wise) so that the two curves reside in the same quadrant of the pressure vs. time axes, thereby allowing for simplified averaging of the two curves. Without being bound to any particular theory or embodiment, curves being averaged together can have the same starting pressure and the same time duration; this facilitates comparing the curves and averaging the data.

Figure 10:
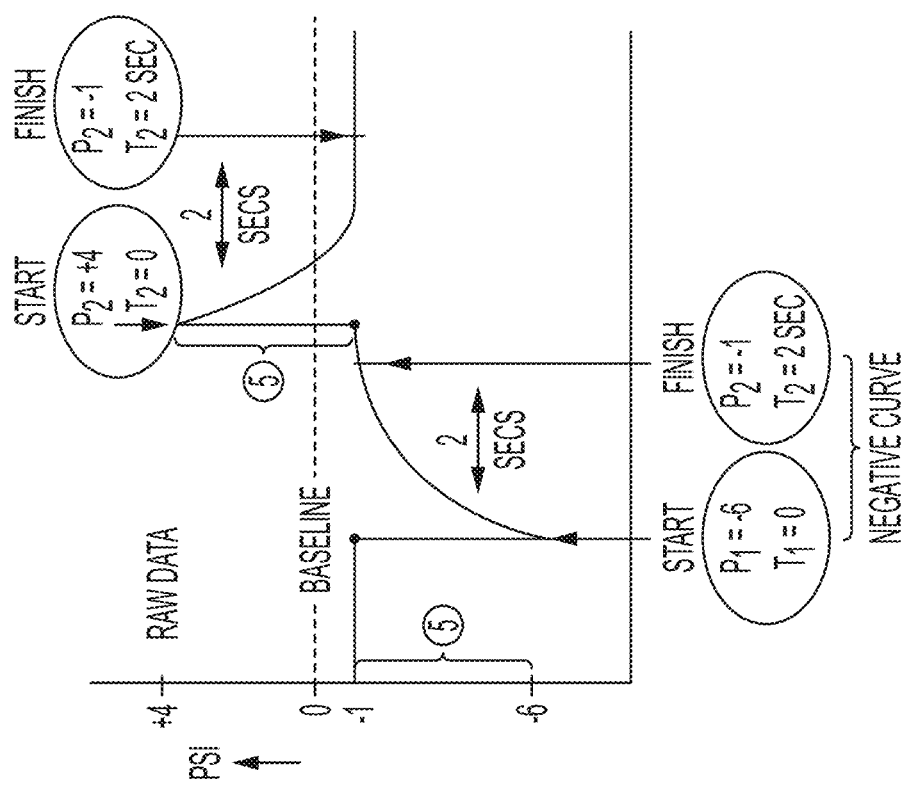
FIG. 10 provides an illustration of example data obtainable by the disclosed technology, showing a negative curve (showing pressure vs. time data evolved by encouraging fluid into a pressure-monitored reservoir by effecting a reduced pressure within the reservoir that draws the fluid into the reservoir) and a positive curve (showing pressure vs. time data evolved by exerting fluid out of the reservoir).

FIG. 10 provides an illustration of example data obtainable by the disclosed technology, showing a negative curve (showing pressure vs. time data evolved by encouraging fluid into a pressure-monitored reservoir by effecting a reduced pressure within the reservoir that draws the fluid into the reservoir) and a positive curve (showing pressure vs. time data evolved by exerting fluid out of the reservoir). The two curves are sliced to collect equivalent data (e.g., duration and magnitude independent of polarity) from both the negative and positive curves. The curves are superimposed independent of baseline offset, and averaged to cancel out the hydrostatic, adhesive/cohesive, diabatic, offset and other errors that are based on the geometry of the device (e.g., a vertical Vacutainer, capillary and reservoir that create a varying hydrostatic pressure during filling and emptying.) The convenience of performing the test using this simple design more than compensates for the small additional time (about 60 seconds) to perform both the negative and the positive tests plus the computerized manipulation of the data (inverting and averaging the data) required to achieve greater accuracy and precision of the results. However, single ended tests (only about 30 seconds) may be adequate for screening purposes. In higher precision testing the multiple small errors are compensated by averaging the magnitude of the positive and negative curves after inverting one or the other. To calculate the relative viscosity of the samples, results of either the single ended screening test, or the more precise method are compared directly to the results from testing the control solvent (e.g., water or a standardized PEG solution) performed under the same conditions. The control tests will be performed as frequently as needed to assure consistently valid test results. At minimum, three times daily, in the am, noon and the pm. Criteria for accuracy and precision will be determined by the clinical lab.

Figure 11:
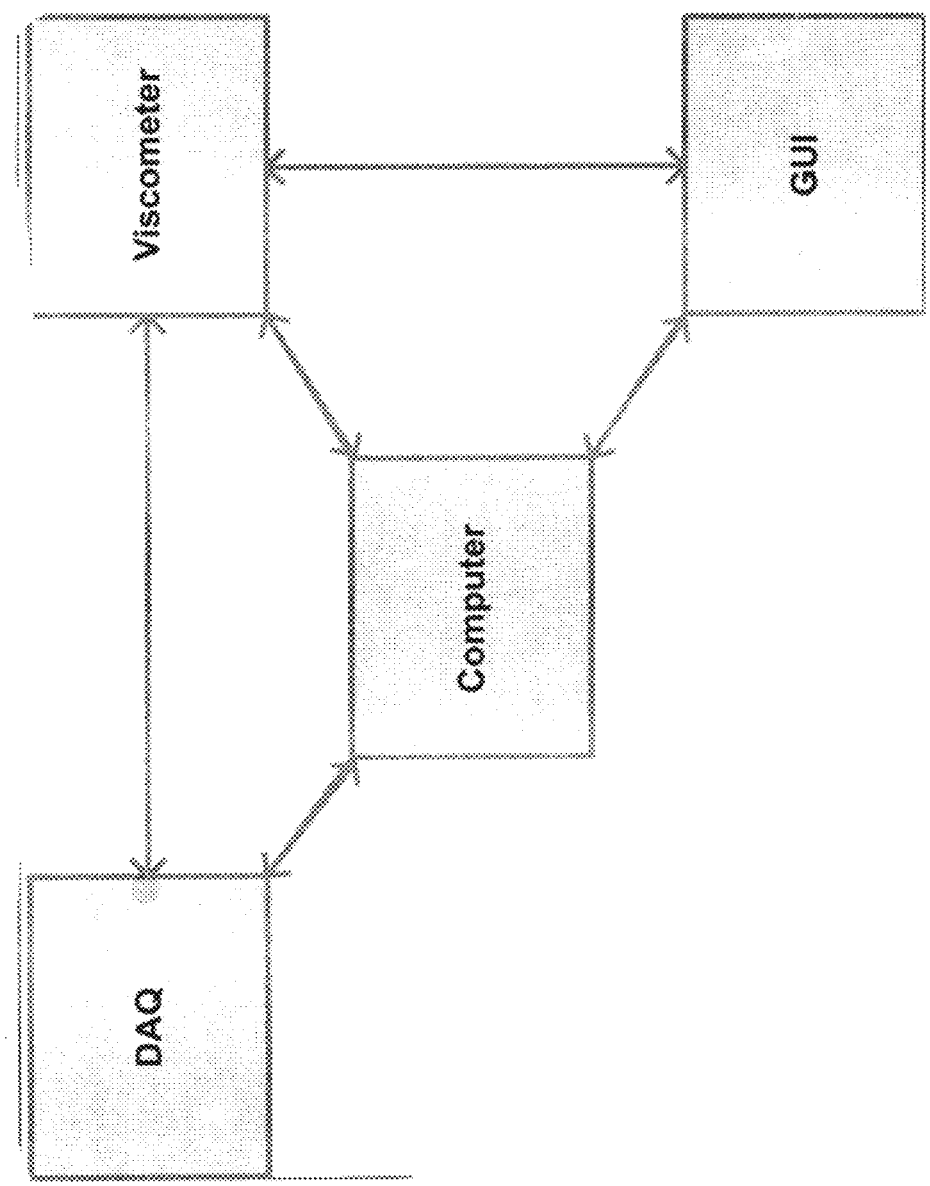
FIG. 11 provides an example control flow for a system according to the present disclosure. As shown, a data acquisition module (DAQ) can be in communication with a viscometer and a computer, with a graphical user interface (GUI) interacting with the viscometer and computer.

FIG. 11 provides an example control flow for a system according to the present disclosure. As shown, a data acquisition module (DAQ) can be in communication with a viscometer and a computer, with a graphical user interface (GUI) interacting with the viscometer and computer.

Figure 12:
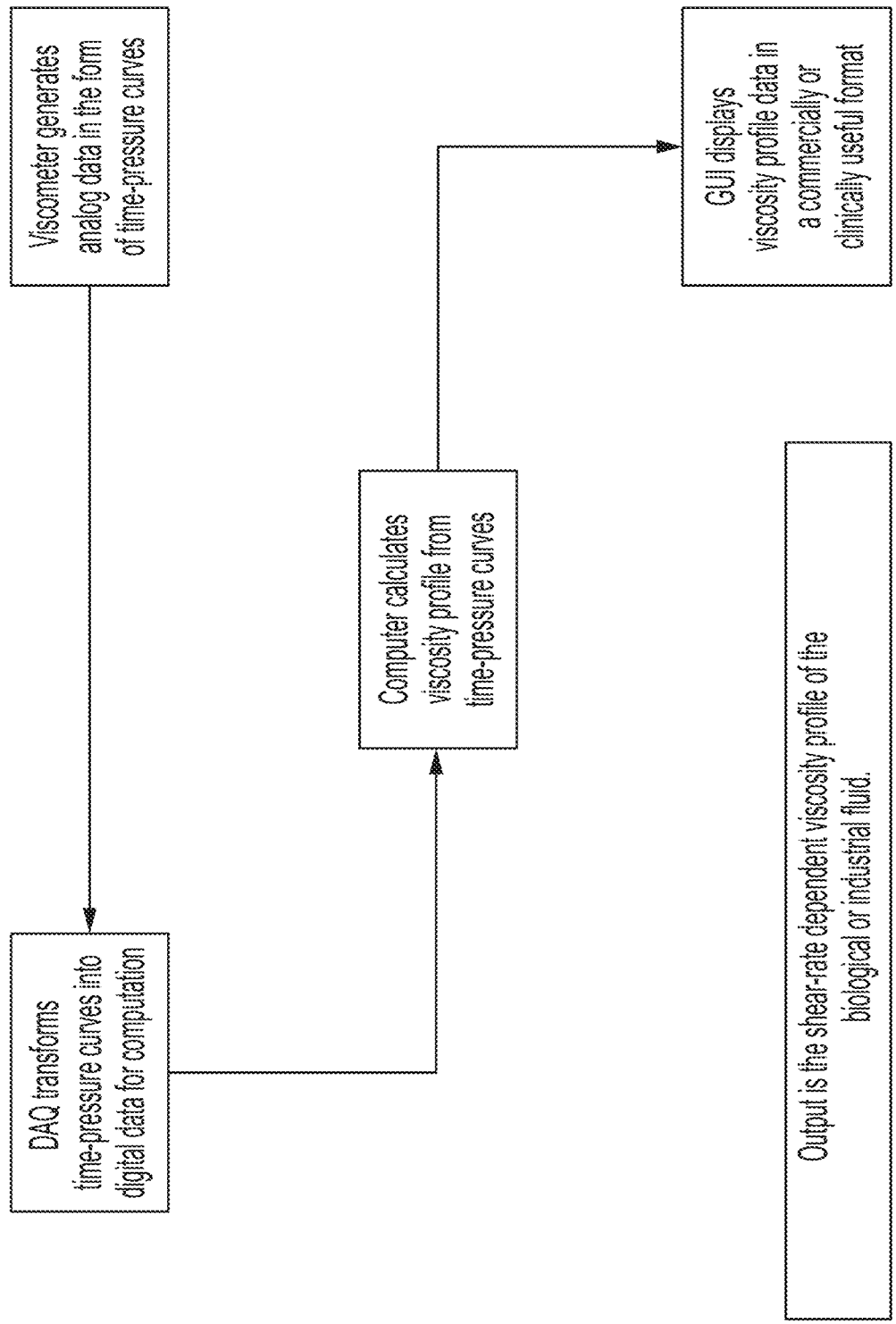
FIG. 12 provides another example control flow for a system according to the present disclosure. As shown, a viscometer (which can comprise a pressure transducer) can generate data in the form of pressure vs. time curves. A DAQ can transform the curves into digital data. The digital data is in turn processed by a processor or processors (e.g., comprised within a computer), which can generate one or more viscosity profiles from the digital data. A GUI can in turn display the viscosity profile in one or more formats.

FIG. 12 provides another example control flow for a system according to the present disclosure. As shown, a viscometer (which can comprise a pressure transducer) can generate data in the form of pressure vs. time curves. A DAQ can transform the curves into digital data. The digital data is in turn processed by a processor or processors (e.g., comprised within a computer), which can generate one or more viscosity profiles from the digital data. A GUI can in turn display the viscosity profile in one or more formats.

Figure 13:
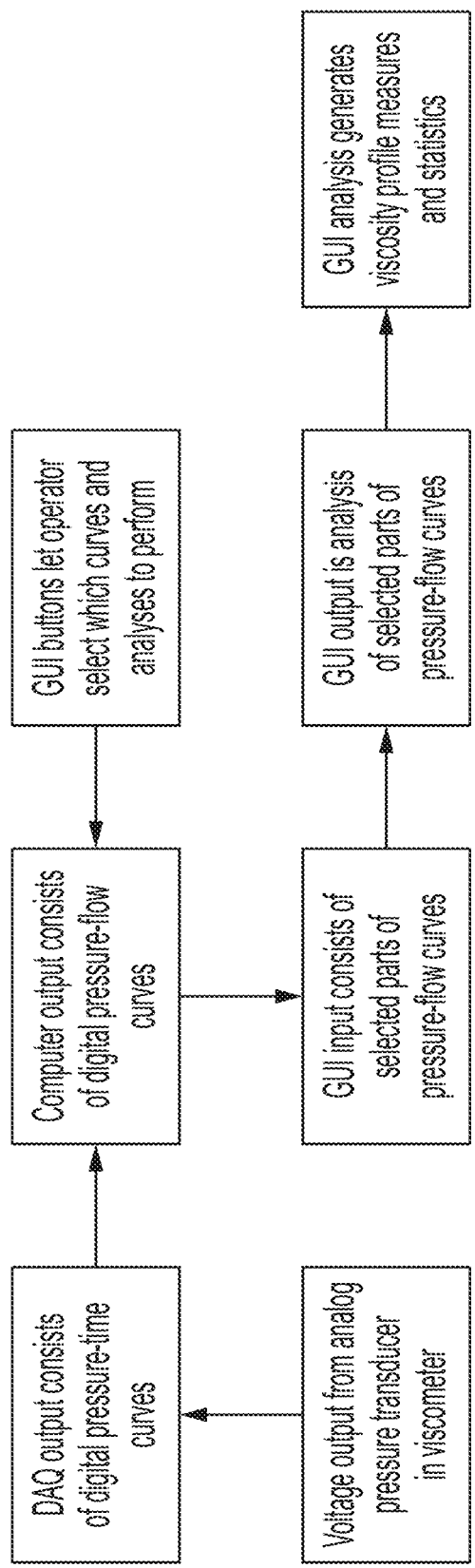
FIG. 13 provides a further exemplary control flow for a system according to the present disclosure.

FIG. 13 provides a further exemplary control flow for a system according to the present disclosure. As shown, a viscometer (which can comprise, e.g., a reservoir, a capillary, and a pressure transducer in communication with the reservoir) can generate analog data in the form of time-pressure curves. A DAQ can transform these curves into digital data for further computation, which computation can be performed by the processor or processors of a computer. This computation can in turn give rise to a viscosity profile (e.g., viscosity vs. shear rate) from the previously-obtained time-pressure curves. A GUI (graphical user interface) can then display the viscosity profile in a useful format. The system can be configured (e.g., via instructions executed on a processor) to classify a given sample. For example, if a subject's blood viscosity profile were suggestive of an inflammatory condition, the system can "flag" that subject's sample for the user's further attention. Likewise, if a subject's blood viscosity profile were suggestive of good health, the system can similarly "flag" that subject's sample. In this way, a system can generate viscosity profiles for subjects, and can also classify such profiles for further attention as appropriate. A system can also monitor changes (or consistencies) between a given subject's viscosity profiles over time (i.e., by comparing profiles obtained at different points in time, such as before and after administration of a treatment). In this way, the disclosed technology can provide the user with clinically relevant data, which data can allow a user to track a subject's progress over time, thereby allowing for administration of appropriate therapies, depending on the patient's condition.

Figure 14:
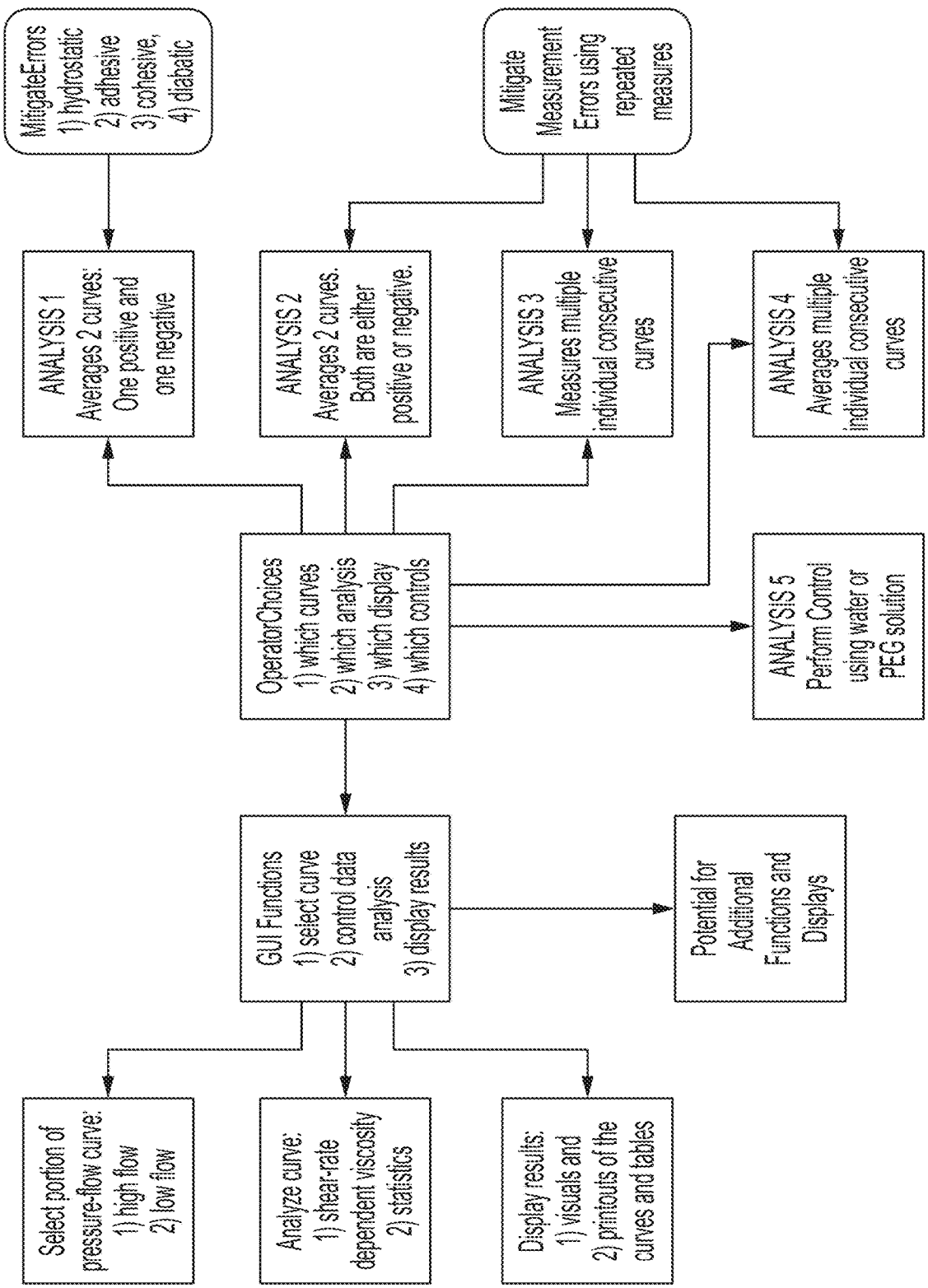
FIG. 14 provides a further exemplary control flow for a system according to the present disclosure.

FIG. 14 provides a further exemplary control flow for a system according to the present disclosure. As shown, a pressure transducer can output a voltage signal, which voltage is then converted to pressure-time curves by a DAQ. The DAQ in turn communicates such curves to a computer or other processing device (which device can even be a mobile computing device). A user can select certain parts of the pressure-time curves for analysis, e.g., the portions of the curves that correspond to certain physiological conditions, such as the pressures and/or flow rates expected in certain blood vessels of the patient.

For example, one can analyze (e.g., via selection) a portion of a curve that corresponds to pressures of 120 mm Hg to 0 mm Hg, from 110 mm Hg to 0 mm Hg, from 100 mm Hg to 0 mm Hg, from 90 mm Hg to 0 mm Hg, from 80 mm Hg to 0 mm Hg, from 70 mm Hg to 60 mm Hg to 0 mm Hg, from 50 mm Hg to 0 mm Hg, from 40 mm Hg to 30 mm Hg, from 30 mm Hg to 0 mm Hg, from 20 mm Hg to 0 mm Hg, from 10 mm Hg to 0 mm Hg, or even from 5 mm Hg to 0 mm Hg. All intermediate ranges can also be used, e.g., from 50 mm Hg to 10 mm Hg, from 40 mm Hg to 20 mm Hg, or even from 35 mm Hg to 30 mm Hg.

Arterial blood flow velocities can be, e.g., in the range of from, e.g., about 4.9 to about 19 cm/sec; venous blood flow can be in the range of from about 1.5 to 7.1 cm/sec. Taking into consideration the diameters of the blood vessel diameters, one can determine blood flow rates of 3.0-26 ml/min in arteries and 1.2-4.8 ml/min. Klarhöfer M, et al., High-resolution blood flow velocity measurements in the human finger. Magn Reson Med. 2001 April; 45(4):716-9. doi: 10.1002/mrm.1096. PMID: 11284002. The foregoing values are illustrative only, and flow pressures and flow rate ranges for the body's blood vessels will be known to the person of ordinary skill in the art.

The viscosity profile curve represents a summary of expected resistance to flow throughout the subject's macro-circulation (blood vessels larger than capillaries0 including veins, arteries, venules, arterioles, etc. Certain illnesses are related to viscosity in the high flow vasculature such as the aorta, while other disorders are related to viscosity in the low flow vasculature such as the deep veins in the leg. In COVID-19 the major interest is the effect of virus induced damage to the lining of the blood vessels (vasculitis and endotheliopathy) that creates a nidus for clotting, and the large amounts of acute reactive proteins created by the intense inflammatory response to the viral infection that causes slowing (and possible interruptions of blood flow). The effect is near stasis conditions due to the highly elevated blood viscosity, especially in the slow flow vasculature. These two mutually facilitating factors (elevated viscosity and damage to the vessel lining) create a perfect physiological storm leading to a potentially lethal coagulopathy— disseminated intravascular coagulation (DIC) with embolization (clots breaking loose within the blood vessels). The resulting barrage of clots causes severe damage to the lungs (PE—pulmonary embolism) and other vital organs if the patient has a patent foramen ovale, a common birth defect. In the case of COVID-19, the low shear rate viscosity of whole blood reflects the amount of acute phase reactants (inflammatory proteins) present, and can predict the potential for intravascular clotting early enough to allow prophylactic intervention before development of disseminated intravascular coagulation (DIC). As shown, the GUI can then output viscosity profiles and relevant statistics.

Figure 15:
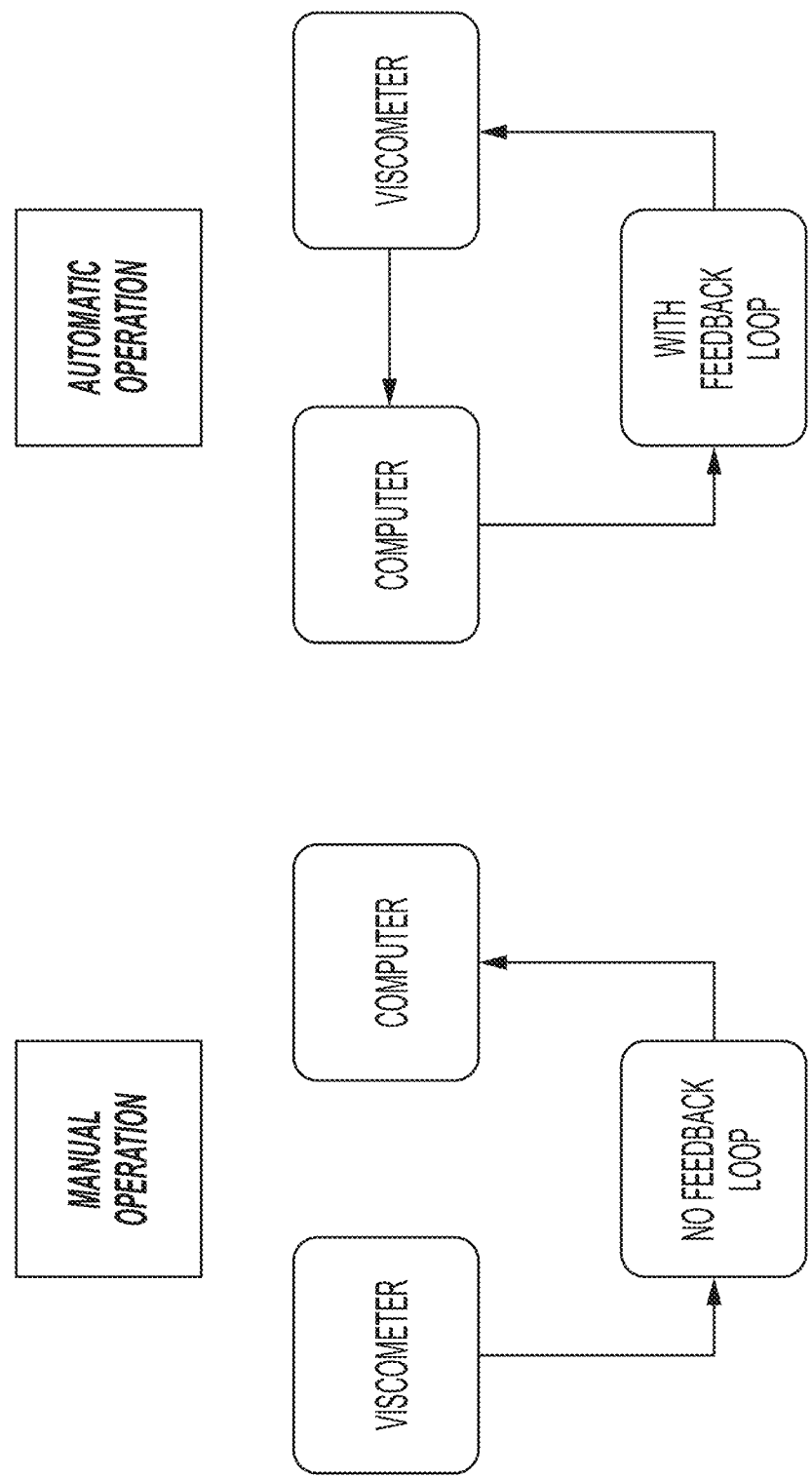
FIG. 15 depicts control flows for manual operation and automatic operation of systems according to the present disclosure.

FIG. 15 depicts a further control flow for manual operation and automatic operation of systems according to the present disclosure. A manual system can include, e.g., a manually-operated syringe as the reservoir.

Figure 16:
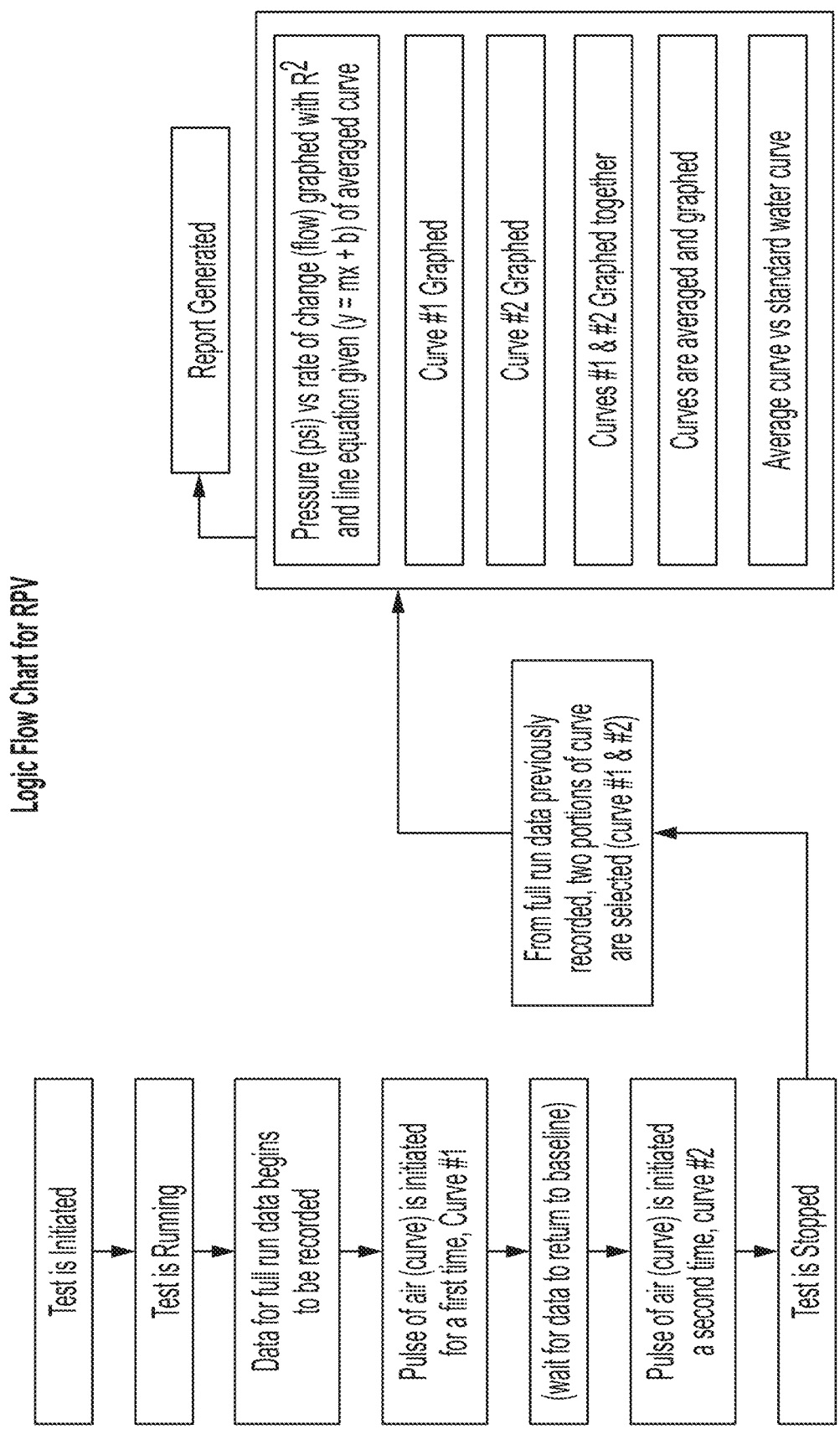
FIG. 16 provides an example logic chart for a system (rapid profile viscometer, or RPV) according to the present disclosure.

FIG. 16 provides an example logic chart for a system (rapid profile viscometer, or RPV) according to the present disclosure.

Figure 17:
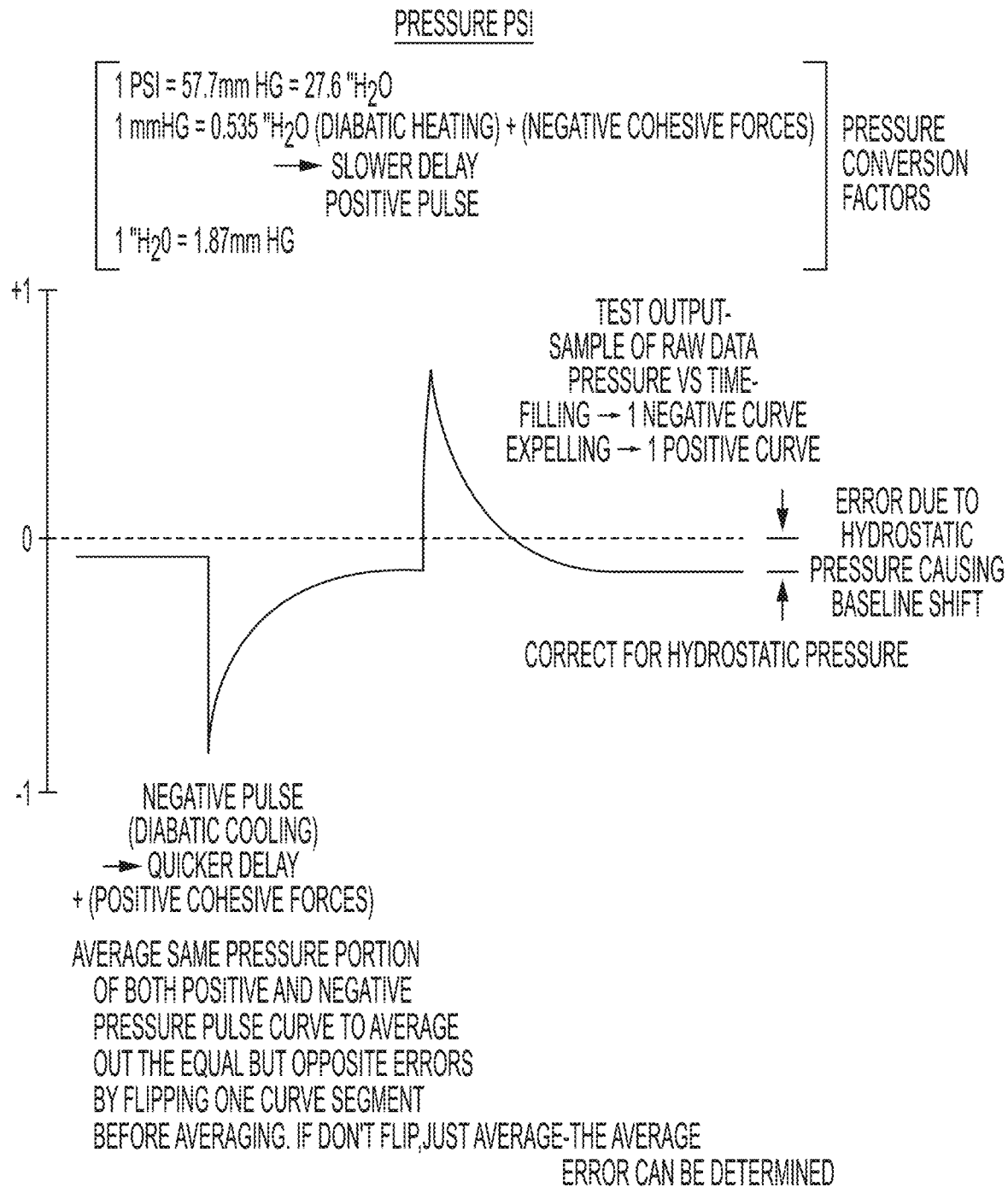
FIG. 17 provides an annotated illustration of exemplary data obtained according to the present disclosure.

FIG. 17 provides an annotated illustration of exemplary data obtained according to the present disclosure. These curves represent the raw pressure vs time data generated by the Rapid Profile Viscometer for the water control during a 20 second run. An equivalent whole blood test may take about a minute. The first curve represents the negative pressure pulse and the second curve represents the positive pressure pulse. The magnitudes are approximately the same, but in opposite directions. There is a baseline offset of approximately −0.2 psi which represents the transducer zero offset plus the hydrostatic pressure offset. This baseline offset following the curve becomes the baseline for the subsequent calculations for that curve. The device, procedure and software are designed to automatically correct for the hydrostatic, cohesive/adhesive, diabatic, atmospheric pressure and temperature errors present in any vertically oriented capillary viscometer. Both the whole blood and control (e.g., water) measures are made at ambient temperature, since the goal is to measure relative viscosity. Most important is the averaging out of the errors by recording and averaging both a negative curve and a positive curve of equivalent magnitude and duration performed during a single test. The area of the curves is chosen based on whether high flow rate or low flow rate are in consideration. In COVID-19 the low flow rate viscosity is of special interest so the equivalent low flow portions of the negative and positive curves are sliced and averaged.

Figure 18:
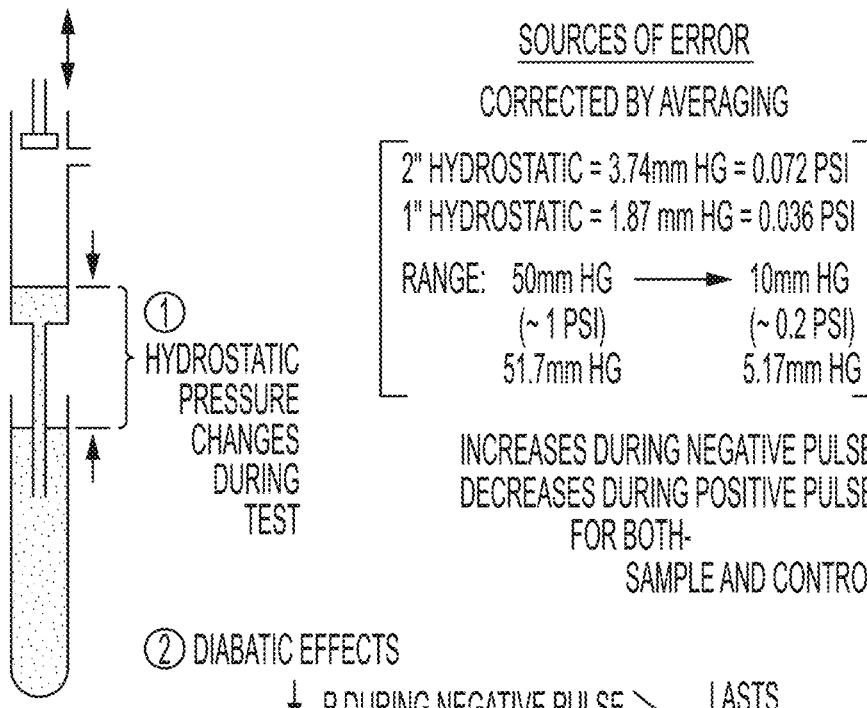
FIG. 18 provides an annotated illustration of potential sources of error that can arise in pressure vs. time measurements.

FIG. 18 provides an annotated illustration of potential sources of error that can arise in pressure vs. time measurements. The advantages of the vertical capillary and air pressure pulse design far outweigh the downside, namely correcting for hydrostatic and diabatic issues. Hydrostatic pressure changes slightly during the test, increasing during the negative curve and decreasing during the positive curve. However, when the curves are averaged the hydrostatic pressure errors are averaged out. The same applies to the diabatic errors (i.e., heating with compression and cooling with decompression) and the adhesive/cohesive errors which are also equal and opposite depending on direction of flow. Thus, all the significant errors are approximately equal but opposite. In any event the control fluids (water and PEG solutions also undergo the same physical phenomena during the test, and thus the relative viscosities can be considered reliable indicators of the relative flow resistance of the blood samples at comparable shear rates.

Figure 19:
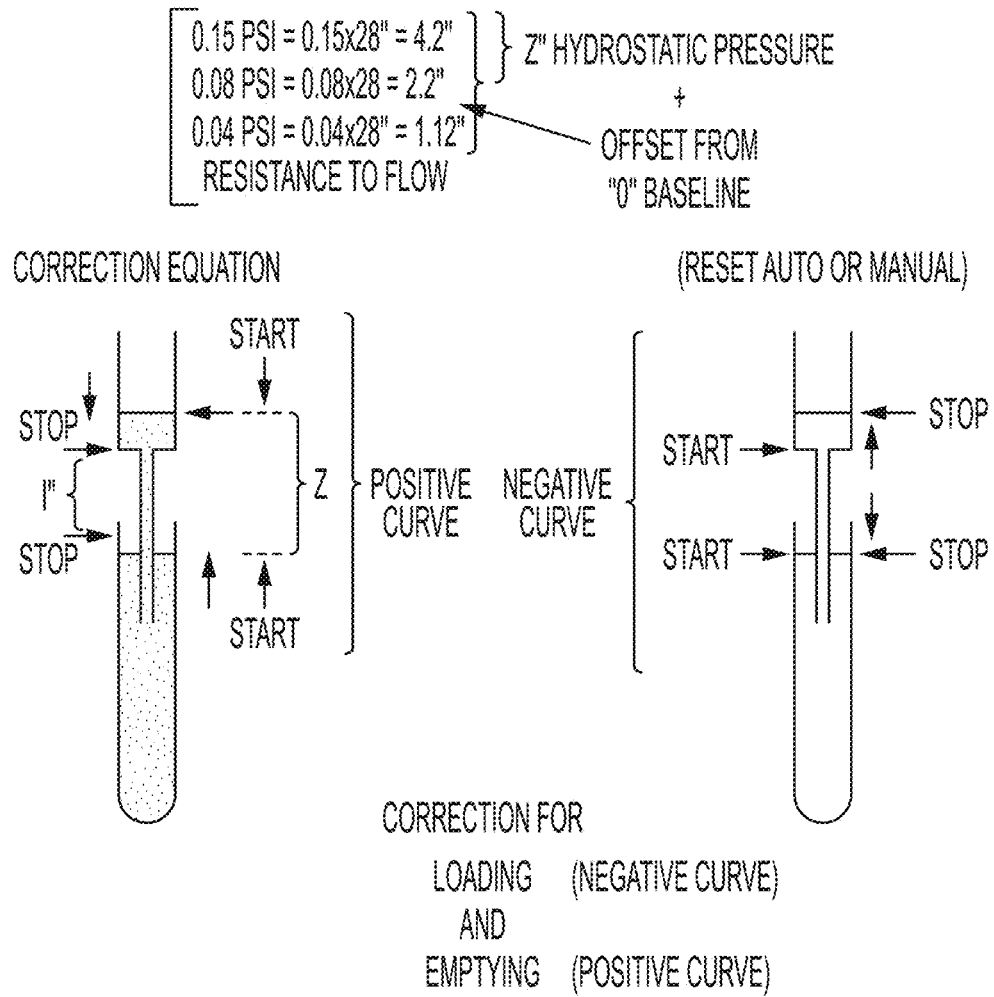
FIG. 19 provides an annotated illustration of potential sources of error that can arise in pressure vs. time measurements.

FIG. 19 provides an annotated illustration of potential sources of error that can arise in pressure vs. time measurements. Here is a representation of the changes in hydrostatic pressure during the test. The error can be calculated using a correction equation based on the inner diameter of the Vacutainer tube vs the inner diameter of the 3 ml syringe, or else by averaging the equivalent portions of the negative and positive curves. The latter solution also solves the other errors previously noted and represents a replication study (i.e., two consecutive curves that when averaged improve. the reliability, accuracy and precision of the test results.

Figure 20:
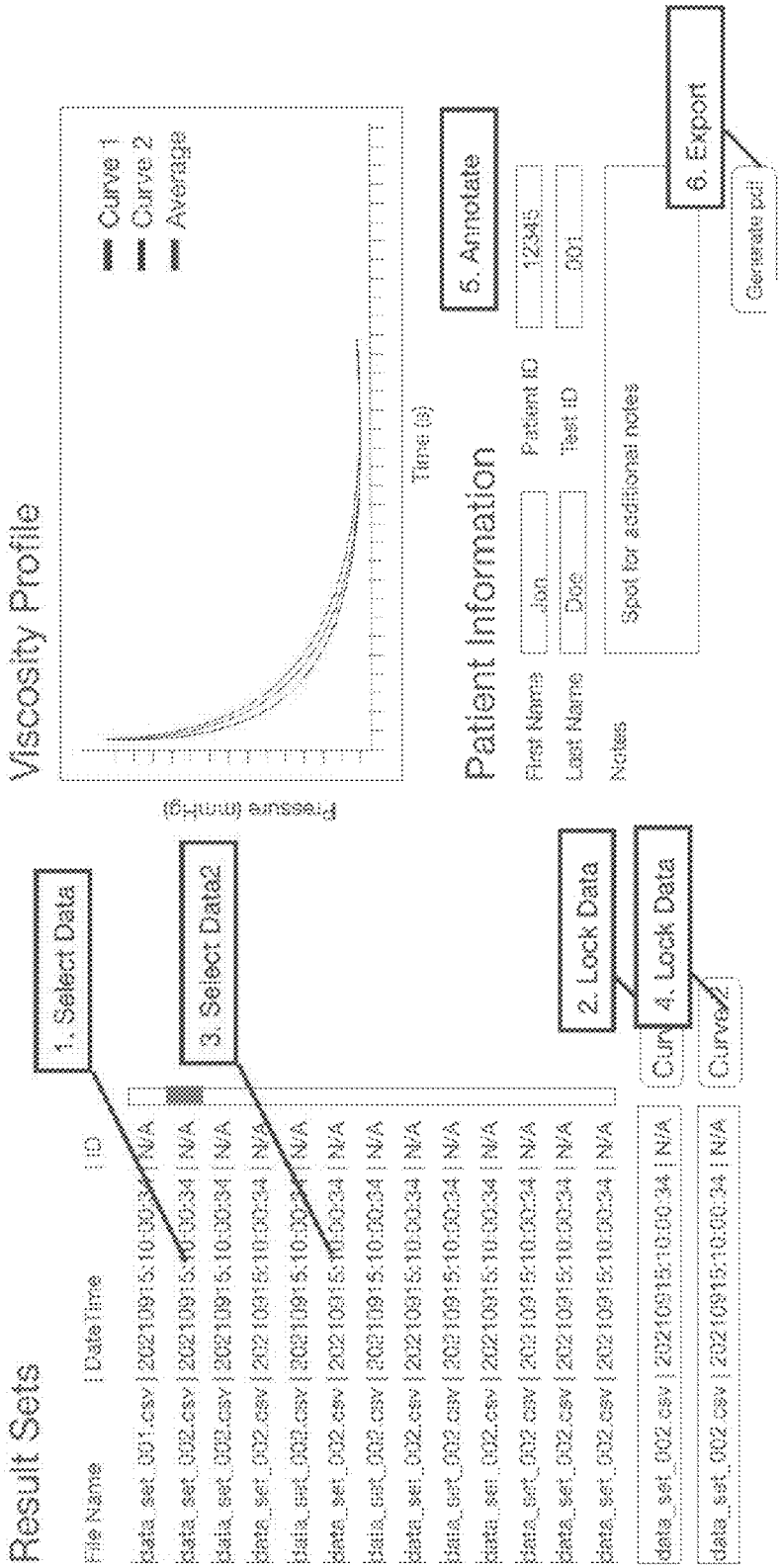
FIG. 20 provides an exemplary records view of data obtained according to the present disclosure.

FIG. 20 provides an exemplary records view of data obtained according to the present disclosure. As shown, a user can select certain data for analysis (e.g., data corresponding to physiologic flow rates and/or pressures in the vasculature), which data can be displayed, annotated, and/or associated with a particular patient record.

Figure 21B:
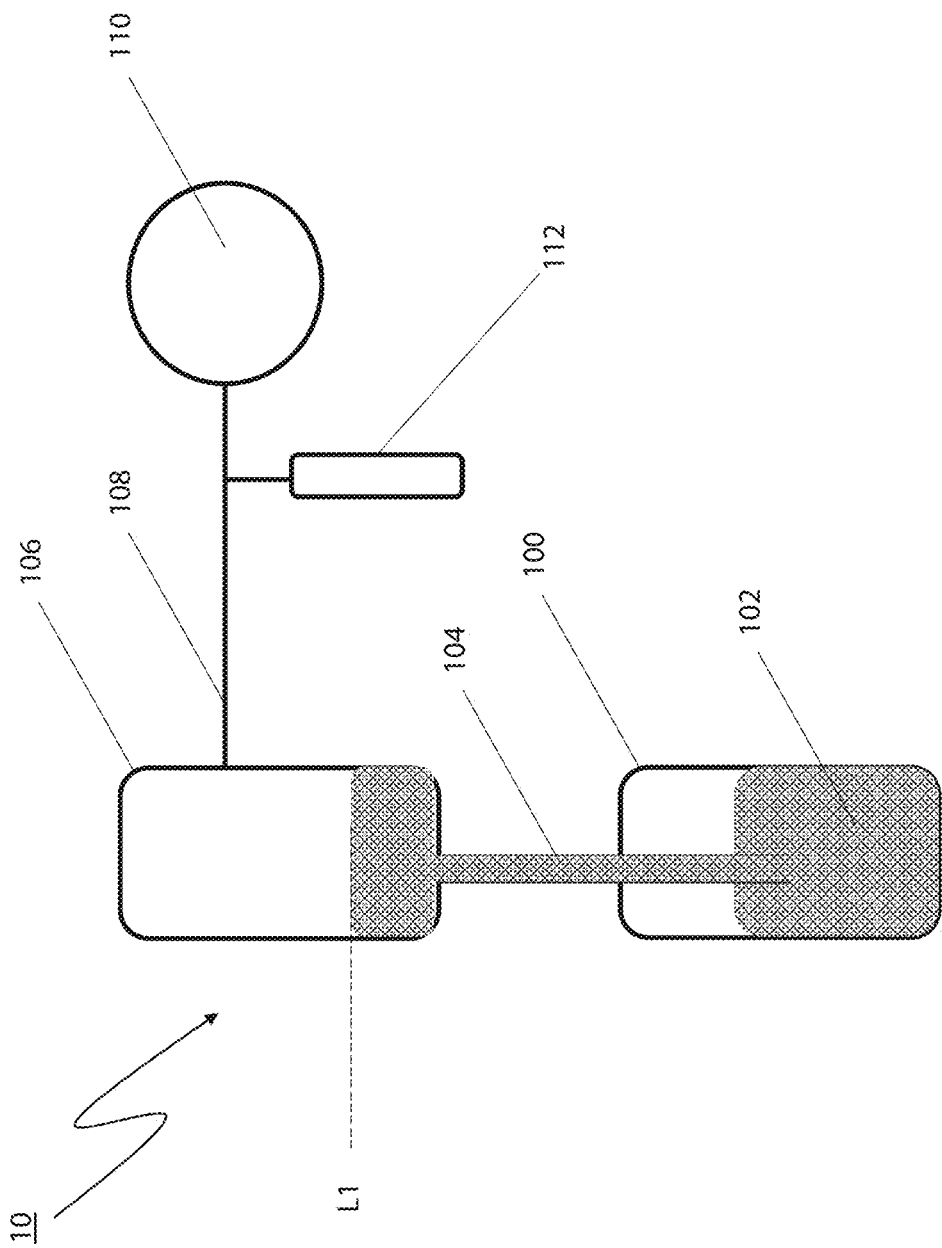

FIGS. 21A-21D provide a depiction of the operation of a system 10 according to the present disclosure. As shown in FIG. 21A, system 10 can include a sample container 100, which can be a blood collection tube such as a Vacutainer™. Reservoir 106 can be in fluid communication with sample container 100 via capillary 104. Capillary 104 can be a needle, such as a blunt 18-gauge needle. Capillary 104 can, however, be something other than a needle, as a needle is just an example capillary. Fluid 102 (e.g., whole blood, plasma, coagulating blood) is present in sample container 100.

Fluid 102 can be encouraged to travel through capillary 104 and into reservoir 106. This can be accomplished by, e.g., expanding the volume within reservoir 106. As but one example, if reservoir 106 is a syringe or other container with a moveable barrier, the volume within reservoir 106 can be increased so as to give rise to a relatively low pressure within reservoir 106, which pressure in turn encourages fluid 102 through capillary 104 and into reservoir 106.

Reservoir 106 can be in fluid communication with pressure transducer 110, e.g., via line 108 that places reservoir 106 into fluid communication with the pressure transducer. Reservoir 106 can also be open to the exterior environment, e.g., via a valve in fluid communication with line 108 or otherwise in fluid communication with reservoir 106. Priming volume 112 can be fluid communication with line 108 and also in fluid communication with reservoir 106. In this way, a pressure (e.g., a reduced pressure) within priming volume 112 can also motivate fluid into or out of reservoir 106. A valve (e.g., a two- or three-way valve) can be used at the intersection of priming volume 112 and line 108 to control the fluid communication between priming volume 112 and reservoir 106.

As shown in FIG. 21B, fluid 102 can be encouraged from sample container 100, through capillary 104, and into reservoir 106. Fluid 102 can attain level L1 (which can be considered a primed state) within reservoir 106, as shown. This can be accomplished by, e.g., exerting a negative pressure to the interior of reservoir 106. Such a pressure can be effected by, e.g., applying a negative pressure from priming volume 112. Pressure vs. time data can be collected in connection with the rise in fluid level to level L1. As shown in FIG. 21C, fluid 102 can be further encouraged into reservoir 106 such that fluid 102 attains a second level, L2, which level can be higher than L1. During the encouragement of fluid 102 into reservoir 106 to attain level L2, the pressure within reservoir 106 can be monitored by pressure transducer 110, thereby allowing for development of a pressure-time curve. (It should be understood, however, that the pressure within the reservoir can also be monitored during an initial introduction of fluid 102 into reservoir 106.) Reservoir 106 can be vented to the exterior environment at any point during system operation, e.g., before introduction of fluid 102 to reservoir 106, after initial introduction of fluid 102 to reservoir 106, or even after further a post-initial introduction of fluid 102 to reservoir 106, e.g., after fluid 102 attains level L2 as shown in FIG. 21C. Reservoir 106 can, however, also remain unvented during the course of a data collection. As one example, the enclosed volume defined by the reservoir 106, line 108, priming volume 112, and pressure transducer can remain sealed during the course of a data collection. As an example, the volume can remained sealed during the encouragement of fluid from sample container 100 into reservoir 106, and also during the encouragement of fluid out of reservoir 106 into sample container 100. It should be understood that a given fluid sample can be encouraged into the reservoir and encouraged out of the reservoir multiple times, e.g., to collect multiple data from the same sample and/or to monitor the sample over time (e.g., during a coagulation evaluation).

Figure 21D:
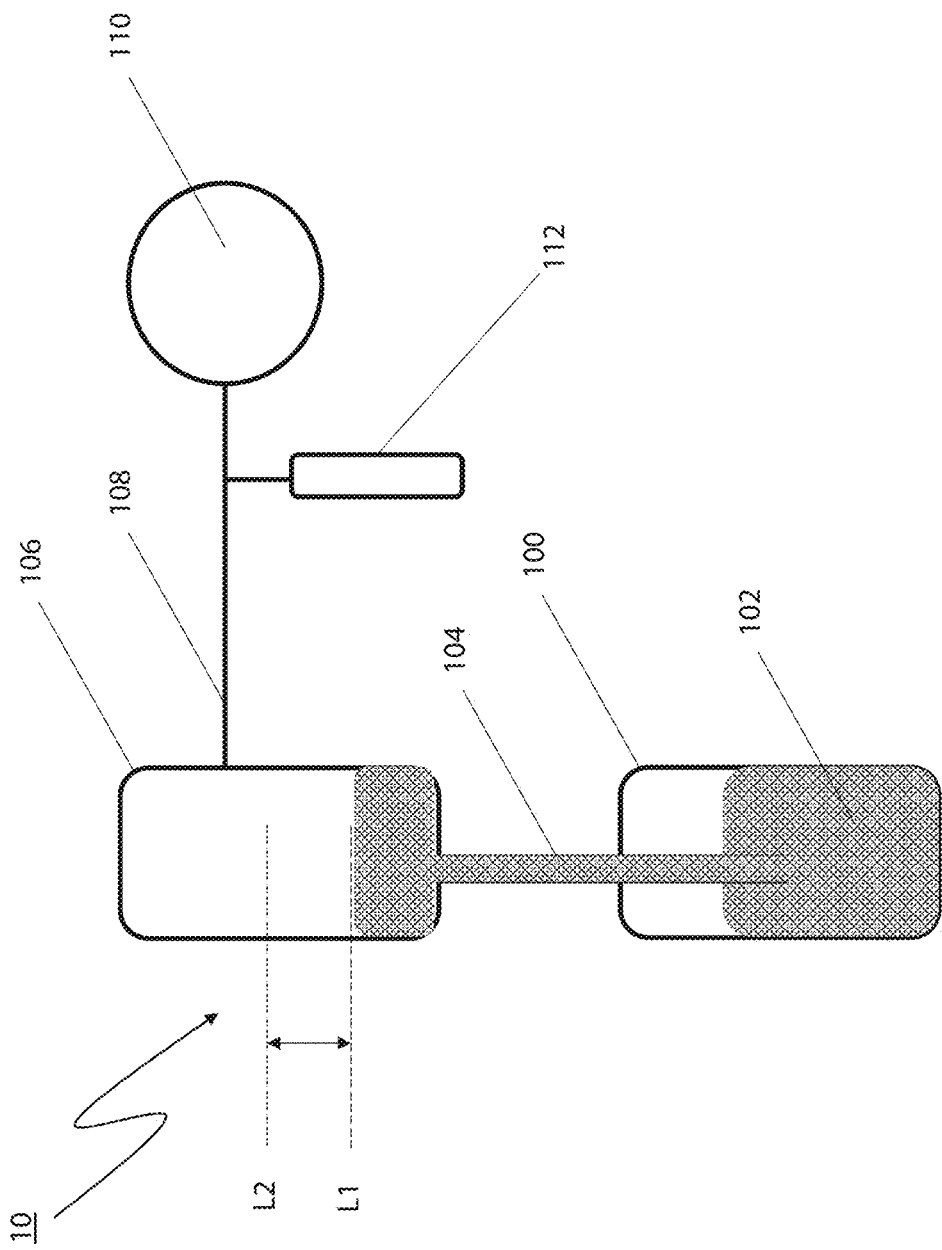

As shown in FIG. 21D, fluid 102 can be encouraged out of reservoir 106, e.g., such that the amount of fluid 102 in reservoir 106 goes from L2 to L1, as shown in FIG. 21D. Fluid 102 can be encouraged from reservoir 106 by, e.g., a pressure originating from priming volume 112, a pressure affected by reducing the volume of reservoir 106, by some other pressure source, or any combination of the foregoing. It should be understood that fluid 102 can be drawn up into and encouraged out of reservoir 106 multiple times, thereby allowing a user to obtain multiple readings/statistics on a given sample.

As an example (with reference to FIGS. 21A-21D, the interior volume of system 10 (which volume is defined by the volume of conduit 104, reservoir 106, line 108, priming volume 112, pressure transducer 110, and all connections therebetween can be 10 mL, with an example initial pressure within reservoir 106 of 760 mm Hg. By expanding priming volume 112 by 1 mL (e.g., by withdrawing a piston of priming volume 112), the volume in the system becomes 11 mL, and the pressure then becomes (760 mm Hg)×(10 mL)/(11 mL)=690 mm Hg, which reduced pressure can encourage fluid sample 102 from sample container 100 into reservoir 106 to achieve level L1. This new pressure of 690 mm Hg can be used as a baseline pressure. Further negative pressure can then be applied (e.g., by further expanding priming volume 112) to draw additional fluid sample into reservoir 106 (e.g., to level L2), with the expansion of priming volume 112 giving rise to a corresponding reduction in pressure that encourages the fluid sample into reservoir 106. With knowledge of the dimensions of the conduit (and the enclosed volume of the system), one can convert the pressure vs. time data that is collected into volume flow vs. time data. By reducing the volume of priming volume 112 (e.g., by advancing a piston), one can increase the pressure within reservoir 106 and encourage sample fluid out of the reservoir, collecting pressure vs. time data as the fluid exits the reservoir via conduit 104. Although not shown, a system according to the present disclosure can include locks, clamps, and/or other features to maintain the volume within reservoir 106 and/or priming volume 112, particularly where one or both of the foregoing is a syringe-type container.

Figure 22:
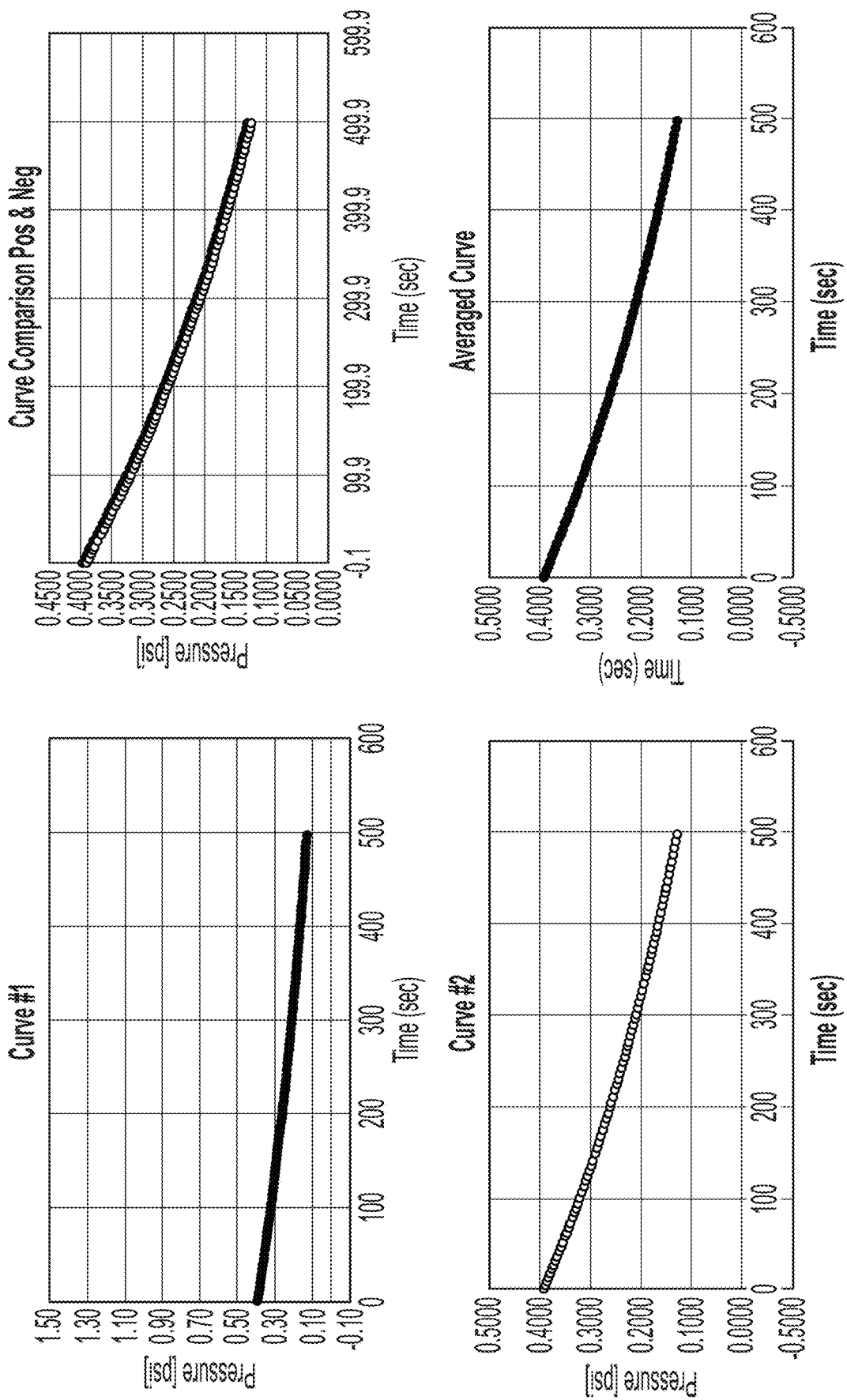
FIG. 22 provides example curves obtained by the disclosed technology.

FIG. 22 provides a replicability demonstration experiment in which 2 consecutive 1 PSI (~50 mmHg) positive time-pressure curves (Curve 1 and Curve 2) generated from the same sample of water at ambient temperature (70 deg. F.) were each sliced at 0.4 PSI (~20 mmHg) and at 0.1 PSI (~5 mmHg), which pressure range represents flow conditions within the low flow vasculature where blood exhibits non-Newtonian flow behavior. Each time-pressure curve slice took 5 seconds (~500 ms). The slices were first overlaid and then averaged. R square values were very high (0.98) indicating high consistency and replicability of test results.

Figure 23A:
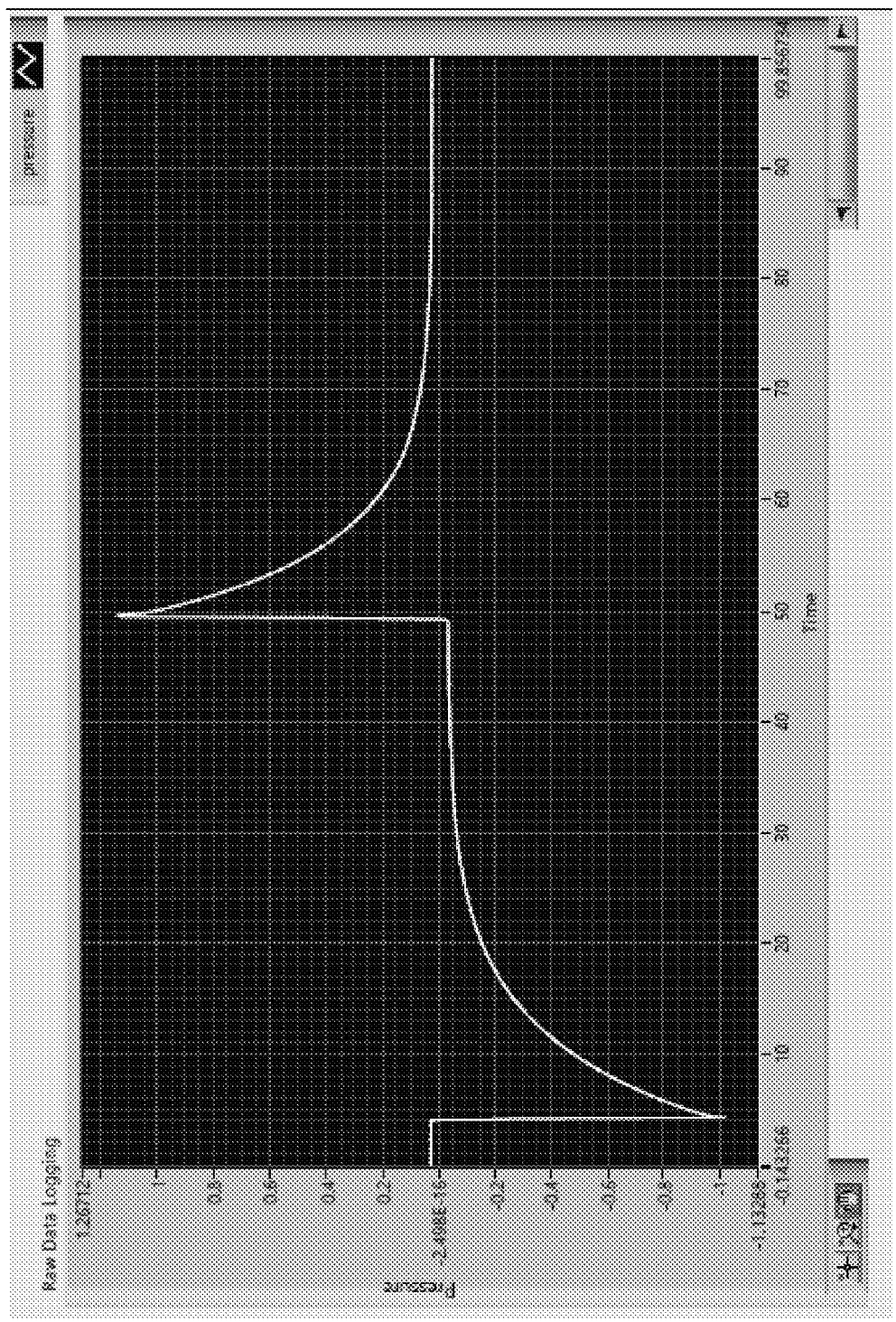
FIGS. 23A-23E provide example curves obtained by the disclosed technology.
Figure 23B:
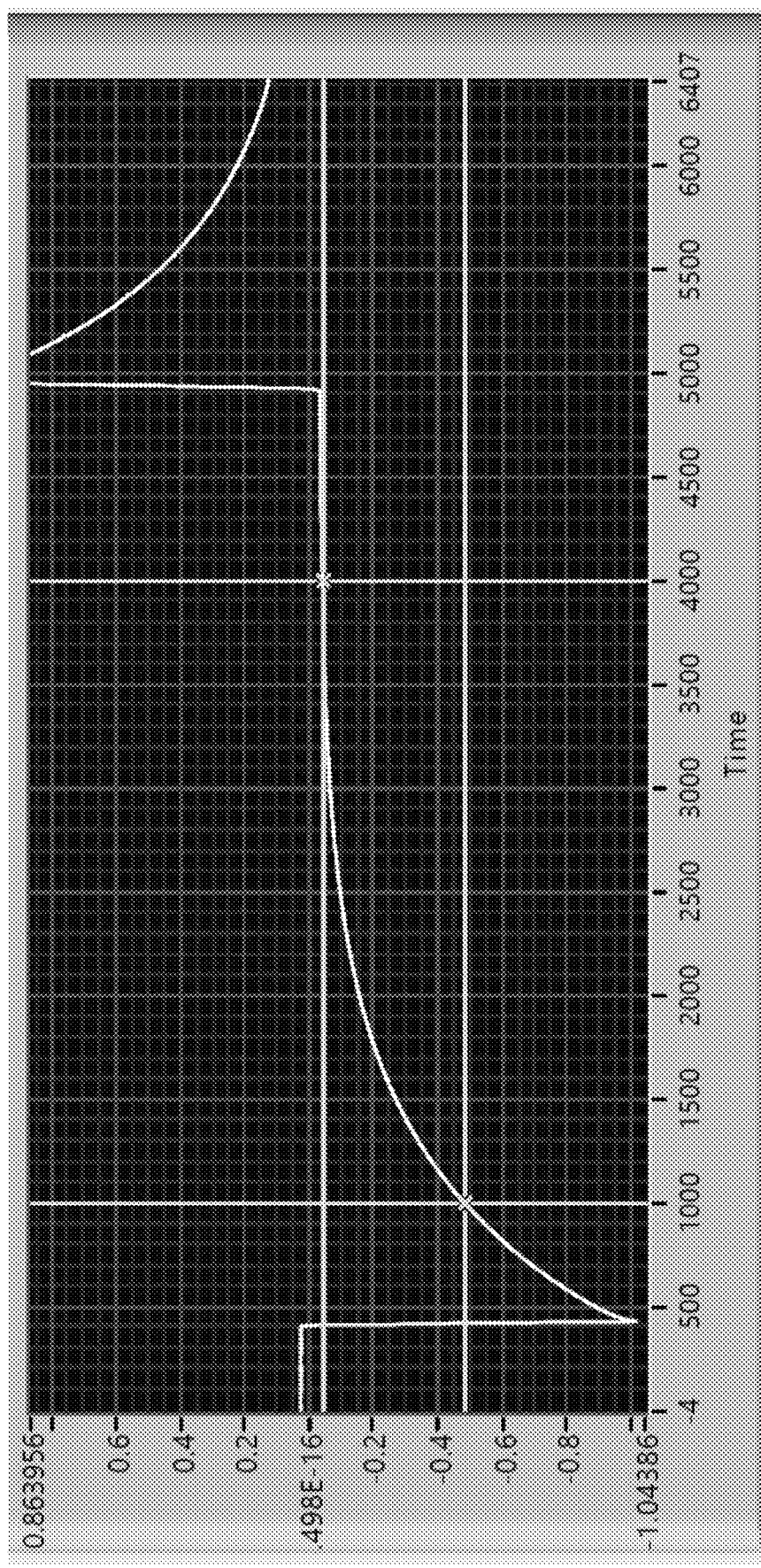
Figure 23C:
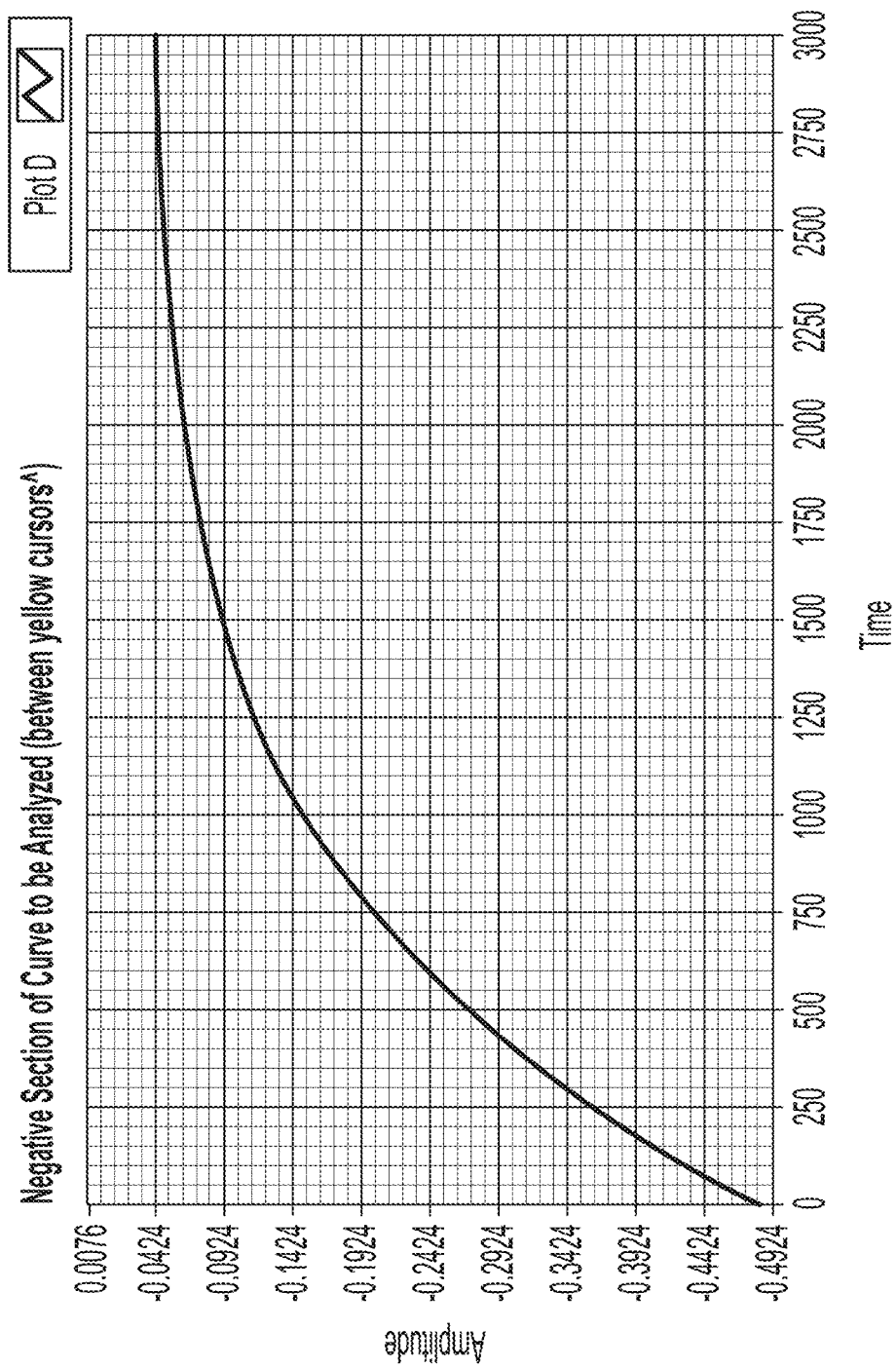
Figure 23D:
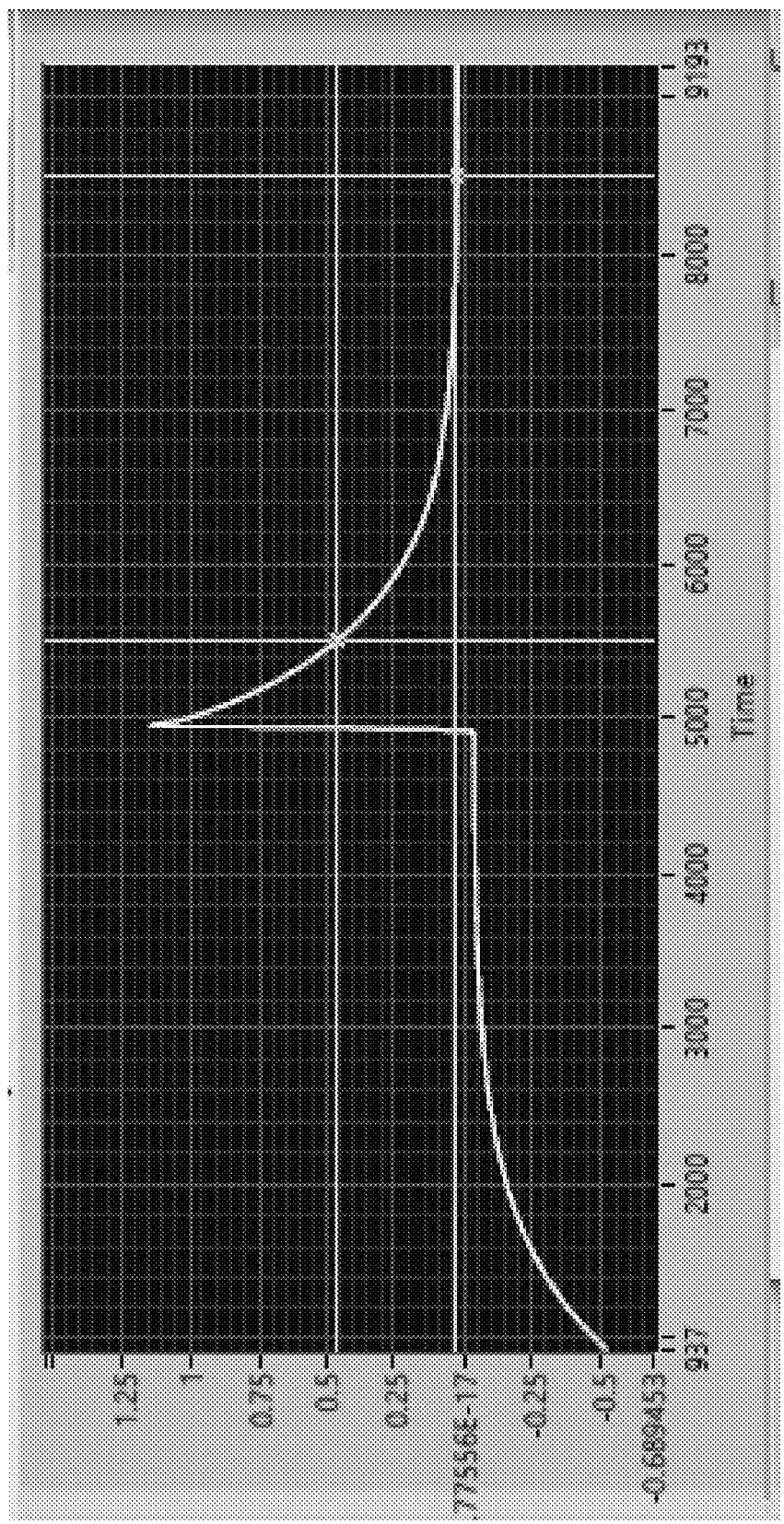
Figure 23E:
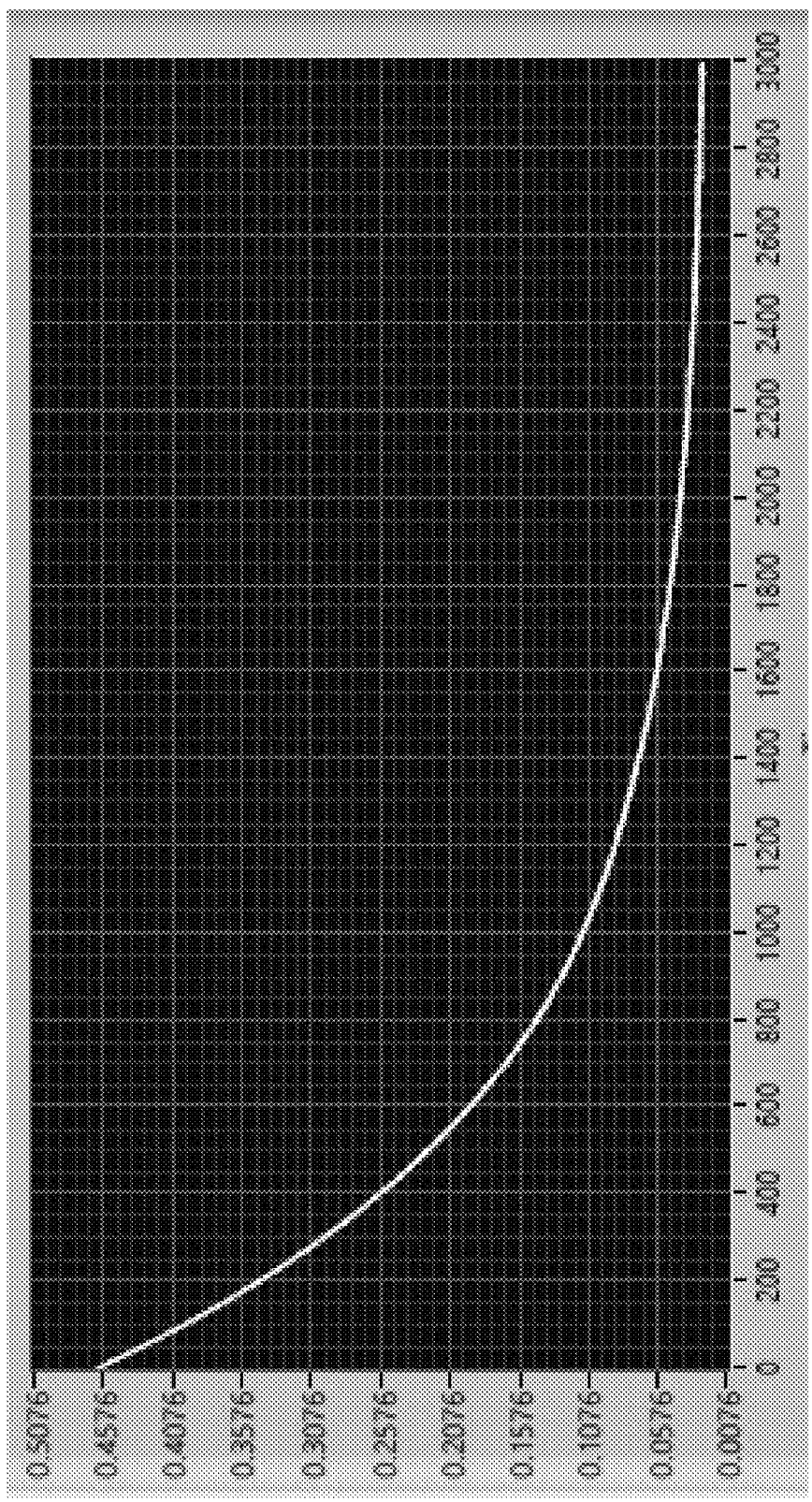

FIGS. 23A-23E provide a data slicing demonstration in which 2 consecutive 1 PSI (~5 mmHg) time-pressure curves are generated from the same sample of 30% PEG solution at ambient temperature (70° F.); each curve was sliced at ~20 mmHg and at ~5 mmHg which pressure range represents flow conditions within the low flow vasculature where blood exhibits non-Newtonian flow behavior. Each time-pressure curve slice took 30 seconds (~3000 ms). The slices were first overlayed and then averaged after flipping the negative curve. Standardized PEG solutions can also be used as the viscosity control for calculating relative viscosity. FIG. 23A provides raw pressure vs. time data obtained from the sample, with the left curve (or "negative curve") providing pressure-time data from exerting a negative pressure on a sample, and the right curve (or "positive curve") providing pressure-time data from exerting a positive pressure on a sample. FIG. 23B provides a view using lines to delineate the portion of the negative curve that was selected for further analysis; as shown (and as described elsewhere herein). FIG. 23C provides the section of the negative curve that was analyzed. FIG. 23C provides a view using lines to delineate the portion of the positive curve that was selected for further analysis; as shown (and as described elsewhere herein), a user can use lines, cursors, and other tools to select the portions of curves that are to be analyzed. FIG. 23D provides the section of the positive curve that was selected for further analysis.

Figure 24A:
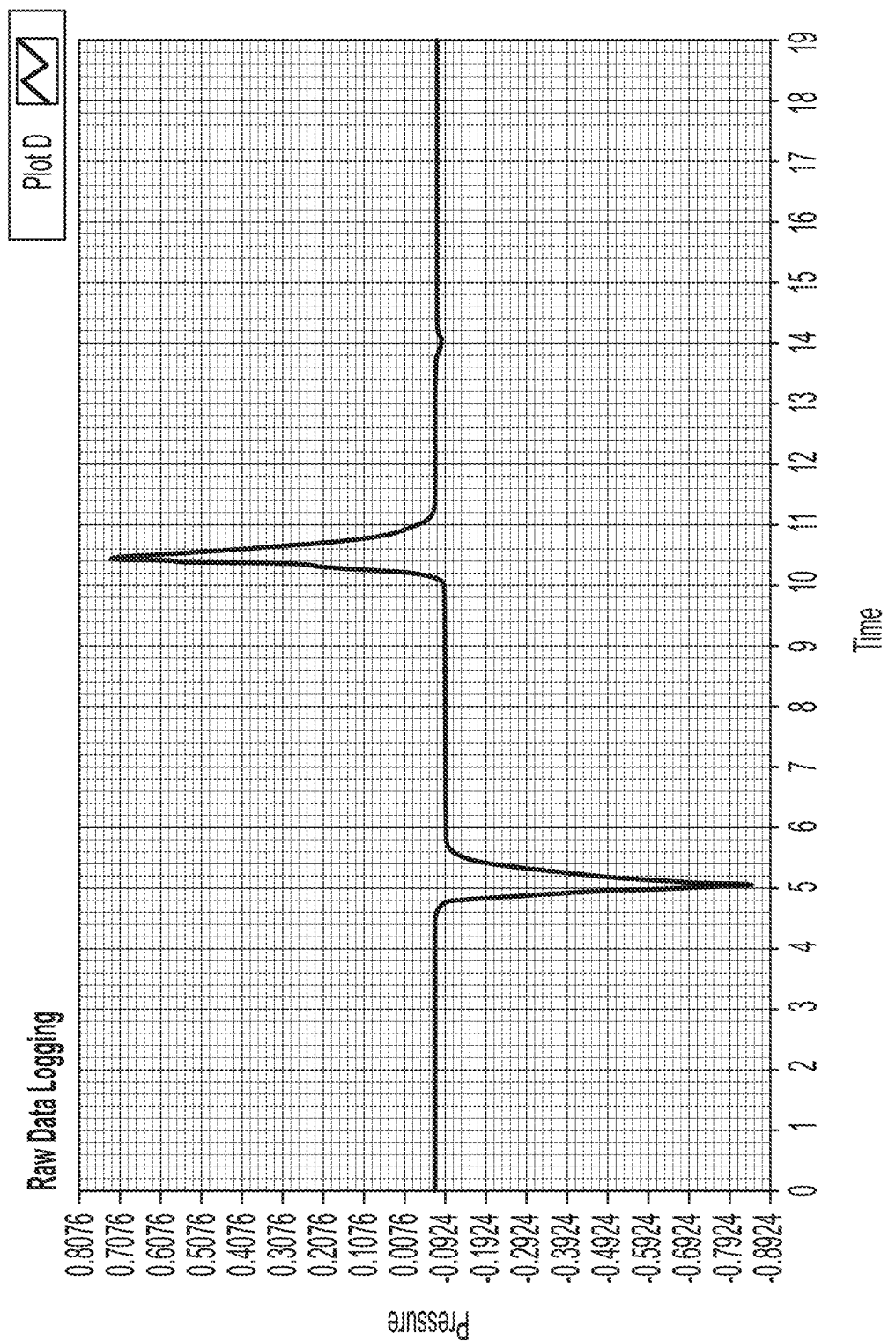
FIGS. 24A-24E provide example curves obtained by the disclosed technology.
Figure 24B:
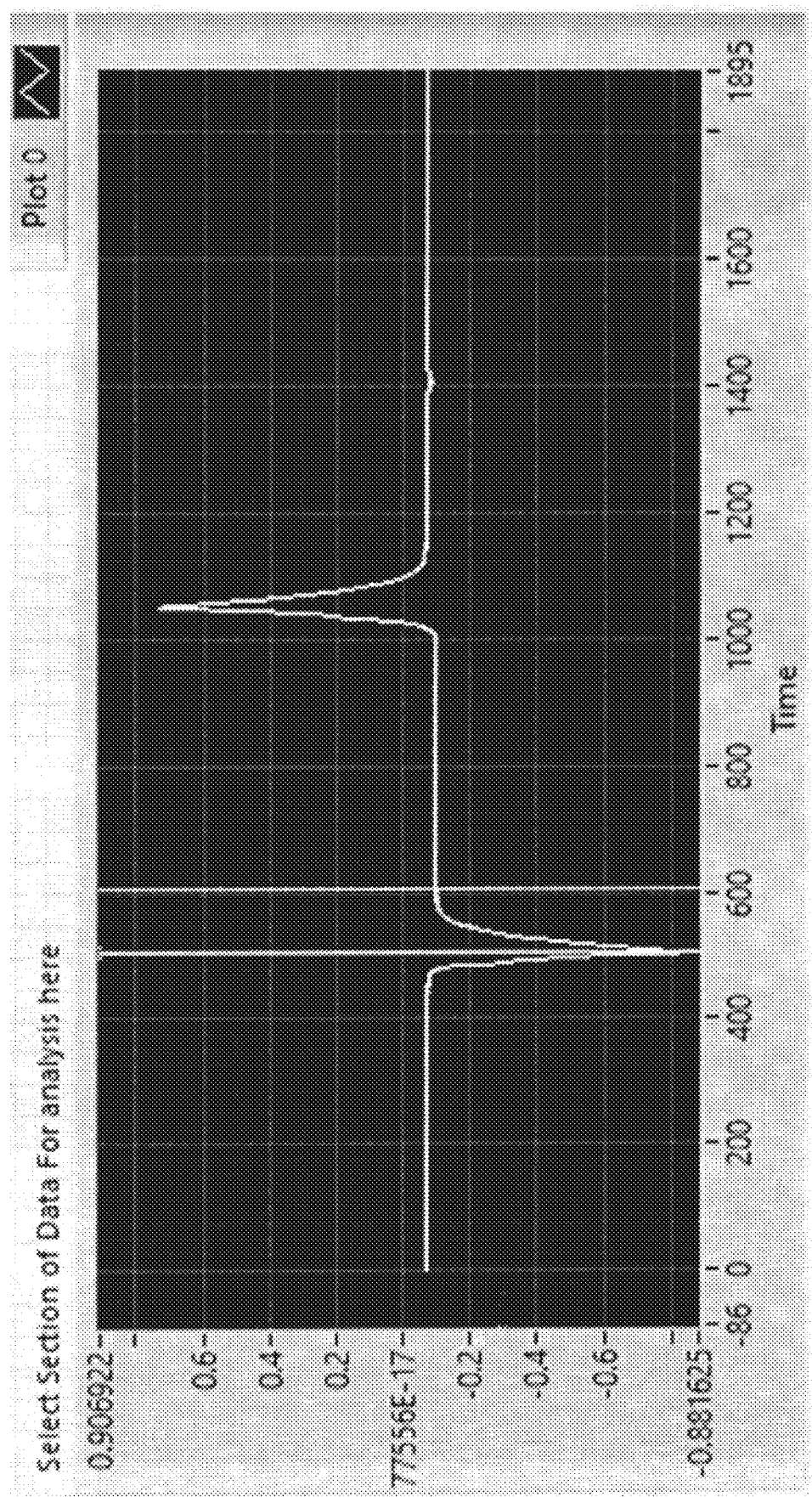
Figure 24C:
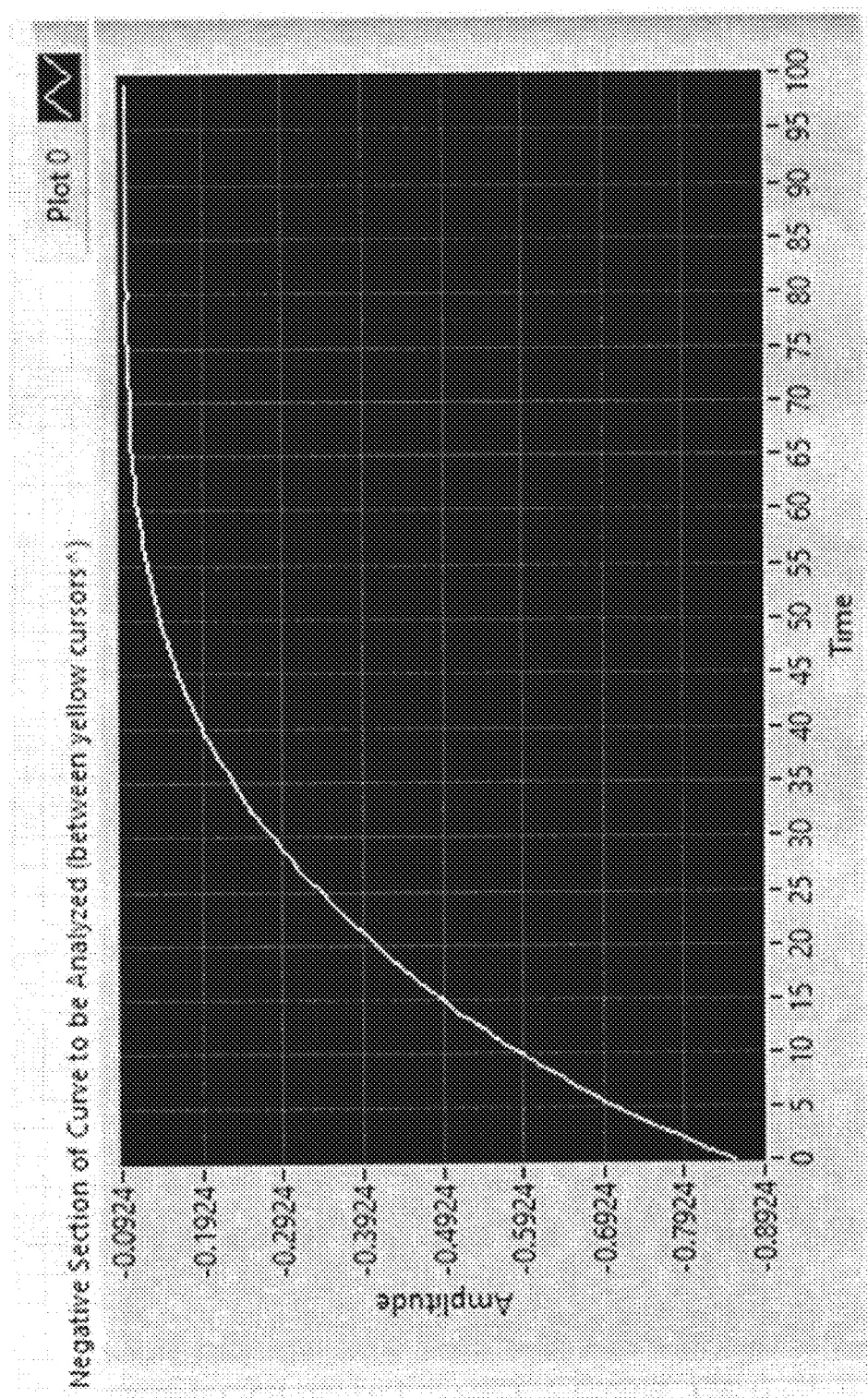
Figure 24D:
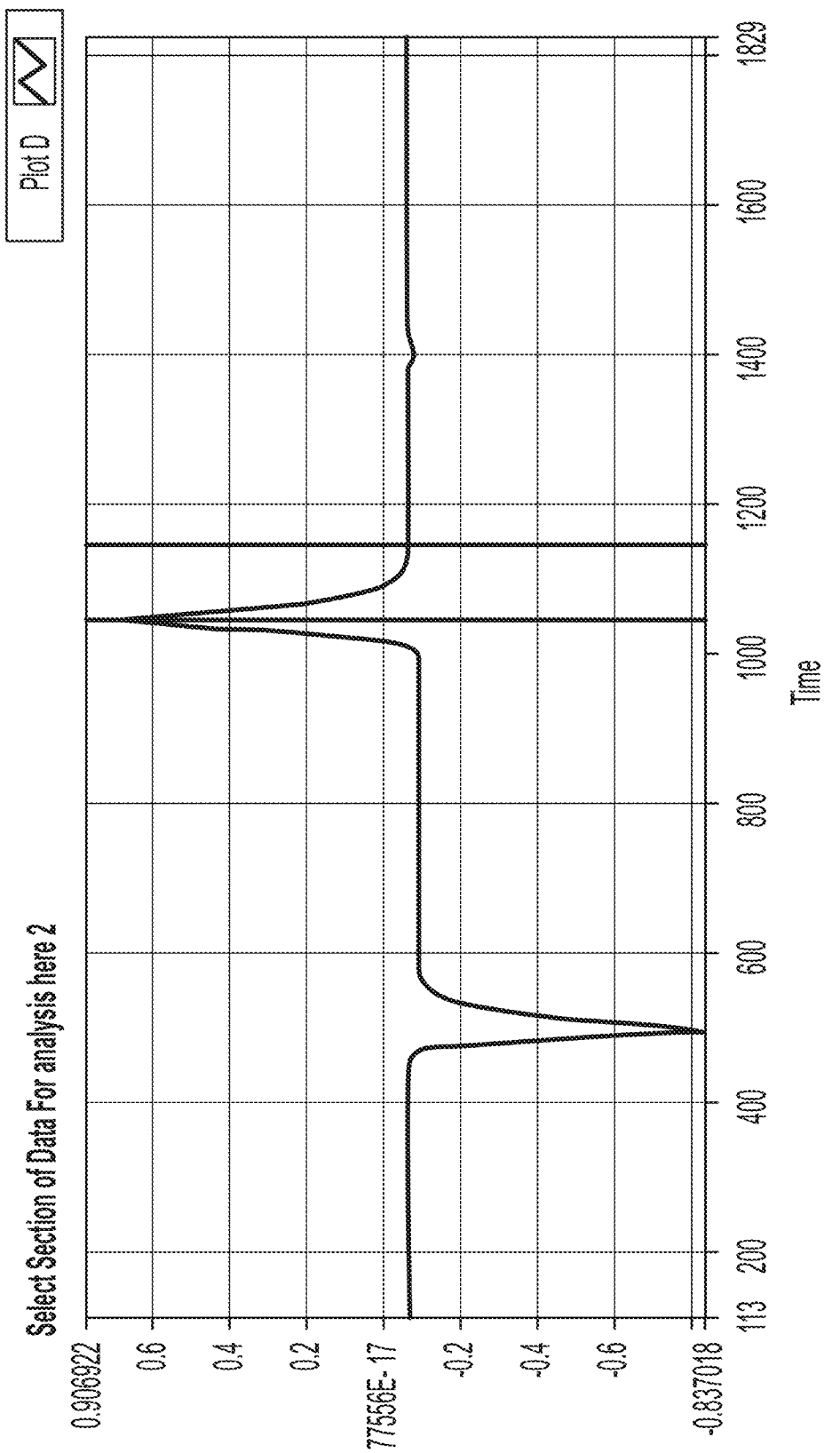
Figure 24E:
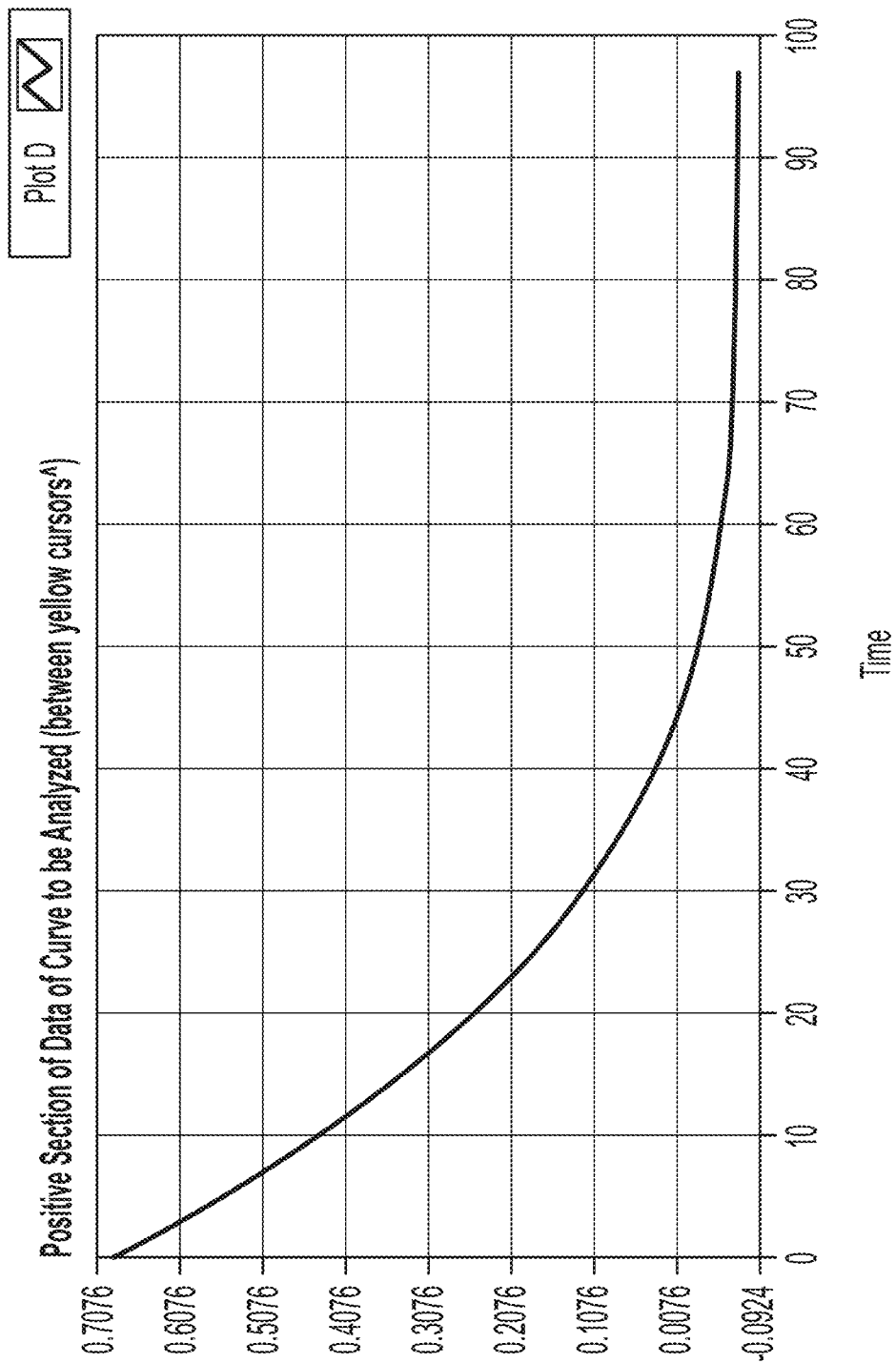

FIGS. 24A-24E provide data from an experiment in which 2 consecutive ~0.8 PSI (~40 mmHg) time-pressure curves were generated from the same sample of water at ambient temperature (70 deg. F.). The negative curve (FIG. 24C) was sliced at its minimum pressure (appx. 40 mm Hg; FIG. 24B) and the positive curve (FIG. 24E) was sliced at its maximum pressure (appx. 40 mm Hg; FIG. 24D) and each time-pressure curve terminated at its baseline (~0 mmHg). Each time-pressure curve took about 1 second (appx. 100 ms) to reach its baseline. These curves represent the pressure range and flow conditions within the low flow vasculature where blood exhibits non-Newtonian flow behavior. The negative slice was flipped and both slices were overlayed and then averaged. R square values were very high (0.98) indicating high consistency and replicability of test results. Water data is generally used as the viscosity control standard for calculating the "relative viscosity" of whole blood or blood plasma. The relative viscosity of blood at any given flow rate is a measure of the blood's resistance to flow under those conditions.

Figure 25:
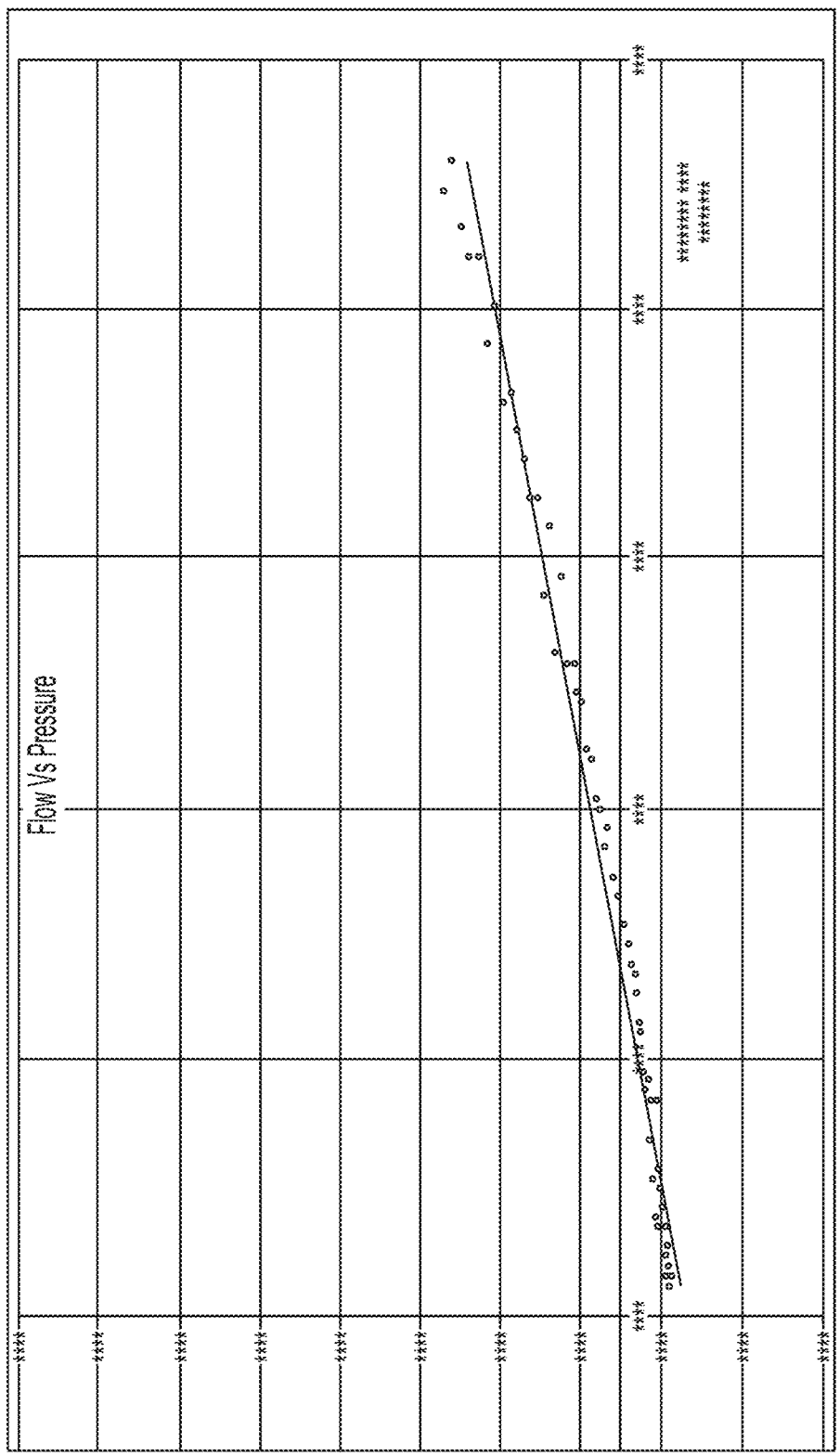
FIG. 25 provides included an example pressure-flow curve developed with the disclosed technology.

FIG. 25 provides an example pressure-flow curve (with a R-squared value of 0.97), which is an output from the viscosity calculations, and may have more meaning to some clinicians than a shear rate-dependent viscosity curve. Clinicians are more aware of expected blood pressures in various parts of the vasculature than viscosity gradients. The vertical axis on the left is PSI divided by 10 (0, 0.1000, 0.2000, 0.3000, etc.) A small negative offset of the baseline due to the transducer is observed. The horizontal axis is in mL/s flow rate (0, 0.50, 1.00, 1.50, 2.00, etc.).

Thus, the disclosed technology allows for rapid measurements of blood viscosity. The output of the disclosed technology can be pressure vs. time, flow rate vs. time, flow velocity vs. time, among other outputs. A user can compare data obtained with the present technology to baseline values, as well as comparing such data to expected or literature values, thereby allowing the user to assess a given patient's condition and to prescribe (or adjust) the patient's treatment as appropriate. A user can also evaluate a sample based on the overall time necessary for a sample to return to a baseline pressure after pressure is applied (or removed). Although monitoring the time to return to baseline pressure does not necessarily provide a quantitative viscosity measurement, the time to return can have clinical significance, as the time to return can provide a qualitative indication of viscosity (which can be correlated to disease and/or coagulation state), which qualitative indication can in turn be used to make treatment decisions for the patient.

Aspects

The following Aspects are exemplary only and do not serve to limit the scope of the present disclosure or the appended claims.

Aspect 1. A method, comprising: encouraging a fluid sample through a conduit into and/or out of a reservoir, the fluid sample optionally comprising one or more of (1) whole blood, (2) a blood plasma, or (3) whole blood during coagulation; monitoring a pressure within the reservoir related to the encouraging as a function of time so as to generate at least a first set of pressure vs. time data; and based at least in part on the first set of pressure vs. time data, determining one or more of a viscosity, a viscosity as a function of shear rate, or a flow resistance of the fluid sample.

As described, the disclosed technology is useful on whole blood (which can be uncoagulated), plasma, and/or whole blood during coagulation. The pressure within the reservoir can be modulated by, e.g., increasing the volume within the reservoir, e.g., if the reservoir is a syringe by pulling up on the plunger. Alternatively, the volume within the reservoir can be decreased, e.g., if the reservoir is a syringe by pressing down on the plunger. As another (non-limiting) alternative, one can exert a negative and/or positive pressure with an element (e.g., a syringe) that is in fluid communication with the reservoir.

As described herein, the method can include generating at least a first set of pressure vs. time data. Such data can be further processed (as described elsewhere herein) to provide pressure vs. flow data, viscosity data, and the like. The pressure vs. time data (or other data developed at least in part on said pressure vs. time data) can be displayed, recorded, transmitted, or any combination thereof. As explained one can determine one or more of a viscosity, a viscosity as a function of shear rate, or a flow resistance of the fluid sample. Also as explained, one can also determine a time required for a sample to achieve and/or return to a given pressure, which time (which can be termed a "recovery time" in some instances) can be indicative of a viscosity of the sample under study. For example, one could compare the recovery time of a given sample to the recovery time associated with a sample that is indicative of an acute blood clotting state. This can be accomplished by, e.g., encouraging a sample from a sample container into a reservoir (as shown in FIGS. 21A-21B). Following that encouragement, the reservoir can be placed into fluid communication with the environment exterior to the reservoir (or into another volume) so as to relieve the pressure within the reservoir, and the user can monitor the time needed for the pressure within the reservoir to relieve. This can be performed such that sample material that has transited from the sample container to the reservoir then returns from the reservoir to the sample container.

Aspect 2. The method of Aspect 1, further comprising relating the one or more of a viscosity, a viscosity as a function of shear rate, or a flow resistance of the fluid sample to a physiologic state of a subject. Such a state can be, e.g., a disease state.

Aspect 3. The method of any one of Aspects 1-2, further comprising administering a treatment or withdrawing a treatment in response to the physiologic state of the subject. Examples of such treatments include, e.g., anti-inflammatories, blood thinners, and the like.

Aspect 4. The method of any one of Aspects 1-3, comprising determining, based at least in part on the first set of pressure vs. time data, a viscosity of the fluid sample. The viscosity can be compared to a standard or a range of standards, the result of said comparison being then used to assess a condition of the patient.

Aspect 5. The method of any one of Aspects 1-4, comprising determining, based at least in part on the first set of pressure vs. time data, a viscosity as a function of shear rate of the fluid sample.

Aspect 6. The method of any one of Aspects 1-5, comprising determining, based at least in part on the first set of pressure vs. time data, a flow resistance of the fluid sample.

Aspect 7. The method of any one of Aspects 1-6, wherein the fluid sample is encouraged into the reservoir by expanding the reservoir. The fluid sample can also, in some embodiments, be encouraged into the reservoir by applying a pressure to a sample container in which the fluid sample is disposed. It should be understood that the reservoir can be placed into fluid communication with the environment exterior to the reservoir (or another volume, which volume can be enclosed) at any point, e.g., to equalize pressures or even to vent excess pressure. Such fluid communication can be done before fluid is encouraged into or out of the reservoir, during fluid encouragement into or out of the reservoir, or even after fluid is encouraged into or out of the reservoir. As an example, a reservoir can be opened and then closed to the environment exterior to the reservoir to as to set a baseline pressure. Sample can be encouraged into the reservoir, with the related development of a pressure vs. time curve related to that sample encouragement. After the pressure within the reservoir stabilizes, the reservoir can be vented to the exterior and then sealed. After re-sealing, fluid sample within the reservoir can then be encouraged out of the reservoir, with a further development of a pressure vs. time curve related to the encouragement.

Aspect 8. The method of any one of Aspects 1-7, wherein the fluid sample is encouraged into the reservoir by applying a negative pressure from a source in fluid communication with the reservoir.

Aspect 9. The method of any one of Aspects 1-8, further comprising reducing a pressure within the reservoir by expanding a priming volume in fluid communication with the reservoir. Such a priming volume can be, e.g., a syringe. The priming volume can be manually controllable, but can also be automated or machine-controlled.

Aspect 10. The method of Aspect 9, further comprising interrupting fluid communication between the priming volume and the reservoir.

Aspect 11. The method of any one of Aspects 1-10, further comprising encouraging the fluid sample out of the reservoir following encouraging the fluid sample into the reservoir and monitoring a pressure within the reservoir related to the encouraging out of the reservoir as a function of time so as to generate a second set of pressure vs. time data.

Aspect 12. The method of Aspect 11, further comprising determining the viscosity, the viscosity as a function of shear rate, or the flow resistance of the fluid sample based at least in part on the second set of pressure vs. time data.

Aspect 13. The method of Aspect 12, wherein the viscosity, the viscosity as a function of shear rate, or the flow resistance of the fluid sample is based at least in part on an average that comprises the first set of pressure vs. time data and the second set of pressure vs. time data. The development of such an average is described elsewhere herein, and is also shown in FIG. 9. It should be understood that an average can comprise a set of data that has been transformed, inverted, or otherwise "flipped" so as to be averageable with another set of data. Such a procedure is described elsewhere herein and also shown in FIG. 9 and FIG. 22.

Aspect 14. An apparatus, comprising: a conduit configured to communicate a fluid therein; a reservoir, the reservoir being in fluid communication with the conduit, the reservoir optionally being expandable; a transducer, the transducer configured to measure a pressure within the first reservoir related to fluid entry and/or fluid egress from the expandable reservoir; and a memory in communication with the transducer, the memory configured to record at least a first set of pressure vs. time data related to fluid entry and/or fluid egress from the expandable reservoir.

A conduit can be, e.g., a syringe needle, although this is not a requirement. Other conduits include, e.g., capillaries, cannulas, and the like.

Aspect 15. The apparatus of Aspect 14, further comprising a processor in communication with the transducer, the processor being configured to execute instructions to relate at least the first set of pressure vs. time data of the transducer to a viscosity of a fluid communicated into and/or out of the first reservoir to any one or more of a viscosity, a viscosity as a function of shear rate, or a flow resistance of a fluid sample communicated within the conduit. The processor can be embodied within a computer, a mobile computing device, and the like.

Aspect 16. The apparatus of Aspect 15, the processor being configured to execute instructions to relate an average that comprises least the first set of pressure vs. time data of the transducer and a second set of pressure vs. time data of the transducer to a viscosity of a fluid communicated into and/or out of the first reservoir to any one or more of a viscosity, a viscosity as a function of shear rate, or a flow resistance of the fluid. The instructions can also instruct to transform, invert, or otherwise "flip" a data set so that the data set shares a basis with and is thus average-able with another set of data. Such a procedure is described elsewhere herein and also shown in FIG. 9 and FIG. 22.

Aspect 17. The apparatus of any one of Aspects 14-16, further comprising a priming volume, the priming volume in interruptible fluid communication with the reservoir. A priming volume can be, e.g., a syringe or other volume that is expandable or contractable. This is not a requirement, as the priming volume can be of fixed volume and then be pressurized and/or depressurized.

Aspect 18. The apparatus of Aspect 17, wherein the priming volume is operable to draw a fluid through the conduit into the reservoir. One such arrangement is provided in FIG. 21A, in which priming volume 112 can be used to draw fluid 102 through conduit 104 into reservoir 106.

Aspect 19. The apparatus of Aspect 17, wherein the priming volume is a syringe.

Aspect 20. The apparatus of any one of Aspects 14-19, wherein the reservoir is a syringe. As described elsewhere herein, the reservoir can be of variable volume, but this is not a requirement, as the reservoir can be of fixed volume.

Aspect 21. A method, comprising effecting operation of an apparatus according to any one of Aspects 14-20.

Aspect 22. The method of Aspect 21, wherein the operation is effected on a subject's sample of whole blood, plasma, or coagulating blood.

Aspect 23. The method of Aspect 22, further comprising classifying a disease state of the subject based on the operation of the apparatus.

Aspect 24. The method of Aspect 23, further comprising recommending a treatment for the disease state of the subject. The disclosed methods can also include administering a treatment in accordance with a disease state of the subject identified by analysis of pressure vs. time information or on data related to such a pressure vs. time information.

Aspect 25. The method of any one of Aspects 21-24, wherein the operation is automated.

Aspect 26. A system, comprising: a viscometer, the viscometer configured to communicate a fluid sample to and/or from a reservoir and develop pressure vs. time data of the reservoir related to the communication of said fluid; and a processor, the processor configured to relate the pressure vs. time data to a viscosity of the fluid sample. The pressure vs. time data can also be related to a flow resistance of the fluid sample, which fluid resistance can be developed based on the dimensions of a conduit through which the fluid sample is communicated.

Aspect 27. A method, comprising: encouraging a fluid sample into and/or out of a reservoir, the fluid sample optionally comprising one or more of (1) whole blood, (2) a blood plasma, or (3) whole blood during coagulation; monitoring a pressure within the reservoir related to the encouraging as a function of time so as to generate at least a first set of pressure vs. time data; and based at least in part on the first set of pressure vs. time data, determining one or more of a viscosity, a viscosity as a function of shear rate, or a flow resistance of the fluid sample. The methods can further include any one or more of the features recited in Aspects 2-13.

It should be understood that in some embodiments, the conduit and the reservoir can be one and the same, i.e., the fluid sample is communicated directly into a conduit/reservoir, with the pressure within the conduit/reservoir being monitored. For example, as shown in FIGS. 26A-26D (which depict a system 12), sample 102 can be encouraged into and out of conduit/reservoir 104/106, and the pressure within the conduit/reservoir 104/106 can be monitored by pressure transducer 110. Such an embodiment can function similar to the embodiment shown in FIGS. 21A-21D.

Figure 26A:
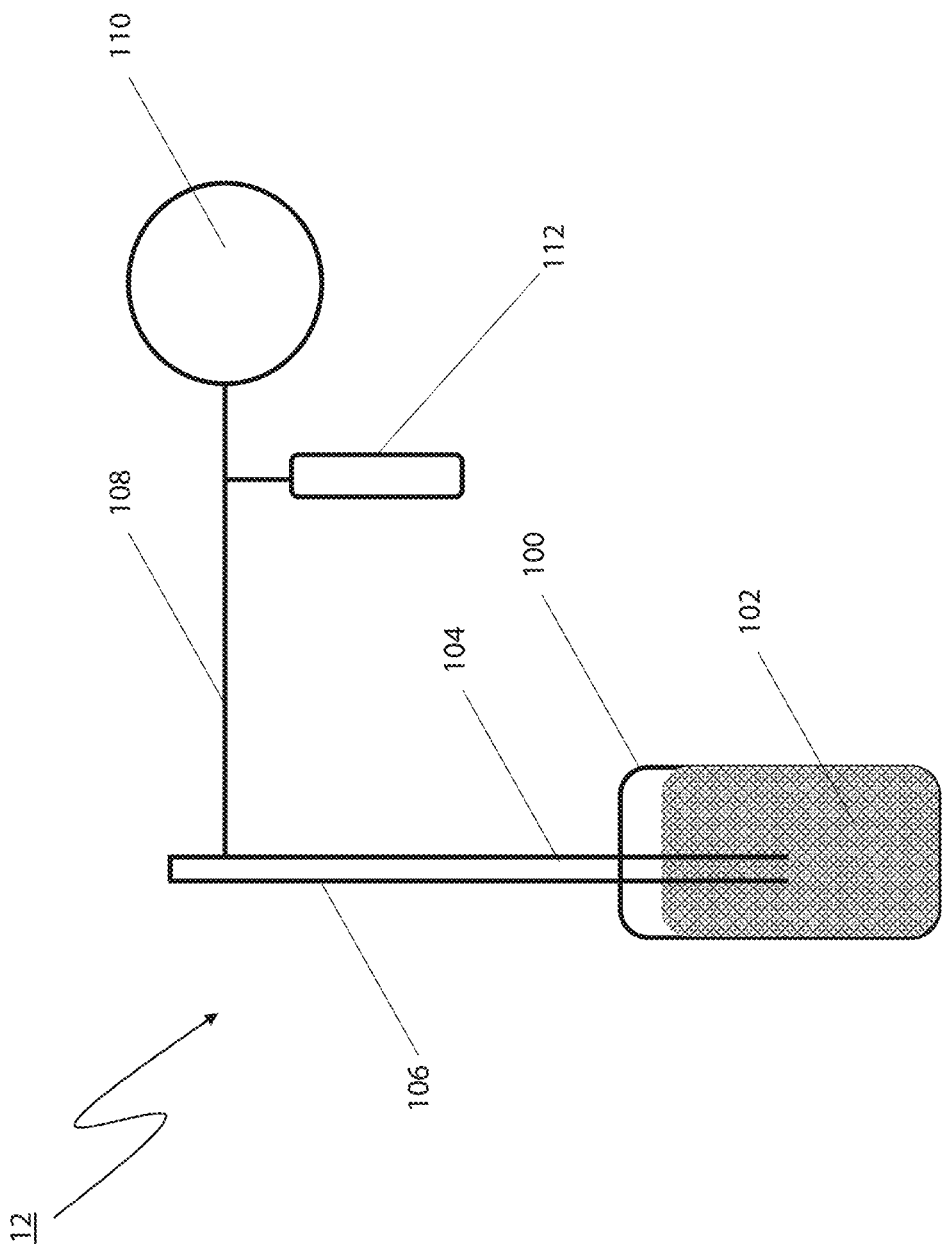
FIGS. 26A-26D provide a depiction of the operation of a system according to the present disclosure.

As shown in FIG. 26A, a system can include a sample container 100, which can be a blood collection tube such as a Vacutainer™. Reservoir 106 can be in fluid communication with sample container 100 via capillary/reservoir 104/106. Fluid 102 (e.g., whole blood, plasma, coagulating blood) is present in sample container 100.

Fluid 102 can be encouraged to capillary/reservoir 104/106. This can be accomplished by, e.g., expanding the volume within capillary/reservoir 104/106. As but one example, if capillary/reservoir 104/106 is a syringe or other container with a moveable barrier, the volume within capillary/reservoir 104/106 can be increased so as to give rise to a relatively low pressure within capillary/reservoir 104/106, which pressure in turn encourages fluid 102 to capillary/reservoir 104/106.

Capillary/reservoir 104/106 can be in fluid communication with pressure transducer 110, e.g., via line 108 that places reservoir 106 into fluid communication with the pressure transducer. Capillary/reservoir 104/106 can also be open to the exterior environment, e.g., via a valve in fluid communication with line 108 or otherwise in fluid communication with reservoir 106. Priming volume 112 can be fluid communication with line 108 and also in fluid communication with capillary/reservoir 104/106. In this way, a pressure (e.g., a reduced pressure) within priming volume 112 can also motivate fluid into or out of capillary/reservoir 104/106. A valve (e.g., a two- or three-way valve) can be used at the intersection of priming volume 112 and line 108 to control the fluid communication between priming volume 112 and capillary/reservoir 104/106.

Figure 26B:
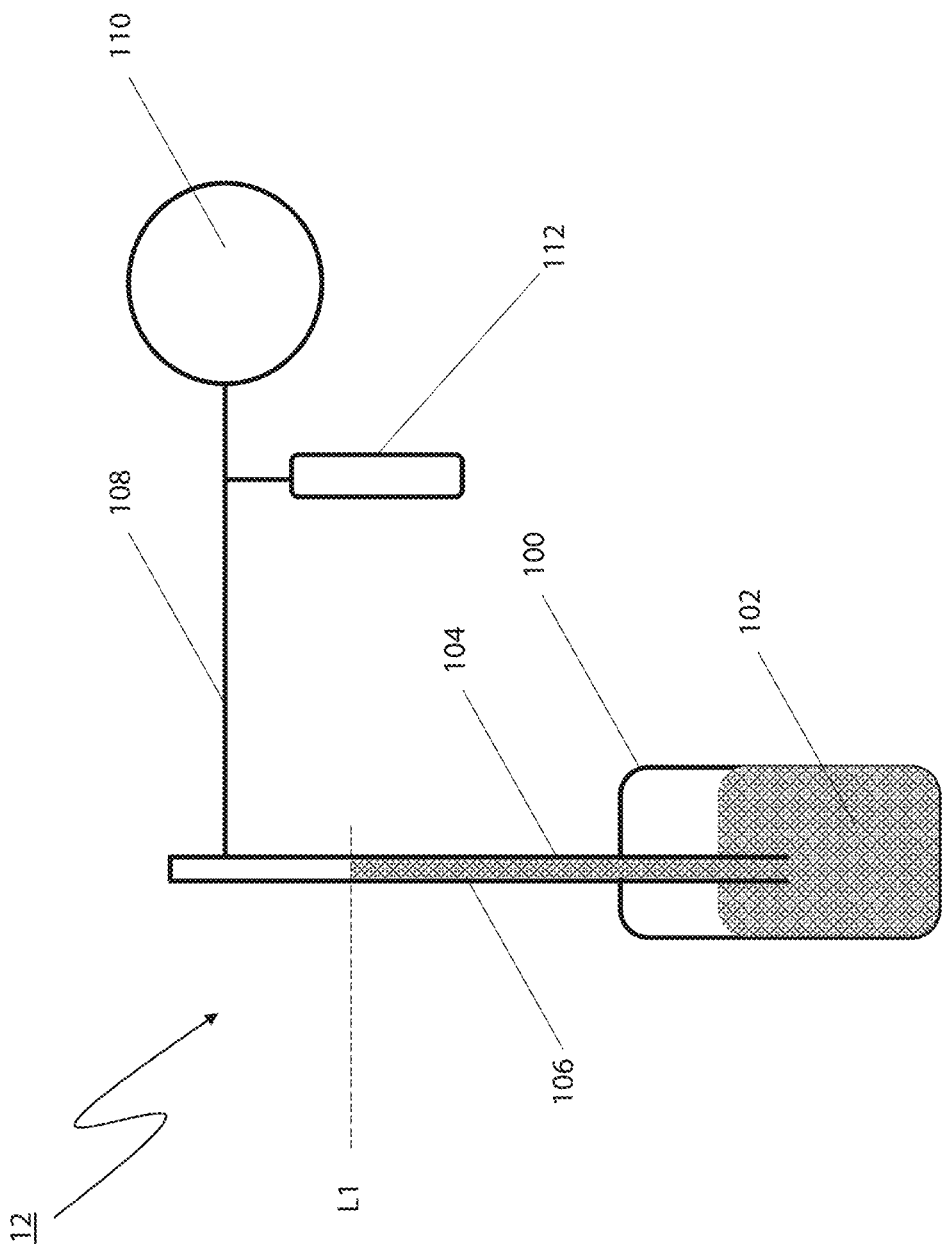
Figure 26C:
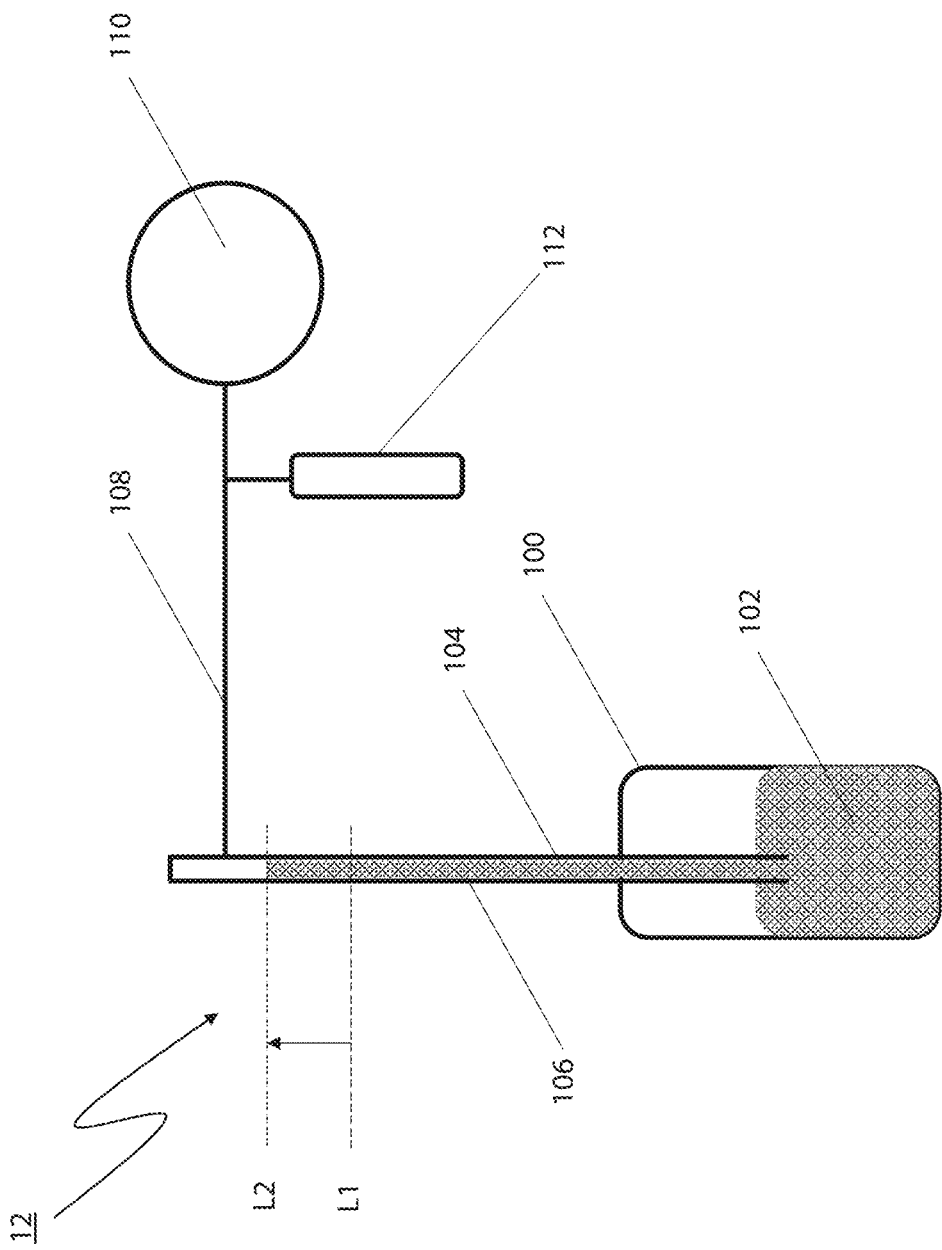
Figure 26D:
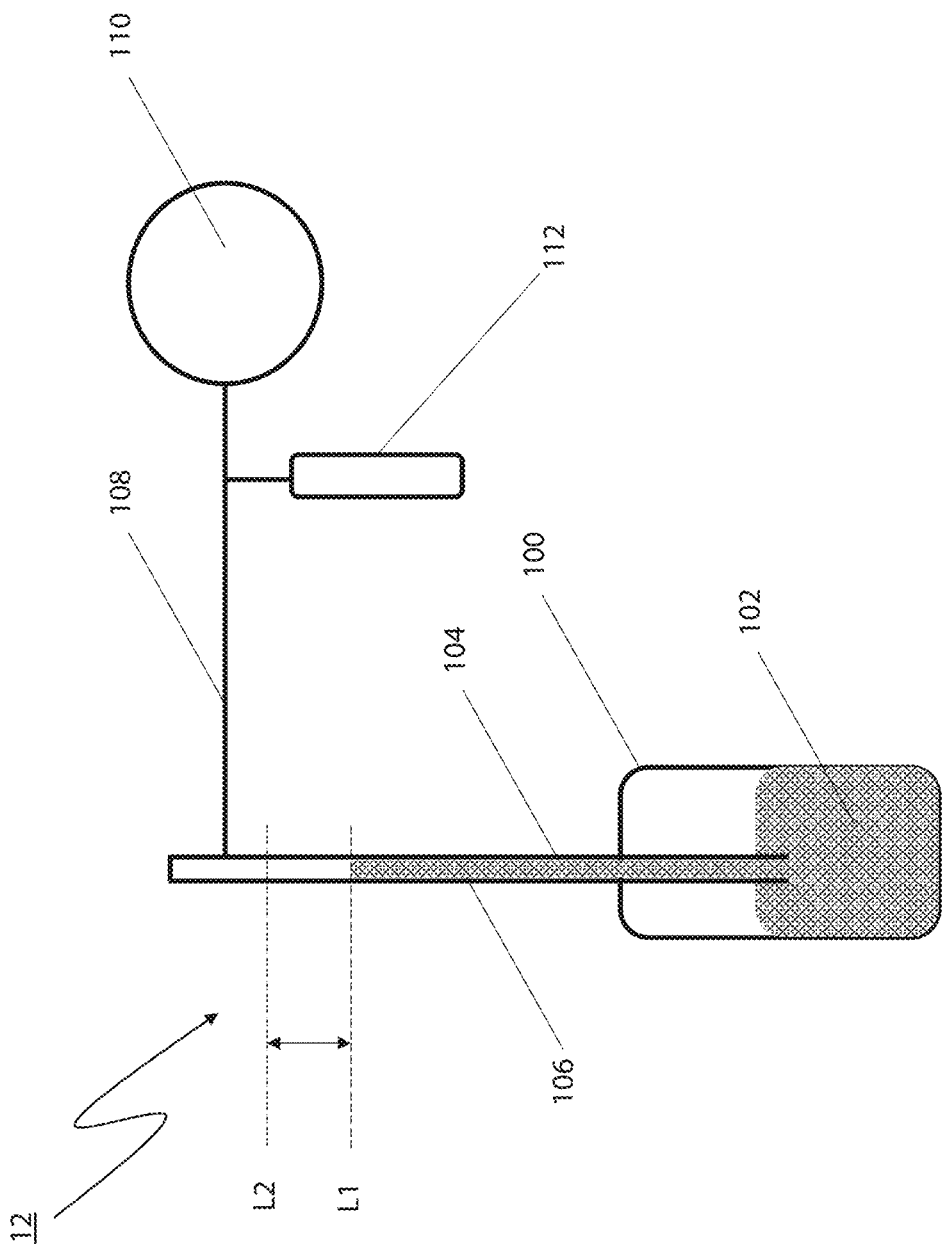

As shown in FIG. 26B, fluid 102 can be encouraged from sample container 100 to capillary/reservoir 104/106. Fluid 102 can attain level L1 within capillary/reservoir 104/106, as shown. As shown in FIG. 26C, fluid 102 can be further encouraged into capillary/reservoir 104/106 such that fluid 102 attains a second level, L2, which level can be higher than L1. During the encouragement of fluid 102 into capillary/reservoir 104/106 to attain level L2, the pressure within capillary/reservoir 104/106 can be monitored by pressure transducer 110, thereby allowing for development of a pressure-time curve. (It should be understood, however, that the pressure within the reservoir can also be monitored during an initial introduction of fluid 102 into capillary/reservoir 104/106.) Capillary/reservoir 104/106 can be vented to the exterior environment at any point during system operation, e.g., before introduction of fluid 102 to capillary/reservoir 104/106, after initial introduction of fluid 102 to capillary/reservoir 104/106, or even after further a post-initial introduction of fluid 102 to capillary/reservoir 104/106, e.g., after fluid 102 attains level L2 as shown in FIG. 26C. As shown in FIG. 26D, fluid 102 can be encouraged out of capillary/reservoir 104/106, e.g., such that the amount of fluid 102 in reservoir 106 goes from L2 to L1, as shown in FIG. 26D. Fluid 102 can be encouraged from capillary/reservoir 104/106 by, e.g., a pressure originating from priming volume 112, a pressure affected by reducing the volume of capillary/reservoir 104/106, by some other pressure source, or any combination of the foregoing. It should be understood that fluid 102 can be drawn up into and encouraged out of capillary/reservoir 104/106 multiple times, thereby allowing a user to obtain multiple readings/statistics on a given sample. This can be useful in, e.g., coagulation analyses, where a user may wish to assess the viscosity of a given sample over time, e.g., at 30-second intervals.

What is claimed:

1. A method, comprising:
    encouraging a fluid sample through a conduit into a reservoir;
    monitoring a pressure within the reservoir related to the encouraging the fluid sample into the reservoir as a function of time so as to generate at least a first set of pressure vs. time data;
    encouraging the fluid sample out of the reservoir and monitoring a pressure within the reservoir related to the encouraging the fluid sample out of the reservoir as a function of time so as to generate a second set of pressure vs. time data, and
    based at least in part on the first set of pressure vs. time data and the second set of pressure vs. time data, determining one or more of a viscosity, a viscosity as a function of shear rate, or a flow resistance of the fluid sample.

2. The method of claim 1, further comprising relating the one or more of a viscosity, a viscosity as a function of shear rate, or a flow resistance of the fluid sample to a physiologic state of a subject.

3. The method of claim 2, further comprising administering a treatment or withdrawing a treatment in response to the physiologic state of the subject.

4. The method of claim 1, comprising determining, based at least in part on the first set of pressure vs. time data, a viscosity of the fluid sample.

5. The method of claim 1, comprising determining, based at least in part on the first set of pressure vs. time data, a viscosity as a function of shear rate of the fluid sample.

6. The method of claim 1, comprising determining, based at least in part on the first set of pressure vs. time data, a flow resistance of the fluid sample.

7. The method of claim 1, wherein the fluid sample is encouraged into the reservoir by expanding the reservoir.

8. The method of claim 1, wherein the fluid sample is encouraged into the reservoir by applying a negative pressure from a source in fluid communication with the reservoir.

9. The method of claim 1, further comprising reducing a pressure within the reservoir by expanding a priming volume in fluid communication with the reservoir.

10. The method of claim 9, further comprising interrupting fluid communication between the priming volume and the reservoir.

11. The method of claim 1, wherein determining the viscosity, the viscosity as a function of shear rate, or the flow resistance of the fluid sample is based at least in part on an average that comprises the first set of pressure vs. time data and the second set of pressure vs. time data.

12. The method of claim 1, wherein the reservoir is in fluid communication with a sample container from which sample container the fluid sample originates.

13. The method of claim 1, wherein the fluid sample comprises one or more of (1) whole blood, (2) a blood plasma, or (3) whole blood during coagulation.

14. An apparatus, comprising:
    a conduit configured to communicate a fluid therein;
    a reservoir, the reservoir being in fluid communication with the conduit;
    a transducer, the transducer configured to measure a pressure within the first reservoir related to fluid entry and/or fluid egress from the reservoir; and a memory in communication with the transducer, the memory configured to record at a first set of pressure vs. time data related to fluid entry into the reservoir and a second set of pressure vs. time data related to fluid egress from the reservoir; and further comprising a processor in communication with the transducer, the processor being configured to execute instructions to relate at least the first set of pressure vs. time data and the second set of pressure vs. time data of the transducer to a viscosity of a fluid communicated into and out of the reservoir to any one or more of a viscosity, a viscosity as a function of shear rate, or a flow resistance of a fluid sample communicated within the conduit.

15. The apparatus of claim 14, the processor being configured to execute instructions to relate an average that comprises at least the first set of pressure vs. time data of the transducer and the second set of pressure vs. time data of the transducer to a viscosity of a fluid communicated into and/or out of the reservoir to any one or more of a viscosity, a viscosity as a function of shear rate, or a flow resistance of the fluid.

16. The apparatus of claim 14, further comprising a priming volume, the priming volume in interruptible fluid communication with the reservoir.

17. The apparatus of claim 16, wherein the priming volume is operable to draw a fluid through the conduit into the reservoir.

18. The apparatus of claim 16, wherein the priming volume is a syringe.

19. The apparatus of claim 14, wherein the reservoir is a syringe.

20. The apparatus of claim 14, wherein the reservoir is expandable.

21. A method, comprising:
effecting communication of a fluid though a conduit of a component,
the component comprising (i) a conduit configured to communicate a fluid therein; (ii) a reservoir, the reservoir being in fluid communication with the conduit; (iii) a transducer, the transducer configured to measure a pressure within the reservoir related to fluid entry to the reservoir and fluid egress from the reservoir; and (iv) a memory in communication with the transducer, the memory configured to record at least a first set of pressure vs. time data related to fluid entry to the reservoir and a second set of pressure vs. time data related to fluid egress from the reservoir, and
based at least in part on the first set of pressure vs. time data and the second set of pressure vs. time data, determining one or more of a viscosity, a viscosity as a function of shear rate, or a flow resistance of the fluid sample.

22. The method of claim 21, wherein the fluid comprises a subject's sample of whole blood, plasma, or coagulating blood.

23. The method of claim 22, further comprising classifying a disease state of the subject based on operation of the component.

24. The method of claim 23, further comprising recommending a treatment for the disease state of the subject.

25. The method of claim 21, wherein the communication of the fluid is automated.

26. The method of claim 21, wherein the viscosity, the viscosity as a function of shear rate, or the flow resistance of the fluid sample is based at least in part on an average that comprises the first set of pressure vs. time data and the second set of pressure vs. time data.

27. The method of claim 21, wherein the reservoir is expandable.

* * * * *